United States Patent
Tung et al.

(10) Patent No.: US 6,559,137 B1
(45) Date of Patent: *May 6, 2003

(54) SULPHONAMIDE DERIVATIVES AS PRODRUGS OF ASPARTYL PROTEASE INHIBITORS

(75) Inventors: Roger Dennis Tung, Beverly, MA (US); Michael Robin Hale, Bedford, MA (US); Christopher Todd Baker, Waltham, MA (US); Eric Steven Furfine, Durham, NC (US); Istvan Kaldor, Durham, NC (US); Wieslaw Mieczylaw Kazmierski, Raleigh, NC (US); Andrew Spaltenstein, Raleigh, NC (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/602,494

(22) Filed: Jun. 23, 2000

Related U.S. Application Data

(63) Continuation of application No. PCT/US98/04595, filed on Mar. 9, 1998, which is a continuation of application No. 08/998,050, filed on Dec. 24, 1997, now Pat. No. 6,436,989.

(51) Int. Cl.[7] .................... A61K 31/16; A61K 31/165; C07C 311/00
(52) U.S. Cl. .................... 514/99; 514/101; 514/347; 514/475; 514/601; 514/604; 514/605; 549/475; 546/293; 564/84; 564/86; 564/96; 564/98; 564/99
(58) Field of Search .................... 549/475; 546/293; 564/84, 86, 96, 98, 99; 514/347, 475, 601, 604, 605, 101, 99

(56) References Cited

U.S. PATENT DOCUMENTS

| | | | |
|---|---|---|---|
| 3,743,722 A | 7/1973 | Nolan et al. | 424/98 |
| 4,330,542 A | 5/1982 | Descamps et al. | 424/248.5 |
| 4,629,724 A | 12/1986 | Ryono et al. | 514/18 |
| 5,196,438 A | 3/1993 | Martin et al. | 514/311 |
| 5,354,866 A | 10/1994 | Kempf et al. | 546/265 |
| 5,585,397 A | * 12/1996 | Tung et al. | 514/473 |
| 5,723,490 A | 3/1998 | Tung et al. | 514/478 |
| 5,783,701 A | * 7/1998 | Tung et al. | 546/169 |
| 5,843,946 A | 12/1998 | Vasquez et al. | 514/252 |
| 6,319,946 B1 | * 11/2001 | Hale et al. | 514/464 |

FOREIGN PATENT DOCUMENTS

| | | |
|---|---|---|
| DE | 3542567 | 6/1986 |
| EP | 0 022 118 | 1/1981 |
| EP | 0 181 071 | 5/1986 |
| EP | 0 264 795 | 4/1988 |
| EP | 0 346 847 | 12/1989 |
| EP | 0 364 804 | 4/1990 |
| EP | 0 468 641 | 1/1992 |
| EP | 0 486 948 | 5/1992 |
| EP | 0 541 168 | 5/1993 |
| EP | 0 594 540 A1 | 4/1994 |
| GB | 2167759 | 6/1986 |
| GB | 2200115 | 7/1988 |
| JP | 59046252 | 3/1984 |
| JP | 59048449 | 3/1984 |
| JP | 61071830 | 4/1986 |
| WO | WO 90/07329 | 7/1990 |
| WO | WO 91/00725 | 1/1991 |
| WO | WO 91/18866 | 12/1991 |
| WO | WO 92/08688 | 5/1992 |
| WO | WO 92/08698 | 5/1992 |
| WO | WO 92/08699 | 5/1992 |
| WO | WO 92/08700 | 5/1992 |
| WO | WO 92/08701 | 5/1992 |
| WO | WO 92/17176 | 10/1992 |
| WO | WO 93/23368 | 11/1993 |
| WO | WO 93/23379 | 11/1993 |
| WO | WO 93/23388 | 11/1993 |
| WO | WO 94/04491 | 3/1994 |
| WO | WO 94/04492 | 3/1994 |
| WO | WO 94/04493 | 3/1994 |
| WO | WO94/05639 | 3/1994 |
| WO | WO 94/10134 | 5/1994 |
| WO | WO 94/10136 | 5/1994 |
| WO | WO 94/18192 | 8/1994 |
| WO | WO 94/19322 | 9/1994 |
| WO | WO 95/06030 | 3/1995 |
| WO | WO95/07269 | 3/1995 |
| WO | WO95/09843 | 4/1995 |
| WO | WO95/14016 | 5/1995 |
| WO | WO95/32185 | 11/1995 |
| WO | WO 96/33187 | 10/1996 |

OTHER PUBLICATIONS

Searle et al, Chemical Abstracts, vol. 134:66130, 2001.*
McDale et al., Chemical Abstracts, vol. 132:256027, 2000.*
Armitage et al., Chemical Abstracts, vol. 132:93472, 2000.*
Brouwer et al., Chemical Abstracts, vol. 132:30816, 1999.*
S. J. Hays et al., "Synthesis of cis–4–(Phosphonooxy)–2–piperidinecarboxylic Acid, an N–Methyl–D–aspartate Antagonist", J. Org. Chem., 56, pp. 4984–4086 (1991).

(List continued on next page.)

*Primary Examiner*—Richard L. Raymond
(74) *Attorney, Agent, or Firm*—James F. Haley, Jr.; Min Wang; Fish & Neave

(57) ABSTRACT

The present invention relates to prodrugs of a class of sulfonamides which are aspartyl protease inhibitors. In one embodiment, this invention relates to a novel class of prodrugs of HIV aspartyl protease inhibitors characterized by favorable aqueous solubility, high oral bioavailability and facile in vivo generation of the active ingredient. This invention also relates to pharmaceutical compositions comprising these prodrugs. The prodrugs and pharmaceutical compositions of this invention are particularly well suited for decreasing the pill burden and increasing patient compliance. This invention also relates to methods of treating mammals with these prodrugs and pharmaceutical compositions.

41 Claims, No Drawings

OTHER PUBLICATIONS

Y. Kiso et al., "'O→N Intramolecular Acyl Migration'–type Prodrugs of Tripeptide Inhibitors of HIV Protease", *Peptides: Chemistry, Structure and Biology*, 61, pp. 157–159 (1996).

J.W. Perich et al., "The Synthesis of Multiple O–Phosphoseryl–Containing Peptides via Phenyl Phosphate Protection", *J. Org. Chem.*, 53, pp. 4103–4015 (1988).

M.S. Plummer et al., "Design of Peptidomimetic Ligand for the pp60$^{src}$ SH2 Domain", *Bioorganic & Medicinal Chemistry*, 5, pp. 41–47 (1997).

S. Yamaguchi et al., "Synthesis of HIV Protease Dipeptide Inhibitors and Prodrugs", *Peptide Chemistry 1996*, pp. 297–300 (1997).

Banker et al., *Modern Pharmaceutics*, pp. 627–629 (1996).

R.D. Bindal et al., "Ab Initio Calculations on N–Methylmethanesulfonamide and Methyl Methanesulfonate for the Development of Force Field Torsional Parameters and Their Use in the Conformational Analysis of Some Novel Estrogens", *J. Am. Chem. Soc.*, 112, pp. 7861–7868 (1990).

R. Bone et al., "X–ray Crystal Structure of the HIV Protease Complex with L–700,417, an Inhibitor with Pseudo $C_2$ Symmetry", *J. Am. Chem. Soc.*, 113, pp. 9382–9384 (1991).

R.F. Borch et al., "The Cyanohydridoborate Anion as a Selective Reducing Agent", *J. Am. Chem. Soc.*, 93, pp. 2897–2904 (1971).

J.C. Craig et al., "Antiviral Synergy Between Inhibitors of HIV Proteinase and Reverse Transcriptase", *Antiviral Chem. and Chemotherapy*, 4(3), pp. 161–166 (1990).

S. Crawford et al., "A Deletion Mutation in the 5' Part of the pol Gene of Moloney Murine Leukemia Virus Blocks Proteolytic Processing of the gag and pol Polyproteins", *J. Virol.*, 53, pp. 899–907 (1985).

M. Cushman et al., "Development of Methodology for the Synthesis of Stereochemically Pure PheΨ[$CH_2N$]Pro Linkages in HIV Protease Inhibitors", *J. Org. Chem.*, 56, pp. 4161–4167 (1991).

D.S. Dhanoa et al., "The Synthesis of Potent Macrocyclic Renin Inhibitors", *Tetrahedron Lett.*, 33, pp. 1725–28 (1992).

G.B. Dreyer et al., "Hydroxyethelene Isostere Inhibitors of Human Immunodeficiency Virus–1 Protease: Structure–Activity Analysis Using Enzyme Kinetics, X–ray Crystallography, and Infected T–Cell Assays", *Biochemistry*, 31, pp. 6646–6659 (1992).

B.E. Evans et al., "A Stereocontrolled Synthesis of Hydroxyethylene Dipeptide Isosteres Using Novel, Chiral Aminoalkyl Epoxides and Y–(Aminoalkyl) Y–Lactones", *J. Org. Chem.*, 50, pp. 4615–4625 (1985).

G.A. Flynn et al., "An Acyl–Iminium Ion Cyclization Route to a Novel Conformationally Restricted Dipeptide Mimic: Applications to Angiotensin–Converting Enzyme Inhibition", *J. Am. Chem. Soc.*, 109, pp. 7914–7915 (1987).

G. Fontenot et al., "PCR Amplification of HIV–1 Proteinase Sequences Directly from Lab Isolates Allows Determination of Five Conserved Domains", *Virology*, 190, pp. 1–10 (1992).

P.G. Gassman and T.L. Guggenheim, "Opening of Epoxides with Trimethylsilyl Cyanide to Produce β–Hydroxy Isonitriles. A General Synthesis of Oxazolines and β–Amino Alcohols", *J. Am. Chem. Soc.*, 104, pp. 5849–5850 (1982).

E.E. Gilbert, "Recent Developments in Preparative Sulfonation and Sulfation", *Synthesis*, 1969, pp. 3–10 (1969).

A. Goldblum, "Modulation of the Affinity of Aspartic Proteases by the Mutated Residues in Active Site Models", *FEBS*, 261, pp. 241–244 (1990).

D. Grobelny et al., "Selective Phosphinate Transition–State Analogue Inhibitors of the Protease of Human Immunodeficiency Virus", Biochem. Biophys. Res. Commun., 169, pp. 1111–1116 (1990).

G.D. Hartman et al., "4–Substituted Thiophene– and Furan–2–sulfonamides as Topical Carbonic Anhydrase Inhibitors", *J. Med. Chem.*, 35, pp. 3822–3831 (1992).

J.R. Huff, "HIV Protease: A Novel Chemotherapeutic Target for AIDS", *Journal of Medicinal Chemistry*, 34(8), pp. 2305–2314 (1991).

K.Y. Hui et al., "A Rational Approach in the Search for Potent Inhibitors Against HIV Proteinase", *FASEB*, 5, pp. 2606–2610 (1991).

N.E. Kohl et al., "Active Human Immunodeficiency Virus Protease Is Required for Viral Infectivity", *Proc. Natl. Acad. Sci. USA*, 85, pp. 4686–4690 (1988).

X. Lin et al., "Enzymatic Activities of Two–Chain Pepsinogen, Two–Chain Pepsin, and the Amino–Terminal Lobe of Pepsinogen", *J. Biol. Chem.*, 267(24), pp. 17257–17263 (1992).

M. Kahn et al., "Examination of HIV–1 Protease Secondary Structure Specificity Using Conformationally Constrained Inhibitors", *J. Med. Chem.*, 34, pp. 3395–3399 (1991).

G.R. Marshall, "Computer–Aided Drug Design", *Ann. Rev. Pharmacol. Toxicol.*, 27. pp. 193–213 (1987).

J.A. Martin, "Recent Advances in the Design of HIV Proteinase Inhibitors", *Antiviral Research*, 17, pp. 265–78 (1992).

T.D. Meek et al., "Inhibition of HIV–1 Protease in Infected T–Lymphocytes by Synthetic Peptide Analogues", *Nature*, 343, pp. 90–92 (1990).

M. Miller et al., "Structure of Complex of Synthetic HIV–1 Protease with a Substrate–Based Inhibitor at 2.3 Å Resolution", *Science*, 246, pp. 1149–1152 (1989).

M. Miller et al., "Crystal Structure of a Retroviral Protease Proves Relationship to Aspartic Protease Family", *Nature*, 337, pp. 576–579 (1989).

H. Mitsuya and S. Broder, "Inhibition of the in vitro Infectivity and Cytopathic Effect of Human T–Lymphotropic Virus Type III/Lymphoadenopathy–Associated Virus (HTLV–III/LAV) by 2',3'–Dideoxynucleosides", *Proc. Natl. Acad. Sci. USA*, 83, pp. 1911–1915 (1986).

K.H.M. Murthy et al., "The Crystal Structures at 2.2–Å Resolution of Hydroxethylene–Based Inhibitors Bound to Human Immunodeficiency Virus Type 1 Protease Show That the Inhibitors Are Present in Two Distinct Orientations", *J. Biol. Chem.*, 267, pp. 22770–22778 (1992).

J.B. Nicholas et al., "A Molecular Mechanics Valence Force Field for Sulfonamides Derived by ab Initio Methods", *J. Phys. Chem.*, 95, pp. 9803–9811 (1991).

L.E. Overman and L.A. Flippin, "Facile Aminolysis of Epoxides with Diethylaluminum Amides", *Tetrahedron Letters*, 22, pp. 195–198 (1981).

J. Palca, "Shooting at a New HIV Target", *Science*, 247, p. 410 (1990).

L.H. Pearl et al., "A Structural Model for the Retroviral Proteases", *Nature*, 329, pp. 351–354 (1987).

M. Popvic et al., "Detection, Isolation, and Continuous Production of Cytopathic Retroviruses (HTLV–III) from Patients with AIDS and Pre–AIDS", Science, 224, pp. 497–500 (1984).

G.H. Posner and D.Z. Rogers, "Organic Reactions at Alumina Surfaces. Mild and Selective Opening of Arene and Related Oxides by Weak Oxygen and Nitrogen Nucleophiles", J. Am. Chem. Soc., 99, 8214–18 (1977).

M.D. Power et al., "Nucleotide Sequence of SRV–1, a Type D Simian Acquired Immune Deficiency Syndrome Retrovirus" Science, 231, pp. 1567–1572 (1986).

N.A. Roberts, "Rational Design of Peptide–Based HIV Proteinase Inhibitors", Science, 248, pp. 358–361 (1990).

S. Scharpe et al., "Proteases and Their Inhibitors: Today and Tomorrow", Biochimie, 73, pp. 121–126 (1991).

S.K. Sharma et al., "Could Angiotensin I Be Produced from a Renin Substrate by the HIV–1 Protease?", Anal. Biochem., 198, pp. 363–367 (1991).

H. Toh et al., "Close Structural Resemblance Between Putative Polymerase of a Drosophila Transposable Genetic Element 17.6 and pol Gene Product of Moloney Murine Leukemia Virus", EMBO J., 4, pp. 1267–1272 (1985).

S. Sawada et al., "Synthesis and Antitumor Activity of A–Ring or E–Lactone Modified Water–Soluble Prodrugs of 20(S)–Camptothecin, Including Development of Irinotecan Hydrochloride Trihydrate (CPT–11)", Current Pharmaceutical Design, 1, pp. 113–132 (1995).

J. M. Balkovec et al., "Synthesis, Stability, and Biological Evaluation of Water–Soluble Prodrugs of a New Echinocandin Lipopeptide. Discovery of a Potential Clinical Agent for the Treatment of Systemic Candidiasis and Pneumocystis carinii Pneumonia (PCP)", J. Med. Chem., 35, pp. 194–198 (1992).

* cited by examiner

SULPHONAMIDE DERIVATIVES AS PRODRUGS OF ASPARTYL PROTEASE INHIBITORS

CROSS-REFERENCE TO RELATED APPLICATIONS

This application is a continuation of co-pending International patent application PCT/US98/04595, filed Mar. 9, 1998, which designates the United States and claims priority from U.S. patent application Ser. No. 08/998,050, filed Dec. 24, 1997, now U.S. Pat. No. 6,436,989 B1.

TECHNICAL FIELD OF THE INVENTION

The present invention relates to prodrugs of a class of sulfonamides which are aspartyl protease inhibitors. In one embodiment, this invention relates to a novel class of prodrugs of HIV aspartyl protease inhibitors characterized by favorable aqueous solubility, high oral bioavailability and facile in vivo generation of the active ingredient. This invention also relates to pharmaceutical compositions comprising these prodrugs. The prodrugs and pharmaceutical compositions of this invention are particularly well suited for decreasing the pill burden and increasing patient compliance. This invention also relates to methods of treating mammals with these prodrugs and pharmaceutical compositions.

BACKGROUND OF THE INVENTION

Aspartyl protease inhibitors are considered the most effective current drug in the fight against HIV infection. These inhibitors, however, require certain physicochemical properties in order to achieve good potency against the enzyme. One of these properties is high hydrophobicity. Unfortunately, this property results in poor aqueous solubility and low oral bioavailability.

U.S. Pat. No. 5,585,397 describes a class of sulfonamide compounds that are inhibitors of the aspartyl protease enzyme. These compounds illustrate the drawbacks concomitant to pharmaceutical compositions comprising hydrophobic aspartyl protease inhibitors. For example, VX-478 (4-amino-N-((2-syn,3S)-2-hydroxy-4-phenyl-3((S)-tetrahydrofuran-3-yl-oxycarbonylamino)-butyl-N-isobutyl-benzenesulfonamide) is an aspartyl protease inhibitor disclosed in the '397 patent. It has a relatively low aqueous solubility. While the oral bioavailability of this inhibitor in a "solution" formulation is excellent, the dosage of VX-478 in this form is severely limited by the amount of liquid present in the particular liquid dosage from, e.g., encapsulated into a soft gelatin capsule. A higher aqueous solubility would increase drug load per unit dosage of VX-478.

Currently, the solution formulation of VX-478 produces an upper limit of 150 mg of VX-478 in each capsule. Given a therapeutic dose of 2400 mg/day of VX-478, this formulation would require a patient to consume 16 capsules per day. Such a high pill burden would likely result in poor patient compliance, thus producing sub-optimal therapeutic benefit of the drug. The high pill burden is also a deterrent to increasing the amount of the drug administered per day to a patient. Another drawback of the pill burden and the concomitant patient compliance problem is in the treatment of children infected with HIV.

Furthermore, these "solution" formulations, such as the mesylate formulation, are at a saturation solubility of VX-478. This creates the real potential of having the drug crystallize out of solution under various storage and/or shipping conditions. This, in turn, would likely result in a loss of some of the oral bioavailability achieved with VX-478.

One way of overcoming these problems is to develop a standard solid dosage form, such as a tablet or a capsule or a suspension form. Unfortunately, such solid dosage forms have much lower oral bioavailability of the drug.

Thus, there is a need to improve the drug load per unit dosage form for aspartyl protease inhibitors. Such an improved dosage form would reduce the pill burden and increase patient compliance. It would also provide for the possibility of increasing the amounts of the drug administered per day to a patient.

SUMMARY OF THE INVENTION

The present invention provides novel prodrugs of a class of sulfonamide compounds that are inhibitors of aspartyl protease, in particular, HIV aspartyl protease. These prodrugs are characterized by excellent aqueous solubility, increased bioavailability and are readily metabolized into the active inhibitors in vivo. The present invention also provides pharmaceutical compositions comprising these prodrugs and methods of treating HIV infection in mammals using these prodrugs and the pharmaceutical compositions thereof.

These prodrugs can be used alone or in combination with other therapeutic or prophylactic agents, such as anti-virals, antibiotics, immunomodulators or vaccines, for the treatment or prophylaxis of viral infection.

It is a principal object of this invention to provide a novel class of prodrugs of sulfonamide compounds that are aspartyl protease inhibitors, and particularly, HIV aspartyl protease inhibitors. This novel class of sulfonamides is represented by formula I:

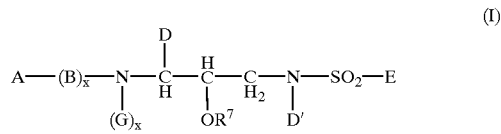

wherein:

A is selected from H; Ht; —$R^1$—Ht; —$R^1$—$C_1$–$C_6$ alkyl, which is optionally substituted with one or more groups independently selected from hydroxy, $C_1$–$C_4$ alkoxy, Ht, —O—Ht, —$NR^2$—CO—$N(R^2)_2$ or —CO—$N(R^2)_2$; —$R^1$—$C_2$–$C_6$ alkenyl, which is optionally substituted with one or more groups independently selected from hydroxy, $C_1$–$C_4$ alkoxy, Ht, —O—Ht, —$NR^2$—CO—$N(R^2)_2$ or —CO—$N(R^2)_2$; or $R^7$;

each $R^1$ is independently selected from —C(O)—, —$S(O)_2$—, —C(O)—C(O)—, —O—C(O)—, —O—$S(O)_2$, —$NR^2$—$S(O)_2$—, —$NR^2$—C(O)— or —$NR^2$—C(O)—C(O)—;

each Ht is independently selected from $C_3$–$C_7$ cycloalkyl; $C_5$–$C_7$ cycloalkenyl; $C_6$–$C_{10}$ aryl; or a 5–7 membered saturated or unsaturated heterocycle, containing one or more heteroatoms selected from N, $N(R^2)$, O, S and $S(O)_n$; wherein said aryl or said heterocycle is optionally fused to Q; and wherein any member of said Ht is optionally substituted with one or more substituents independently selected from oxo, —$OR^2$, $SR^2$, —$R^2$, —$N(R^2)(R^2)$, —$R^2$—OH, —CN, —$CO_2R^2$, —C(O)—$N(R^2)_2$, —$S(O)_2$—$N(R^2)_2$, —$N(R^2)$—C(O)—$R^2$, —C(O)—$R^2$, —$S(O)_n$—$R^2$, —$OCF_3$, —$S(O)_n$—Q, methylenedioxy, —N($R^2$)—S(O)$_2$($R^2$), halo, —CF$_3$, —NO$_2$, Q, —OQ, —OR$^7$, —SR$^7$, —R$^7$, —N($R^2$)($R^7$) or —N($R^7$)$_2$;

each $R^2$ is independently selected from H, or C$_1$–C$_4$ alkyl optionally substituted with Q;

B, when present, is —N($R^2$)—C($R^3$)$_2$—C(O)—;

each x is independently 0 or 1;

each $R^3$ is independently selected from H, Ht, C$_1$–C$_6$ alkyl, C$_2$–C$_6$ alkenyl, C$_3$–C$_6$ cycloalkyl or C$_5$–C$_6$ cycloalkenyl; wherein any member of said $R^3$, except H, is optionally substituted with one or more substituents selected from —OR$^2$, —C(O)—NH—R$^2$, —S(O)$_n$—N($R^2$)($R^2$), Ht, —CN, —SR$^2$, —CO$_2$R$^2$, NR$^2$—C(O)—R$^2$;

each n is independently 1 or 2;

G, when present, is selected from H, $R^7$ or C$_1$–C$_4$ alkyl, or, when G is C$_1$–C$_4$ alkyl, G and $R^7$ are bound to one another either directly or through a C$_1$–C$_3$ linker to form a heterocyclic ring; or when G is not present (i.e., when x in (G)$_x$ is 0), then the nitrogen to which G is attached is bound directly to the $R^7$ group on —OR$^7$;

D and D' are independently selected from Q; C$_1$–C$_6$ alkyl, which is optionally substituted with one or more groups selected from C$_3$–C$_6$ cycloalkyl, —OR$^2$, —R$^3$, —O—Q or Q; C$_2$–C$_4$ alkenyl, which is optionally substituted with one or more groups selected from C$_3$–C$_6$ cycloalkyl, —OR$^2$, —R$^3$, —O—Q or Q; C$_3$–C$_6$ cycloalkyl, which is optionally substituted with or fused to Q; or C$_5$–C$_6$ cycloalkenyl, which is optionally substituted with or fused to Q;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, S(O)$_n$ or N($R^2$); wherein Q is optionally substituted with one or more groups selected from oxo, —OR$^2$, —R$^2$, —N($R^2$)$_2$, —N($R^2$)—C(O)—R$^2$, —R$^2$—OH, —CN, —CO$_2$R$^2$, —C(O)—N($R^2$)$_2$, halo or —CF$_3$;

E is selected from Ht; O—Ht; Ht—Ht; —O—R$^3$; —N($R^2$)($R^3$); C$_1$–C$_6$ alkyl, which is optionally substituted with one or more groups selected from $R^4$ or Ht; C$_2$–C$_6$ alkenyl, which is optionally substituted with one or more groups selected from $R^4$ or Ht; C$_3$–C$_6$ saturated carbocycle, which is optionally substituted with one or more groups selected from $R^4$ or Ht; or C$_5$–C$_6$ unsaturated carbocycle, which is optionally substituted with one or more groups selected from $R^4$ or Ht;

each $R^4$ is independently selected from —OR$^2$, —SR$^2$, —C(O)—NHR$^2$, —S(O)$_2$—NHR$^2$, halo, —NR$^2$—C(O)—R$^2$, —N($R^2$)$_2$ or —CN;

each $R^7$ is independently selected from $$-\!\!\left[CH_2\!-\!O\right]_{\overline{x}}\!\!-\!\!\underset{\underset{X}{\|}}{Y}\!\!-\!\!Z(M)_x \quad \text{or} \quad -\!\!\left[CH_2\!-\!O\right]_{\overline{x}}\!\!-\!\!\overset{O}{\underset{\|}{C}}\!\!-\!\!(R^9)_x M';$$

wherein each M is independently selected from H, Li, Na, K, Mg, Ca, Ba, —N($R^2$)$_4$, C$_1$–C$_{12}$-alkyl, C$_2$–C$_{12}$-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S, S(O), S(O$_2$), or N($R^2$); and wherein any hydrogen in said alkyl, alkenyl or $R^6$ is optionally replaced with a substituent selected from oxo, —OR$^2$, —R$^2$, N($R^2$)$_2$, N($R^2$)$_3$, $R^2$OH, —CN, —CO$_2$R$^2$, —C(O)—N($R^2$)$_2$, S(O)$_2$—N($R^2$)$_2$, N($R^2$)—C(O)—R$_2$, C(O)R$^2$, —S(O)$_n$—R$^2$, OCF$_3$, —S(O)$_n$—R$^6$, N($R^2$)—S(O)$_2$($R^2$), halo, —CF$_3$, or —NO$_2$;

M' is H, C$_1$–C$_{12}$-alkyl, C$_2$–C$_{12}$-alkenyl, or —R$^6$; wherein 1 to 4 —CH$_2$ radicals of the alkyl or alkenyl group is optionally replaced by a heteroatom group selected from O, S, S(O), S(O$_2$), or N($R^2$); and wherein any hydrogen in said alkyl, alkenyl or $R^6$ is optionally replaced with a substituent selected from oxo, —OR$^2$, —R$^2$, —N($R^2$)$_2$, N($R^2$)$_3$, —R$^2$OH, —CN, —CO$_2$R$^2$, —C(O)—N($R^2$)$_2$, —S(O)$_2$—N($R^2$)$_2$, —N($R^2$)—C(O)—R$_2$, —C(O)R$^2$, —S(O)$_n$—R$^2$, —OCF$_3$, —S(O)$_n$—R$^6$, —N($R^2$)—S(O)$_2$($R^2$), halo, —CF$_3$, or —NO$_2$;

Z is CH$_2$, O, S, N($R^2$)$_2$, or, when M is absent, H;

Y is P or S;

X is O or S; and $R^9$ is C($R^2$)$_2$, O or N($R^2$); and wherein when Y is S, Z is not S; and $R^6$ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, S(O)$_n$ or N($R^2$); and wherein any of said ring systems optionally contains 1 to 4 substituents independently selected from OH, C$_1$–C$_4$ alkyl, O—C$_1$–C$_4$ alkyl or OC(O)C$_1$–C$_4$ alkyl.

It is a also an object of this invention to provide pharmaceutical compositions comprising the sulfonamide prodrugs of formula I and methods for their use as prodrugs of HIV aspartyl protease inhibitors.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Ac | acetyl |
| Me | methyl |
| Et | ethyl |
| Bzl | benzyl |
| Trityl | triphenylmethyl |
| Asn | D- or L-asparagine |
| Ile | D- or L-isoleucine |
| Phe | D- or L-phenylalanine |
| Val | D- or L-valine |
| Boc | tert-butoxycarbonyl |
| Cbz | benzyloxycarbonyl (carbobenzyloxy) |
| Fmoc | 9-fluorenylmethoxycarbonyl |
| DCC | dicyclohexylcarbodiimide |
| DIC | diisopropylcarbodiimide |
| EDC | 1-(3-dimethylaminopropyl)-3-ethylcarbodiimide hydrochloride |
| HOBt | 1-hydroxybenzotriazole |
| HOSu | 1-hydroxysuccinimide |
| TFA | trifluoroacetic acid |
| DIEA | diisopropylethylamine |

-continued

| Designation | Reagent or Fragment |
|---|---|
| DBU | 1,8-diazabicyclo(5.4.0)undec-7-ene |
| EtOAc | ethyl acetate |

The following terms are employed herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

For the compounds of formula I, and intermediates thereof, the stereochemistry of $OR^7$ is defined relative to D on the adjacent carbon atom, when the molecule is drawn in an extended zig-zag representation (such as that drawn for compounds of formula XI, XV, XXII, XXIII and XXXI). If both $OR^7$ and D reside on the same side of the plane defined by the extended backbone of the compound, the stereochemistry of $OR^7$ will be referred to as "syn". If $OR^7$ and D reside on opposite sides of that plane, the stereochemistry of $OR^7$ will be referred to as "anti".

The term "aryl", alone or in combination with any other term, refers to a carbocyclic aromatic radical containing the specified number of carbon atoms.

The term "heterocyclic" refers to a stable 5–7 membered monocycle or 8–11 membered bicyclic heterocycle which is either saturated or unsaturated, and which may be optionally benzofused if monocyclic. Each heterocycle consists of carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. The heterocyclic ring may be attached by any heteroatom of the cycle which results in the creation of a stable structure. Preferred heterocycles defined above include, for example, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazoyl, benzodioxolyl, thiophenyl, tetrahydrothiophenyl and sulfolanyl.

The terms "HIV protease" and "HIV aspartyl protease" are used interchangeably and refer to the aspartyl protease encoded by the human immunodeficiency virus type 1 or 2. In a preferred embodiment of this invention, these terms refer to the human immunodeficiency virus type 1 aspartyl protease.

The term "pharmaceutically effective amount" refers to an amount effective in treating HIV infection in a patient. The term "prophylactically effective amount" refers to an amount effective in preventing HIV infection in a patient. As used herein, the term "patient" refers to a mammal, including a human.

The term "pharmaceutically acceptable carrier or adjuvant" refers to a non-toxic carrier or adjuvant that may be administered to a patient, together with a compound of this invention, and which does not destroy the pharmacological activity thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N—$(C_{1-4}$ alkyl$)^{4+}$ salts.

The term "thiocarbamates" refers to compounds containing the functional group N—$SO_2$—O.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. The explicitly shown hydroxyl is also preferred to be syn to D, in the extended zigzag conformation between the nitrogens shown in compounds of formula I.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

The compounds of the present invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The novel sulfonamides of this invention are those of formula I:

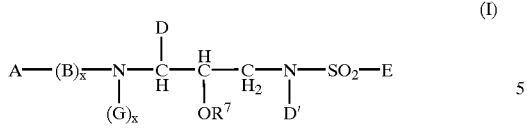

(I)

wherein:

A is selected from H; Ht; —R$^1$—Ht; —R$^1$—C$_1$–C$_6$ alkyl, which is optionally substituted with one or more groups independently selected from hydroxy, C$_1$–C$_4$ alkoxy, Ht, —O—Ht, —NR$^2$—CO—N(R$^2$)$_2$ or —CO—N(R$^2$)$_2$; —R$^1$—C$_2$–C$_6$ alkenyl, which is optionally substituted with one or more groups independently selected from hydroxy, C$_1$–C$_4$ alkoxy, Ht, —O—Ht, —NR$^2$—CO—N(R$^2$)$_2$ or —CO—N(R$^2$)$_2$; or R$^7$;

each R$^1$ is independently selected from —C(O)—, —S(O)$_2$—, —C(O)—C(O)—, —O—C(O)—, —O—S(O)$_2$, —NR$^2$—S(O)$_2$—, —NR$^2$—C(O)— or —NR$^2$—C(O)—C(O)—;

each Ht is independently selected from C$_3$–C$_7$ cycloalkyl; C$_5$–C$_7$ cycloalkenyl; C$_6$–C$_{10}$ aryl; or a 5–7 membered saturated heterocycle, containing one or more heteroatoms selected from N, N(R$^2$), O, S and S(O)$_n$; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)(R$^2$), —R$^2$—OH, —CN, —CO$_2$R$^2$, —C(O)—N(R$^2$)$_2$, —S(O)$_2$—N(R$^2$)$_2$, —N(R$^2$)—C(O)—R$^2$, —C(O)—R$^2$, —S(O)$_n$—R$^2$, —OCF$_3$, —S(O)$_n$—Q, methylenedioxy, —N(R$^2$)—S(O)$_2$(R$^2$), halo, —CF$_3$, —NO$_2$, Q, —OQ, —OR$^7$, —SR$^7$, —R$^7$, —N(R$^2$)(R$^7$) or —N(R$^7$)$_2$;

each R$^2$ is independently selected from H, or C$_1$–C$_4$ alkyl optionally substituted with Q;

B, when present, is —N(R$^2$)—C(R$^3$)$_2$—C(O)—;

each x is independently 0 or 1;

each R$^3$ is independently selected from H, Ht, C$_1$–C$_6$ alkyl, C$_2$–C$_6$ alkenyl, C$_3$–C$_6$ cycloalkyl or C$_5$–C$_6$ cycloalkenyl; wherein any member of said R$^3$, except H, is optionally substituted with one or more substituents selected from —OR$^2$, —C(O)—NH—R$^2$, —S(O)$_n$—N(R$^2$)(R$^2$) Ht, —CN, —SR$^2$, —CO$_2$R$^2$, NR$^2$—C(O)—R$^2$;

each n is independently 1 or 2;

G, when present, is selected from H, R$^7$ or C$_1$–C$_4$ alkyl, or, when G is C$_1$–C$_4$ alkyl, G and R$^7$ are bound to one another either directly or through a C$_1$–C$_3$ linker to form a heterocyclic ring; or when G is not present (i.e., when x in (G)$_x$ is 0), then the nitrogen to which G is attached is bound directly to the R$^7$ group in —OR$^7$ with the concomitant displacement of one —ZM group from R$^7$;

D and D' are independently selected from Q; C$_1$–C$_6$ alkyl, which is optionally substituted with one or more groups selected from C$_3$–C$_6$ cycloalkyl, —OR$^2$, —R$^3$, —O—Q or Q; C$_2$–C$_4$ alkenyl, which is optionally substituted with one or more groups selected from C$_3$–C$_6$ cycloalkyl, —OR$^2$, —R$^3$, —O—Q or Q; C$_3$–C$_6$ cycloalkyl, which is optionally substituted with or fused to Q; or C$_5$–C$_6$ cycloalkenyl, which is optionally substituted with or fused to Q;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, S(O)$_n$ or N(R$^2$); wherein Q is optionally substituted with one or more groups selected from oxo, —OR$^2$, —R$^2$, —N(R$^2$)$_2$, —N(R$^2$)—C(O)—R$^2$, —R$^2$—OH, —CN, —CO$_2$R$^2$, —C(O)—N(R$^2$)$_2$, halo or —CF$_3$;

E is selected from Ht; O—Ht; Ht—Ht; —O—R$^3$; —N(R$^2$)(R$^3$); C$_1$–C$_6$ alkyl, which is optionally substituted with one or more groups selected from R$^4$ or Ht; C$_2$–C$_6$ alkenyl, which is optionally substituted with one or more groups selected from R$^4$ or Ht; C$_3$–C$_6$ saturated carbocycle, which is optionally substituted with one or more groups selected from R$^4$ or Ht; or C$_5$–C$_6$ unsaturated carbocycle, which is optionally substituted with one or more groups selected from R$^4$ or Ht;

each R$^4$ is independently selected from —OR$^2$, —SR$^2$, —C(O)—NHR$^2$, —S(O)$_2$—NHR$^2$, halo, —NR$^2$—C(O)—R$^2$, —N(R$^2$)$_2$ or —CN;

each R$^7$ is independently selected from

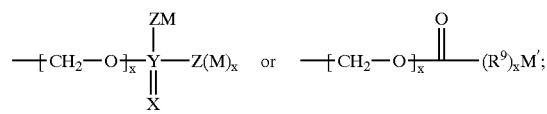

wherein each M is independently selected from H, Li, Na, K, Mg, Ca, Ba, —N(R$^2$)$_4$, C$_1$–C$_{12}$-alkyl, C$_2$–C$_{12}$-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, —R$^2$, N(R$^2$)$_2$, N(R$^2$)$_3$, R$^2$OH, —CN, —CO$_2$R$^2$, —C(O)—N(R$^2$)$_2$, S(O)$_2$—N(R$^2$)$_2$, N(R$^2$)—C(O)—R$_2$, C(O)R$^2$, —S(O)$_n$—R$^2$, OCF$_3$, —S(O)$_n$—R$^6$, N(R$^2$)—S(O)$_2$(R$^2$), halo, —CF$_3$, or —NO$_2$;

M' is H, C$_1$–C$_{12}$-alkyl, C$_2$–C$_{12}$-alkenyl, or —R$^6$; wherein 1 to 4 —CH$_2$ radicals of the alkyl or alkenyl group is optionally replaced by a heteroatom group selected from O, S, S(O), S(O$_2$), or N(R$^2$); and wherein any hydrogen in said alkyl, alkenyl or R$^6$ is optionally replaced with a substituent selected from oxo, —OR$^2$, —R$^2$, —N(R$^2$)$_2$, N(R$^2$)$_3$, —R$^2$OH, —CN, —CO$_2$R$^2$, —C(O)—N(R$^2$)$_2$, —S(O)$_2$—N(R$^2$)$_2$, —N(R$^2$)—C(O)—R$_2$, —C(O)R$^2$, —S(O)$_n$—R$^2$, —OCF$_3$, —S(O)$_n$—R$^6$, —N(R$^2$)—S(O)$_2$(R$^2$), halo, —CF$_3$, or —NO$_2$;

Z is CH$_2$, O, S, N(R$^2$)$_2$, or, when M is not present, H.

Y is P or S;

X is O or S; and

R$^9$ is C(R$^2$)$_2$, O or N(R$^2$); and wherein when Y is S, Z is not S; and

R$^6$ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, S(O)$_n$ or N(R$^2$); and wherein any of said ring systems optionally contains 1 to 4 substituents independently selected from OH, C$_1$–C$_4$ alkyl, O—C$_1$–C$_4$ alkyl or O—C(O)—C$_1$–C$_4$ alkyl.

Preferably, at least one $R^7$ is selected from:

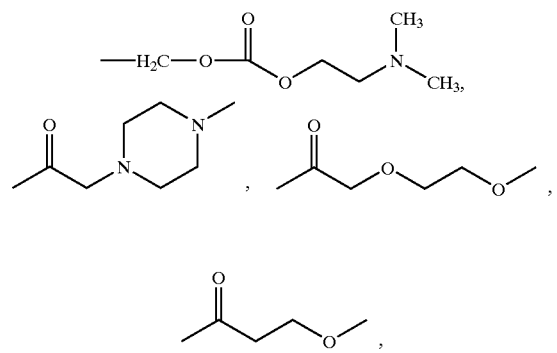

-(L)-lysine, —$PO_3Na_2$,

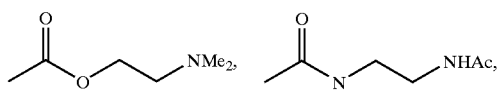

-(L)-tyrosine,

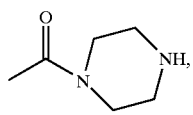

—$PO_3Mg$, —$PO_3(NH_4)_2$, —$CH_2$—$OPO_3Na_2$,

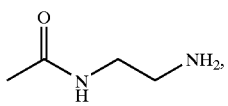

-(L)-serine, —$SO_3Na_2$,

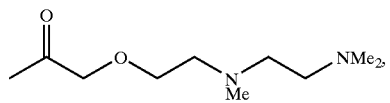

—$SO_3Mg$, —$SO_3(NH_4)_2$, —$CH_2OSO_3Na_2$, —$CH_2$—$OSO_3(NH_4)_2$,

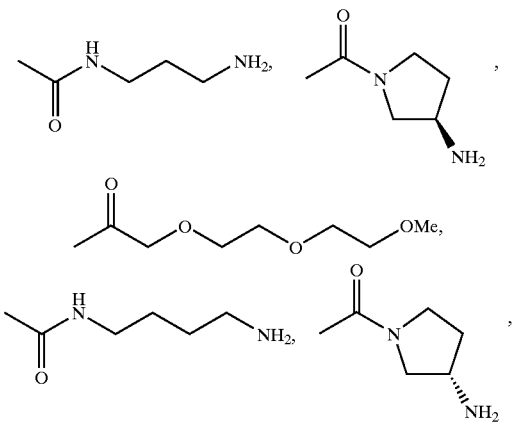

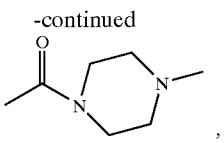

acetyl,

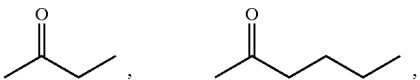

-(L)-valine, -(L)-glutamic acid, -(L)-aspartic acid, -(L)-γ-t-butyl-aspartic acid,

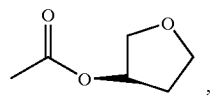

-(L)-(L)-3-pyridylalanine, -(L)-histidine, —CHO,

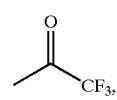

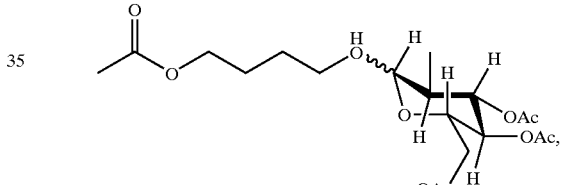

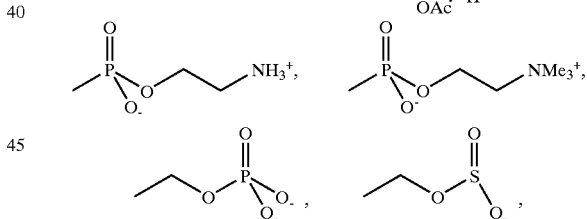

$PO_3K_2$, $PO_3Ca$, $PO_3$-spermine, $PO_3$-(spermidine)$_2$ or $PO_3$-(meglamine)$_2$.

It will be understood by those of skill in the art that component M or M' in the formulae set forth herein will have either a covalent, a covalent/zwitterionic, or an ionic association with either Z or $R^9$ depending upon the actual choice for M or M'. When M or M' is hydrogen, alkyl, alkenyl, or $R^6$, M or M' is covalently bound to $R^9$ or Z. If M is a mono- or bivalent metal or other charged species (i.e., $NH_4^+$), there is an ionic interaction between M and Z and the resulting compound is a salt.

When x is 0 in $(M)_x$, Z may be a charged species. When that occurs, the other M may be oppositely charged to produce a 0 net charge on the molecule. Alternatively, the counter ion may located elsewhere in the molecule.

Except where expressly provided to the contrary, as used herein, the definitions of variables A, $R^1$–$R^4$, $R^6$–$R^9$, Ht, B, x, n, D, D', M, Q, X, Y, Z and E are to be taken as they are defined above for the compounds of formula I.

According to a preferred embodiment, the compounds of this invention are those represented by formulas XXII, XXIII or XXXI:

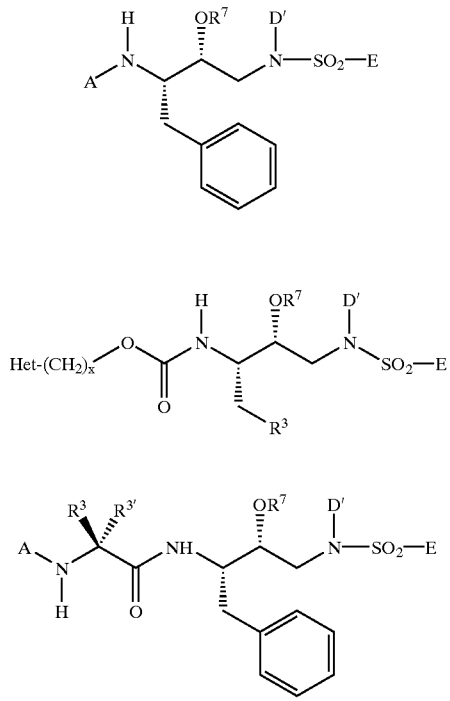

(XXII)

(XXIII)

(XXXI)

wherein A, $R^3$, $R^7$, Ht, D, D', x, E are as defined above for compounds of formula I. For ease of reference, the two $R^3$ moieties present in formula XXXI have been labeled $R^3$ and $R^{3'}$.

For compounds of formula XXII, more preferred compounds are those wherein:

A is selected from 3-tetrahydrofuryl-O—C(O)—, 3-(1,5-dioxane)-O—C(O)—, or 3-hydroxy-hexahydrofura[2,3-b]-furanyl-O—C(O)—;

D' is $C_1$–$C_4$ alkyl which is optionally substituted with one or more groups selected from the group consisting of $C_3$–$C_6$ cycloalkyl, —$OR^2$, —$R^3$, —O—Q and Q;

E is $C_6$–$C_{10}$ aryl optionally substituted with one or more substituents selected from oxo, —$OR^2$, $SR^2$, —$R^2$, —$N(R^2)_2$, —$R^2$—OH, —CN, —$CO_2R^2$, —C(O)—N($R^2)_2$, —S(O)$_2$—N($R^2)_2$, —N($R^2$)—C(O)—$R^2$, —C(O)—$R^2$, —S(O)$_n$—$R^2$, —OCF$_3$, —S(O)$_n$—Q, methylenedioxy, —N($R^2$)—S(O)$_2$($R^2$), halo, —CF$_3$, —NO$_2$, Q, —OQ, —$OR^7$, —$SR^7$, —$R^7$, —N($R^2$)($R^7$) or —N($R^7)_2$; or a 5-membered heterocyclic ring containing one S and optionally containing N as an additional heteroatom, wherein said heterocyclic ring is optionally substituted with one to two groups independently selected from —CH$_3$, $R^4$, or Ht.

Ht, insofar as it is defined as part of $R^3$, is defined as above except for the exclusion of heterocycles; and all other variables are as defined for formula I.

Even more preferred are compounds of formula XXII, wherein A is 3-tetrahydrofuryl-O—C(O)—; G is hydrogen; D' is isobutyl; E is phenyl substituted with N($R^7)_2$; each M is independently selected from H, Li, Na, K, Mg, Ca, Ba, $C_1$–$C_4$ alkyl or —N($R^2)_4$; and each M' is H or $C_1$–$C_4$ alkyl.

Another preferred embodiment for the formula XXII compounds are those wherein:

E is a 5-membered heterocyclic ring containing one S and optionally containing N as an additional heteroatom, wherein said heterocyclic ring is optionally substituted with one to two groups independently selected from —CH$_3$, $R^4$, or Ht; and all other variables are as defined for formula I.

Even more preferred are any of the formula XXII compounds set forth above, wherein $R^7$ in —$OR^7$ is —PO(OM)$_2$ or C(O)CH$_2$OCH$_2$CH$_2$OCH$_2$CH$_2$OCH$_3$ and both $R^7$ in —N($R^7)_2$ are H, wherein M is H, Li, Na, K or $C_1$–$C_4$ alkyl; or wherein $R^7$ in —$OR^7$ is C(O)CH$_2$OCH$_2$CH$_2$OCH$_3$, one $R^7$ in —N($R^7)_2$ is C(O)CH$_2$OCH$_2$CH$_2$OCH$^3$ and the other is H.

The most preferred compound of formula XXII has the structure:

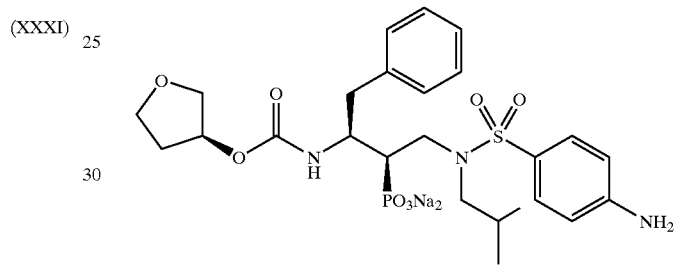

For compounds of formula XXIII, most preferred compounds are those wherein:

$R^3$ is $C_1$–$C_6$ alkyl, $C_2$–$C_6$ alkenyl, $C_5$–$C_6$ cycloalkyl, $C_5$–$C_6$ cycloalkenyl or a 5–6 membered saturated or unsaturated heterocycle, wherein any member of said $R^3$ may be optionally substituted with one or more substituents selected from the group consisting of —$OR^2$, —C(O)—NH—$R^2$, —S(O)$_n$N($R^2$)($R^2$), Ht, —CN, —$SR^2$, —C(O)$_2R^2$ and $NR^2$—C(O)—$R^2$; and D' is $C_1$–$C_3$ alkyl or $C_3$ alkenyl, wherein said alkyl or alkenyl may optionally be substituted with one or more groups selected from the group consisting of $C_3$–$C_6$ cycloalkyl, —$OR^2$, —O—Q and Q (with all other variables being defined as above for compounds of formula I).

Even more preferred are compounds of formula XXIII described above, wherein $R^7$ is —PO(OM)$_2$ or —C(O)—M'.

For compounds of formula XXXI, most preferred compounds are those wherein A is $R^1$—Ht, each $R^3$ is independently $C_1$–$C_6$ alkyl which may be optionally substituted with a substituent selected from the group consisting of —$OR^2$, —C(O)—NH—$R^2$, —S(O)$_n$N($R^2$)($R^2$), Ht, —CN, —$SR^2$, —$CO_2R^2$ or —$NR^2$—C(O)—$R^2$; and D' is $C_1$–$C_4$ alkyl, which may be optionally substituted with a group selected from the group consisting of $C_3$–$C_6$ cycloalkyl, —$OR^2$, —O—Q; and E is Ht, Ht—Ht and —$NR^2R^3$.

Even more preferred are those compounds of formula XXXI described above wherein $R^7$ is —PO(OM)$_2$ or —C(O)—M'.

TABLE I
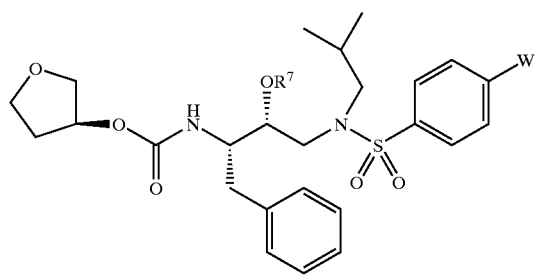
| CMPD | R⁷ | W |
|---|---|---|
| 198 |  | —NO₂ |
| 199 |  | —NH₂ |
| 200 |  | —NH₂ |
| 201 |  | —NH₂ |
| 202 |  | —NH₂ |
| 203 |  | —NH₂ |
| 204 |  | —NH₂ |
| 205 |  | —NH₂ |
| 206 |  | —NH₂ |
| 207 | 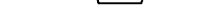 | —NH₂ |

TABLE I-continued
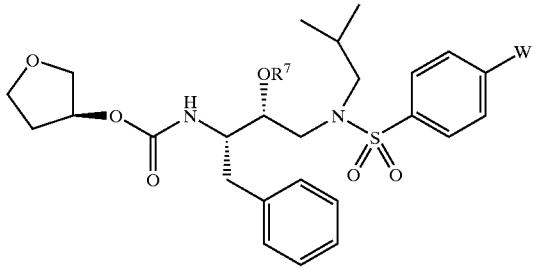
| CMPD | R⁷ | W |
|---|---|---|
| 208 | 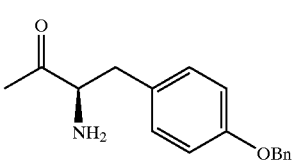 | —NO₂ |
| 209 | 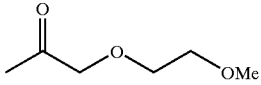 | —NO₂ |
| 210 | 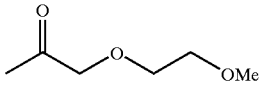 | —NH₂ |
| 211 | 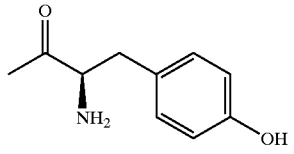 | —NH₂ |
| 212 | 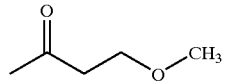 | —NH₂ |
| 213 | 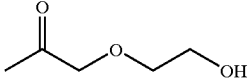 | —NH₂ |
| 214 | 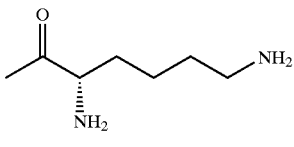 | —NH₂ |
| 215 | 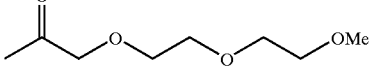 | —NH₂ |
| 216 | 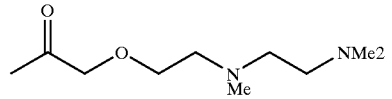 | —NH₂ |
| 217 | 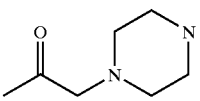 | —NH₂ |

TABLE I-continued
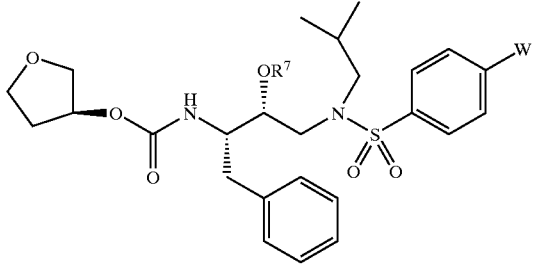
| CMPD | R⁷ | W |
|---|---|---|
| 219 | H | 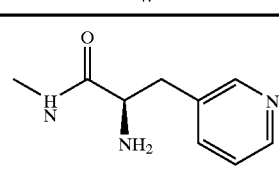 |
| 220 | H | 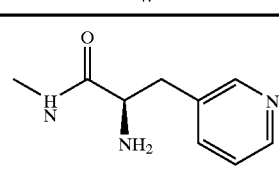 |
| 221 | H | 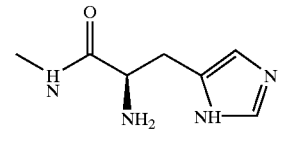 |
| 222 | H | 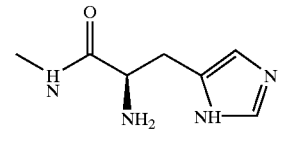 |
| 223 | H | 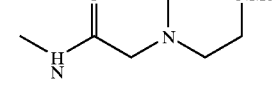 |
| 224 | H | 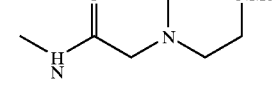 |
| 225 | 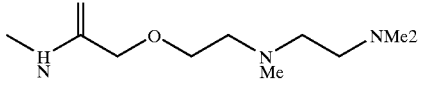 | 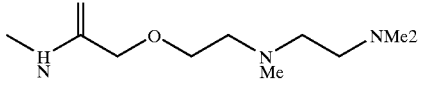 |
| 226 | 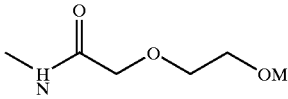 | —NO₂ |
| 227 | 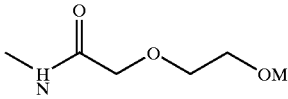 | —NO₂ |
| 228 | 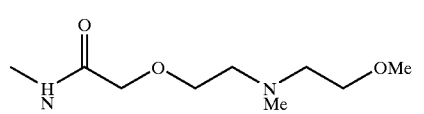 | —NH₂ |

TABLE I-continued

| CMPD | R⁷ | W |
|---|---|---|
| 229 | methylphosphonate di-sodium salt | —NH₂ |
| 230 | H | —NHC(O)CH₂OCH₂CH₂OCH₂CH₂OCH₃ |
| 231 | CH₃C(O)CH₂OCH₂CH₂OCH₂CH₂OCH₃ | —NHC(O)CH₂OCH₂CH₂OCH₂CH₂OCH₃ |
| 237 | CH₃C(O)CH₂CH₂CH₂CH₂OH | —NO₂ |
| 238 | 5-oxohexyl tri-O-acetyl-mannopyranoside | —NO₂ |
| 239 | —SO₃H | —NO₂ |
| 240 | —SO₃H | —NH₂ |
| 241 | methylphosphonate choline ester | —NO₂ |
| 242 | methylphosphonate choline ester | —NH₂ |
| 245 | methyl-H-phosphinate | —NH₂ |
| 246 | (S)-3-amino-4-hydroxy-2-butanone | —NH₂ |
| 247 | CH₃C(O)CH₂OCH₃ | —NH₂ |

TABLE I-continued
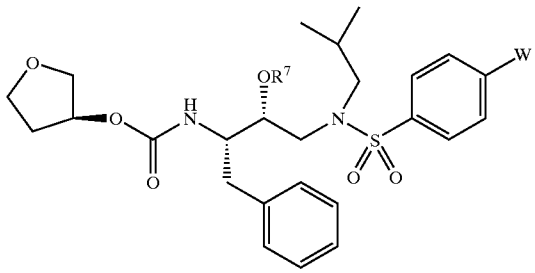
| CMPD | R⁷ | W |
|---|---|---|
| 248 | 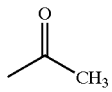 | —NH₂ |
| 249 |  | —NH₂ |
| 250 | 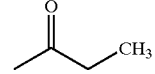 | —NH₂ |
| 251 |  | —NH₂ |
| 252 | 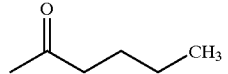 | —NH₂ |
| 253 |  | —NH₂ |
| 254 | 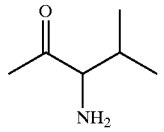 | —NH₂ |
| 255 | H | —NH—CHO |
| 256 | H |  |
| 257 | H | 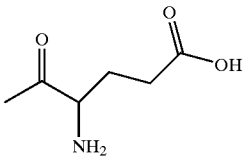 |

TABLE I-continued
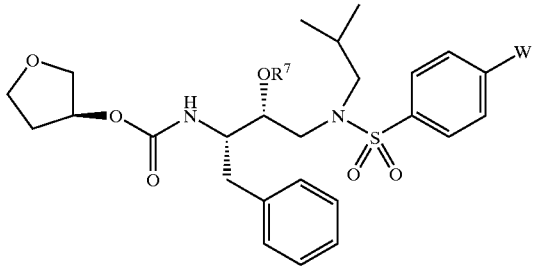
| CMPD | R⁷ | W |
| --- | --- | --- |
| 258 | H | 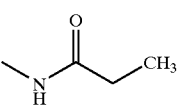 |
| 259 | H | 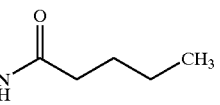 |
| 260 | H | 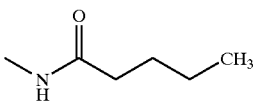 |
| 261 | 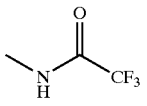 | 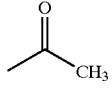 |
| 262 | 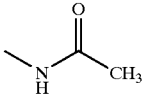 | 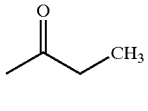 |
| 263 | 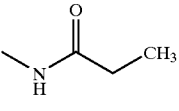 | 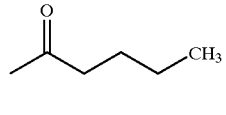 |
| 264 | PO₃K₂ | —NH₂ |
| 265 | PO₃Ca | —NH₂ |
| 266 | PO₃Mg | —NH₂ |
| 267 | 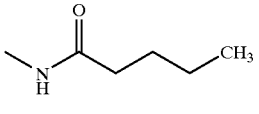 | —NH₂ |
| 308 | 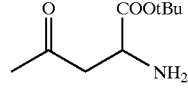 | —NH₂ |

TABLE I-continued

| CMPD | R⁷ | W |
|---|---|---|
| 402 | H | (structure: N-methylamide of ornithine with NHBoc on α-carbon and terminal NH₂) |
| 403 | H | (structure: N-methylamide of lysine with NHBoc on α-carbon and terminal NH₂) |
| 404 | H | (structure: N-methylamide of arginine with NHBoc on α-carbon) |
| 405 | H | (structure: N-methylamide of ornithine with NHAc on α-carbon and terminal NH₂) |
| 406 | H | (structure: N-methylamide of lysine with NHAc on α-carbon and terminal NH₂) |
| 407 | H | (structure: N-methylamide of arginine with NHAc on α-carbon) |
| 408 | $H_3C-P(=O)(OH)-$ (methylphosphonic acid group) | —NH₂ |

TABLE II
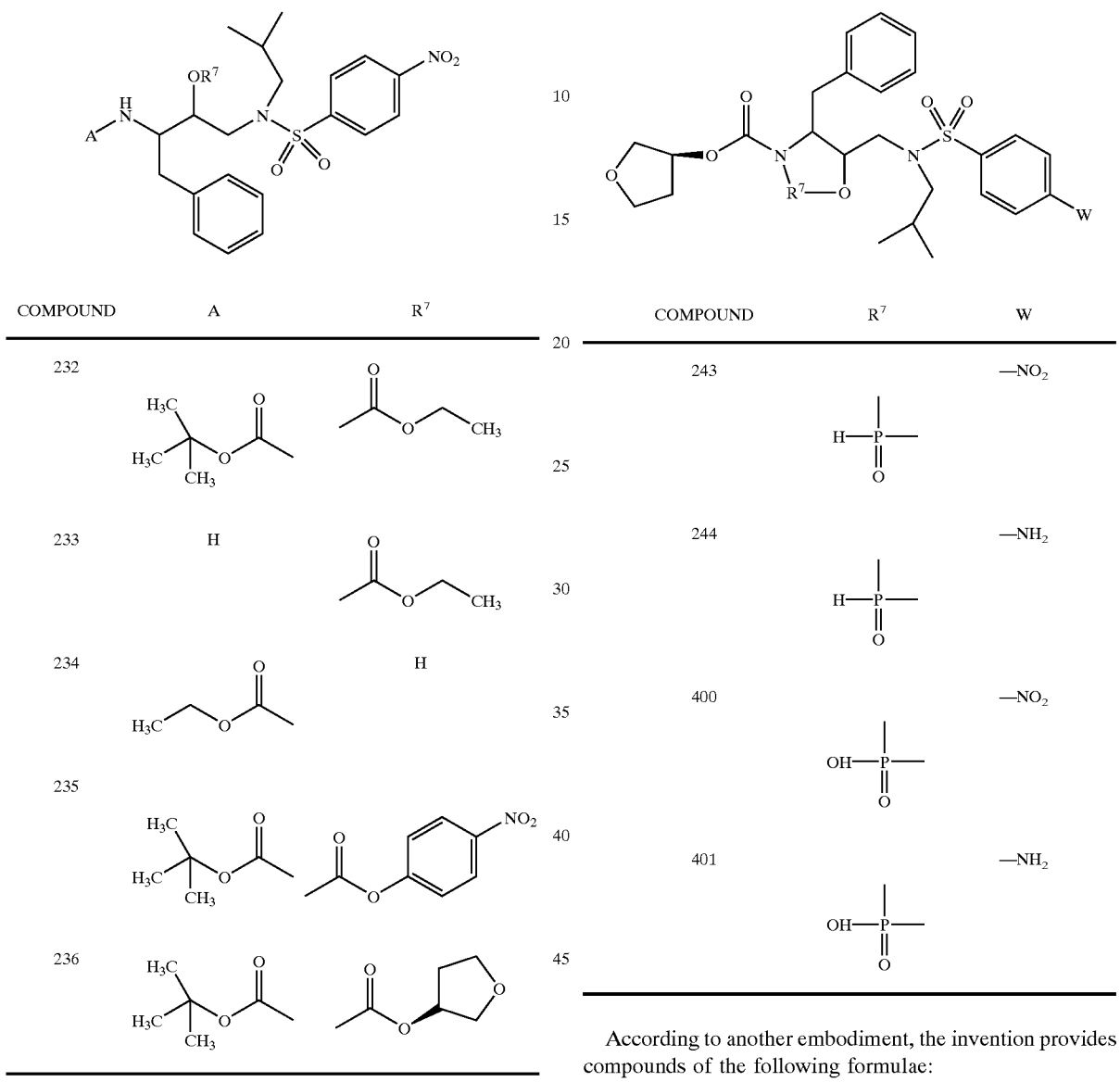
TABLE III
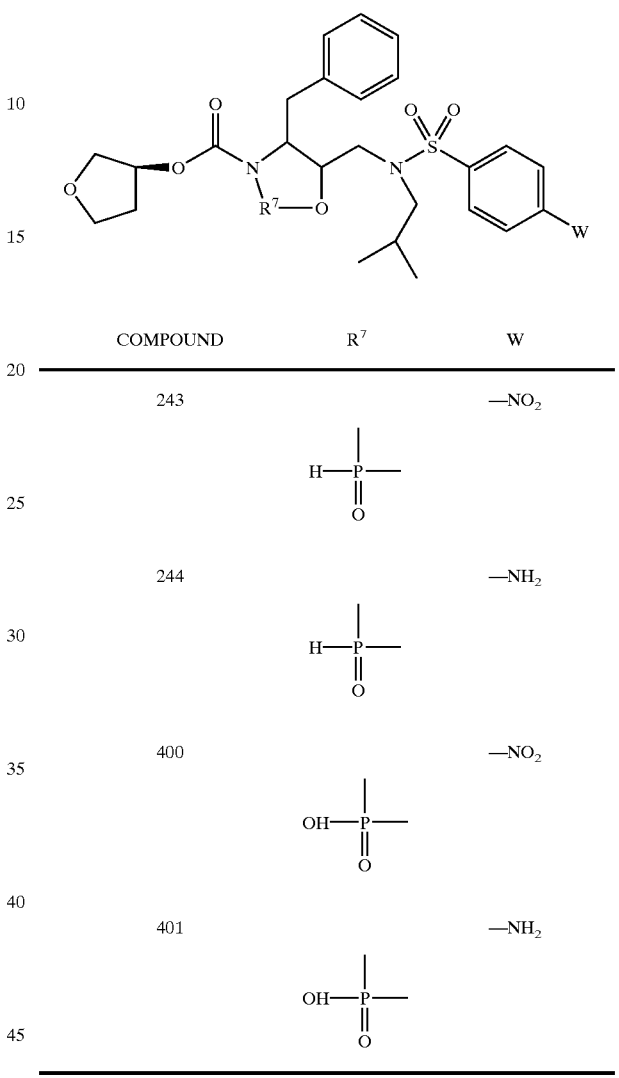
According to another embodiment, the invention provides compounds of the following formulae:
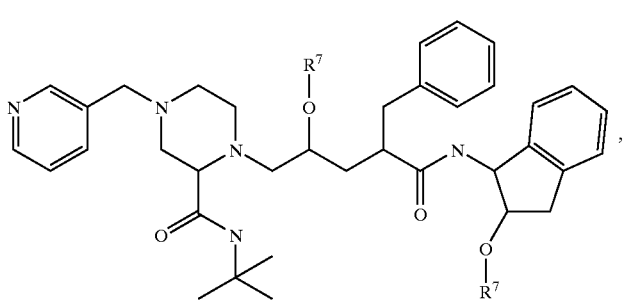

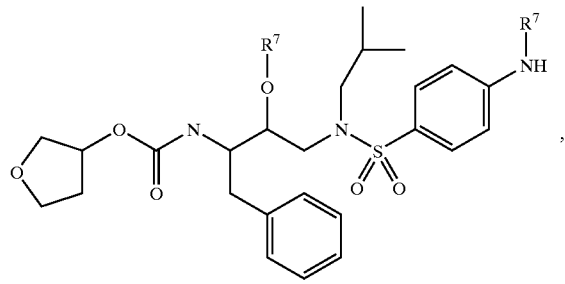
1002
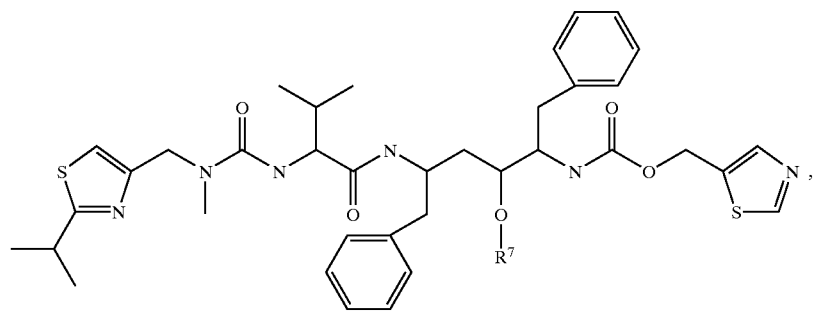
1003
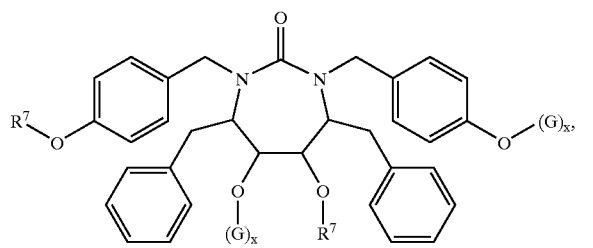
1004
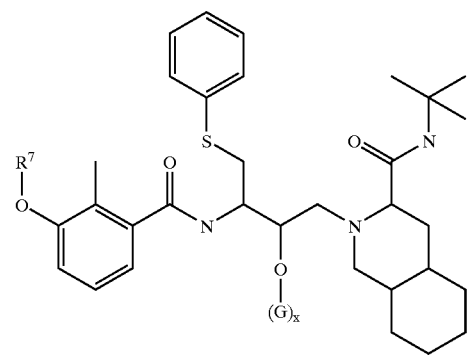
1005
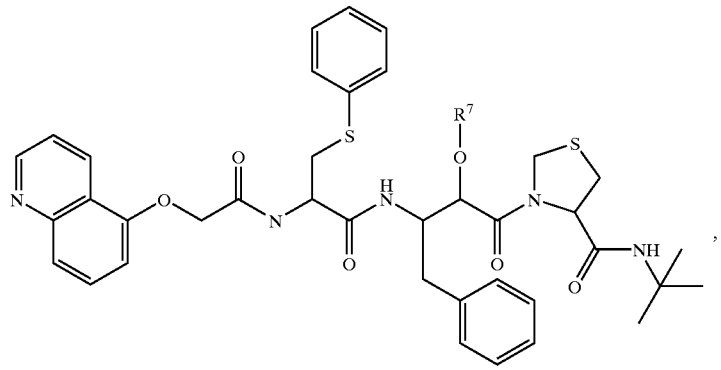
1006

-continued

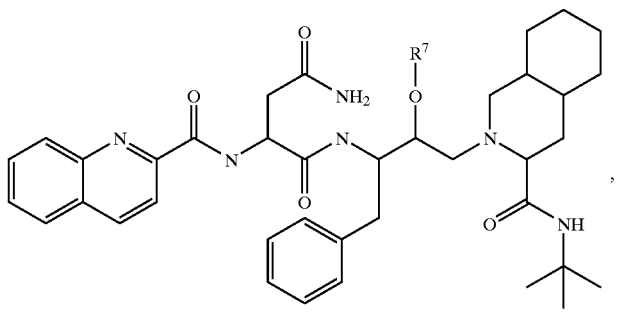
1007

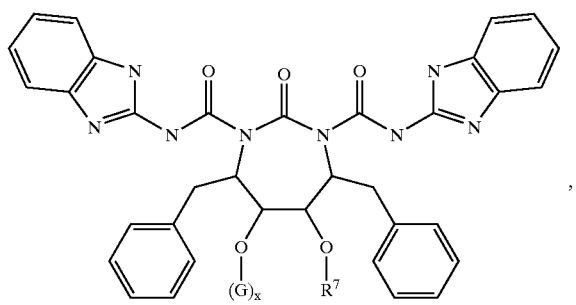
1008

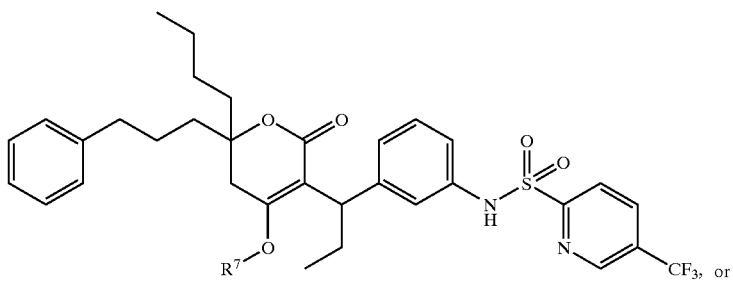
1009, or

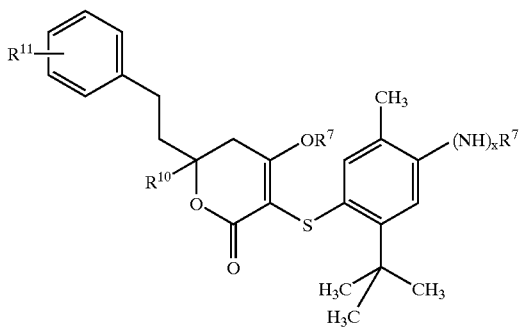
1010 wherein, in compound 1005, when $R^7$ is $PO_3M$, $(G)_x$ is not H; and wherein $R^{10}$ is selected from isopropoyl or cyclopentyl; $R^{11}$ is selected from $NHR^7$ or $OR^7$; and x, $R^7$ and G are as defined above.

The prodrugs of the present invention may be synthesized using conventional synthetic techniques. U.S. Pat. No. 5,585,397 discloses the synthesis of compounds of formula:

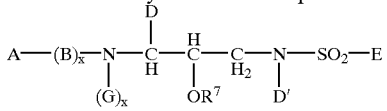

wherein A, B, n, D, D', and E are as defined above. Prodrugs of formula (I) of the present invention can be readily synthesized from the '397 compounds using conventional techniques. One of skill in the art would be well aware of conventional synthetic reagents to convert the —OH group of the '397 compounds to a desired —$OR^7$ functionality of the present invention, wherein $R^7$ is as defined above. The relative ease with which the compounds of this invention can be synthesized represents an enormous advantage in the large scale production of these compounds.

For example, VX-478, a compound disclosed in the '397 patent, can be readily converted to the corresponding bis-phosphate ester derivative, as shown below:

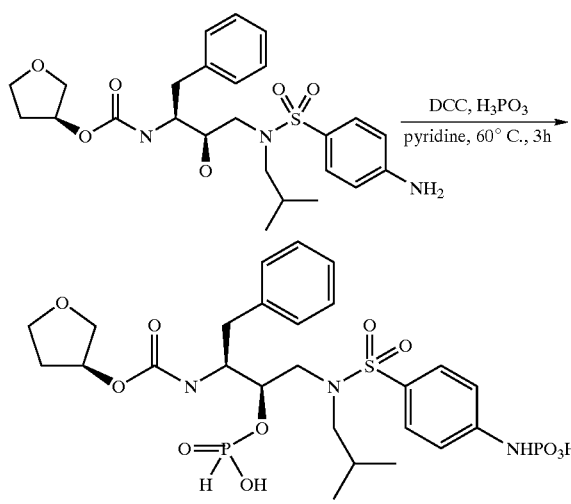

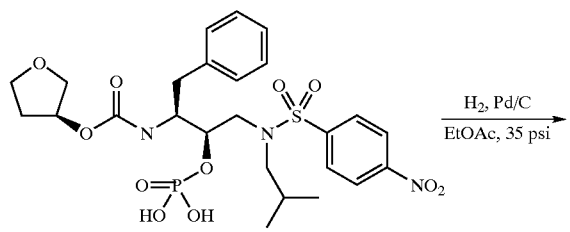

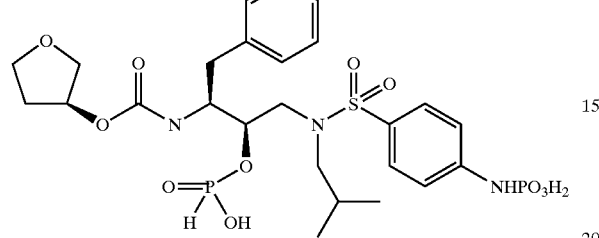

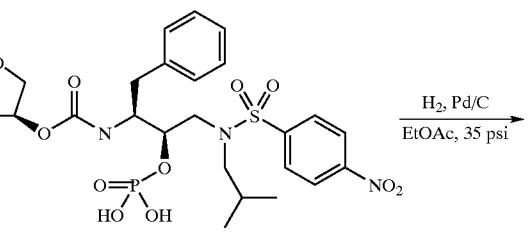

Alternatively, if the monophosphate ester of VX-478 is desired, then the synthetic scheme can be readily adapted by beginning with the 4-nitrophenyl derivative of VX-478, as shown below:

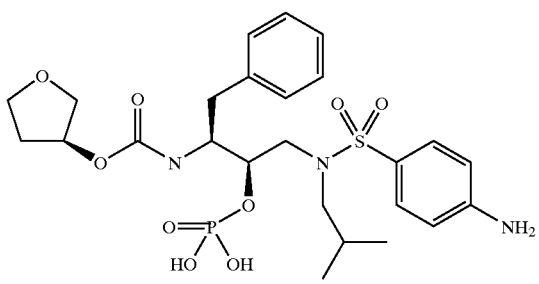

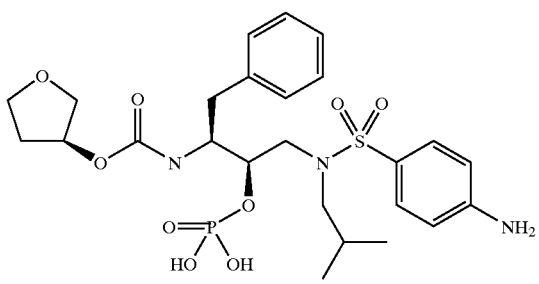

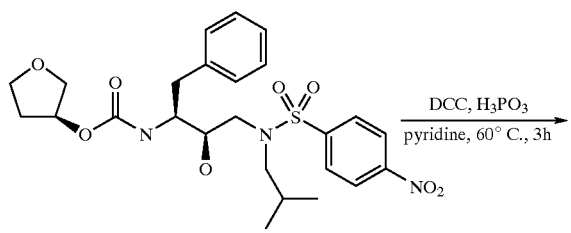

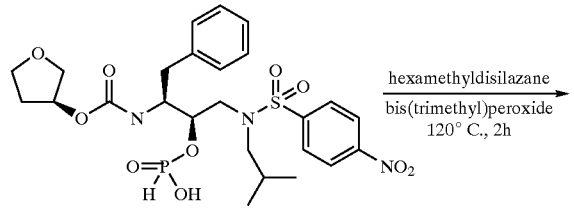

Examples of specific compounds in addition to VX-478 which may be converted to the prodrugs of this invention by similar techniques (and the syntheses of those intermediates to the compounds of the present invention) are disclosed in WO 94/05639 and WO 96/33184, the disclosures of which are herein incorporated by reference.

Pharmaceutically acceptable salts of the compounds of the present invention may be readily prepared using known techniques. For example, the disodium salt of the monophosphate ester shown above can be prepared as shown below:

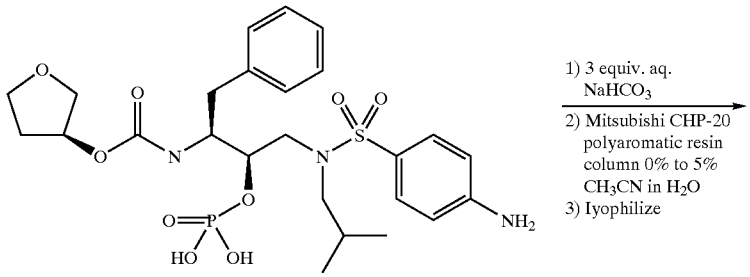

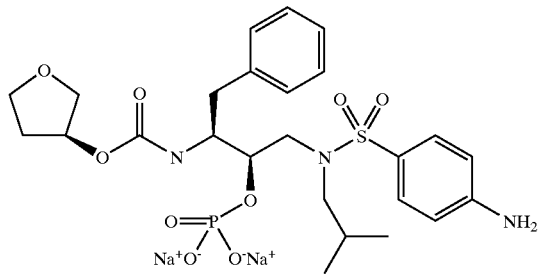

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Without being bound by theory, we believe that two different mechanisms are involved in converting the prodrugs of this invention into the active drug, depending upon the structure of the prodrug. The first mechanism involves the enzymatic or chemical transformation of the prodrug species into the active form. The second mechanism involves the enzymatic or chemical cleavage of a functionality on the prodrug to produce the active compound.

The chemical or enzymatic transformation can involve to transfer of a functional group (i.e., $R^7$) from one heteroatom within the molecule to another heteroatom. This transfer is demonstrated in the chemical reactions shown below:

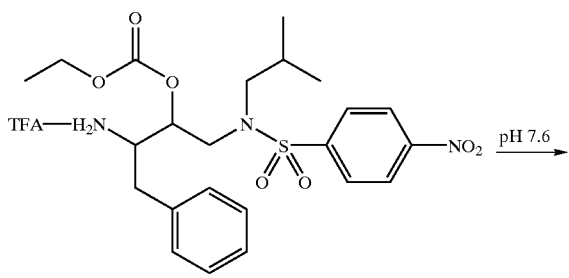

and

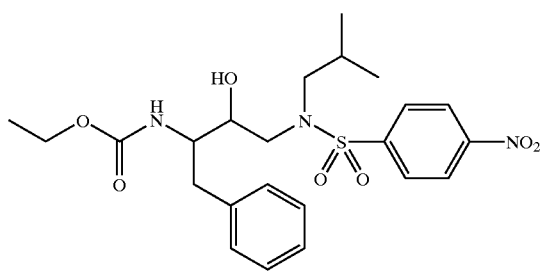

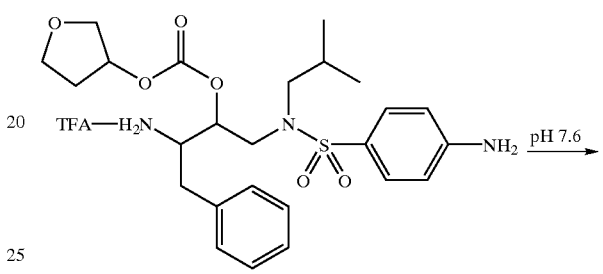

The cleavage mechanism is demonstrated by the reaction below where a phosphate ester-containing prodrug is converted into the active form of the drug by removal of the phosphate group.

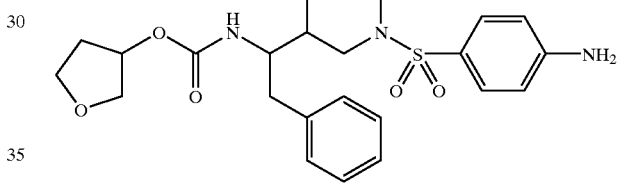

These protease inhibitors and their utility as inhibitors of aspartyl proteases are described in U.S. Pat. No. 5,585,397, the disclosure of which is incorporated herein by reference.

The prodrugs of the present invention are characterized by unexpectedly high aqueous solubility. This solubility facilitates administration of higher doses of the prodrug, resulting in a greater drug load per unit dosage. The prodrugs of the present invention are also characterized by facile hydrolytic cleavage to release the active aspartyl protease inhibitor in vivo. The high aqueous solubility and the facile in vivo metabolism result in a greater bioavailability of the drug. As a result, the pill burden on a patient is significantly reduced.

The prodrugs of this invention may be employed in a conventional manner for the treatment of viruses, such as HIV and HTLV, which depend on aspartyl proteases for obligatory events in their life cycle. Such methods of treatment, their dosage levels and requirements may be selected by those of ordinary skill in the art from available methods and techniques. For example, a prodrug of this invention may be combined with a pharmaceutically acceptable adjuvant for administration to a virally-infected patient in a pharmaceutically acceptable manner and in an amount effective to lessen the severity of the viral infection.

Alternatively, the prodrugs of this invention may be used in vaccines and methods for protecting individuals against viral infection over an extended period of time. The prodrugs may be employed in such vaccines either alone or together with other compounds of this invention in a manner consistent with the conventional utilization of protease inhibitors in vaccines. For example, a prodrug of this invention may be combined with pharmaceutically acceptable adjuvants conventionally employed in vaccines and administered in prophylactically effective amounts to protect individuals over an extended period time against HIV infection. As such, the novel protease inhibitors of this invention can be administered as agents for treating or preventing HIV infection in a mammal.

The prodrugs of this invention may be administered to a healthy or HIV-infected patient either as a single agent or in combination with other anti-viral agents which interfere with the replication cycle of HIV. By administering the compounds of this invention with other anti-viral agents which target different events in the viral life cycle, the therapeutic effect of these compounds is potentiated. For instance, the co-administered anti-viral agent can be one which targets early events in the life cycle of the virus, such as cell entry, reverse transcription and viral DNA integration into cellular DNA. Anti-HIV agents targeting such early life cycle events include, didanosine (ddI), alcitabine (ddC), d4T, zidovudine (AZT), polysulfated polysaccharides, sT4 (soluble CD4), ganiclovir, dideoxycytidine, trisodium phosphonoformate, eflor-nithine, ribavirin, acyclovir, alpha interferon and tri-menotrexate. Additionally, non-nucleoside inhibitors of reverse transcriptase, such as TIBO or nevirapine, may be used to potentiate the effect of the compounds of this invention, as may viral uncoating inhibitors, inhibitors of trans-activating proteins such as tat or rev, or inhibitors of the viral integrase.

Combination therapies according to this invention exert a synergistic effect in inhibiting HIV replication because each component agent of the combination acts on a different site of HIV replication. The use of such combinations also advantageously reduces the dosage of a given conventional anti-retroviral agent which would be required for a desired therapeutic or prophylactic effect as compared to when that agent is administered as a monotherapy. These combinations may reduce or eliminate the side effects of conventional single anti-retroviral agent therapies while not interfering with the anti-retroviral activity of those agents. These combinations reduce potential of resistance to single agent therapies, while minimizing any associated toxicity. These combinations may also increase the efficacy of the conventional agent without increasing the associated toxicity. In particular, we have discovered that these prodrugs act synergistically in preventing the replication of HIV in human T cells. Preferred combination therapies include the administration of a prodrug of this invention with AZT, ddI, ddC or d4T.

Alternatively, the prodrugs of this invention may also be co-administered with other HIV protease inhibitors such as Ro 31-8959 (Roche), L-735,524 (Merck), XM 323 (Du-Pont Merck) and A-80,987 (Abbott) to increase the effect of therapy or prophylaxis against various viral mutants or members of other HIV quasi species.

We prefer administering the prodrugs of this invention as single agents or in combination with retroviral reverse transcriptase inhibitors, such as derivatives of AZT, or other HIV aspartyl protease inhibitors. We believe that the co-administration of the compounds of this invention with retroviral reverse transcriptase inhibitors or HIV aspartyl protease inhibitors may exert a substantial synergistic effect, thereby preventing, substantially reducing, or completely eliminating viral infectivity and its associated symptoms.

The prodrugs of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO); and antibiotics (e.g., pentamidine isethiorate) to prevent or combat infection and disease associated with HIV infections, such as AIDS and ARC.

When the prodrugs of this invention are administered in combination therapies with other agents, they may be administered sequentially or concurrently to the patient. Alternatively, pharmaceutical or prophylactic compositions according to this invention may be comprised of a combination of a prodrug of this invention and another therapeutic or prophylactic agent.

Although this invention focuses on the use of the prodrugs disclosed herein for preventing and treating HIV infection, the compounds of this invention can also be used as inhibitory agents for other viruses which depend on similar aspartyl proteases for obligatory events in their life cycle. These viruses include, as well as other AIDS-like diseases caused by retroviruses, such as simian immunodeficiency viruses, but are not limited to, HTLV-I and HTLV-II. In addition, the compounds of this invention may also be used to inhibit other aspartyl proteases, and in particular, other human aspartyl proteases, including renin and aspartyl proteases that process endothelin precursors.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 50 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

In order that this invention be more fully understood, the following examples are set forth. These examples are for the purpose of illustration only and are not to be construed as limiting the scope of the invention in any way.

EXAMPLE 1

General Conditions (A) Analytical HPLC 0–100%B/30 min, 1.5 mL/min, A=0.1% TFA in water, B=0.1% TFA in acetonitrile. Detection at 254 and 220 nm, C18 reverse phase Vydac, t0=2.4 min.

(B) 1/3 v/v EtOAc/hexane (C) 1/2 v/v EtOAc/hexane (D) Analytical HPLC 0–100%B/10 mn , 1.5 mL/min, A=0.1% TFA in water, B=0.1% TFA in acetonitrile. Detection at 254 and 220 nm, C18 reverse phase Vydac, $t_0$=2.4 min.

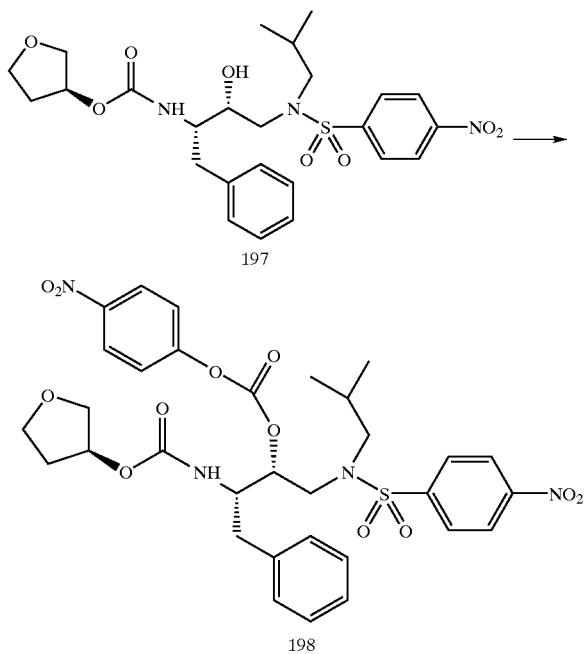

A mixture of 2.0 g (3.7 mMol) of 197 and 3.0 g (16 mMol) of di-p-nitrophenyl carbonate in 10 ml of dimethylformamide was treated at 25° with 4 ml (4 mMol) of P4-phosphazene base (Fluka, 1M in hexane). The mixture was stirred for 6 h at 25° until all of the starting alcohol was consumed. The reaction mixture was partitioned between ethyl acetate and 1N hydrochloric acid. The organic layer was washed with 1N sodium hydroxide and brine, dried over magnesium sulfate and concentrated in vacuo. Titration with dichloromethane gave the desired mixed carbonate (1.2 g crop1 and 0.6 g crop 2) as a fine powder. Combined yield: 69%. Rf=0.13 (1/3 EtOAc/hexane, conditions B), Rf=0.40 (1/2 EtOAc/hexane, conditions C), tHPLC=23.83 min (A), MS(ES+) 701 (M+1).

1H-NMR (CDCl3): 0.82 (6H,dd), 1.9 (2H,m), 2.15 (1H, m), 2.8 (1H,m), 3.0 (4H,m), 3.5 (2H,m), 3.6 (1H,m), 3.8 (4H,m), 4.3 (1H,bs), 4.8 (1H,m), 5.17 (2H,m), 7.7 (7H,m), 7.95 (2H,d), 8.35 (4H,m)

13C (CDCl3): 155.2 152.2, 149.9, 145.6, 135.9, +129.0, +128.8, +128.5, +127.2, +125.4, +124.4, +121.8, +78.1, +75.8, −73.1, −66.9, −56.5, +52.7, −48.2, −35.9, −35.9, 32.6, −26.4, +19.9, +19.8.

EXAMPLE 2

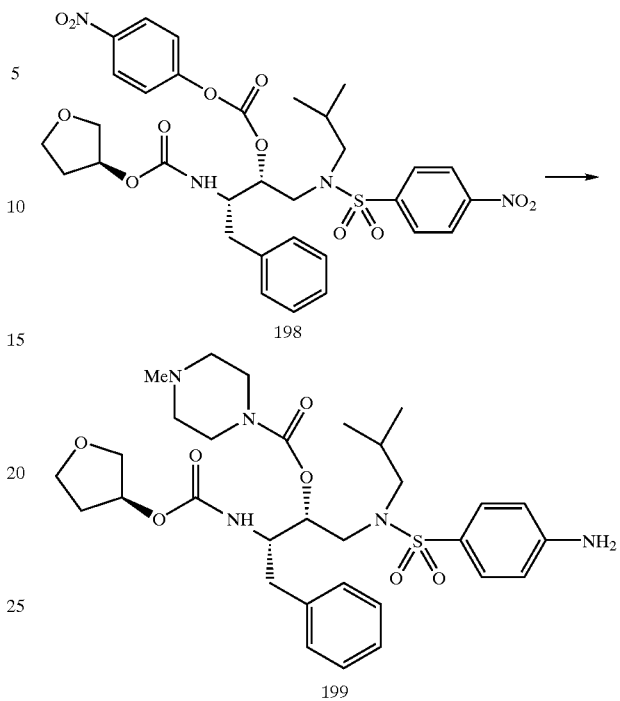

To 0.20 g (0.286 mM) of 198 dissolved in 3 ml of THF was added 0.11 g (1.14 mM) of 1-Methyl-piperidine and the mixture was stirred overnight at room temperature ("rt"). All the solvents were then evaporated and the solid residue partitioned between EtOAc and water. The volatiles were removed and, where appropriate, the residue was treated with 1:1 TFA/DCM over 30 min at rt to remove the Boc protecting group. The product was dissolved in 0.25 ml TFA and 1.5 ml THF. Hydrogenolysis for 10 hours in presence of 30 mg of 10% Pd/C gave the desired compound. The final purification was on preparative reversed phase C18 using conditions Example 1, except that the flow rate was 18 ml/min.

C,H,N: calc: 49.27, 5.57, 8.25, found 49.15, 5.76, 8.29 $C_{31}H_{45}N_5O_7S_1 \cdot 1.9CF_3COOH$ LC/MS (ES+) 632 (M+1) 1 peak at 4.71 min Analytical HPLC(A) t=N/A min 1H:0.71 (3H,d), 0.74 (3H,d), 1.80 (2H,m), 2.03 (1H,m), 2.63 (2H,m), 2.74 (1H,m), 2.82 (3H,s), 2.92 (2H,m), 3.20 (4H,m), 3.42 (3H,m), 3.62 (2H,m), 3.75 (1H,m), 4.05 (3H, m), 4.97 (2H,m), 6.2 (1H,bs), 6.60 (2H,m), 7.22 (5H,m), 7.40 (3H,m), 13C (DMSO): 156.4, 154.0, 153.8, 138.8, 129.6, 129.5, 128.3, 126.5, 123.7, 112.7, 74.8, 72.9, 66.7, 58.2, 54.0, 53.1, 49.3, 42.3, 40.8, 36.0, 33.3, 25.8, 20.4, 20.3

EXAMPLE 3

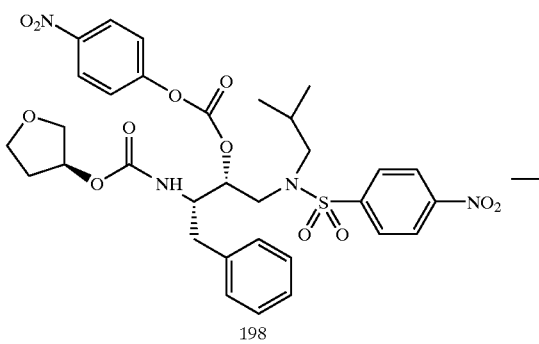

198

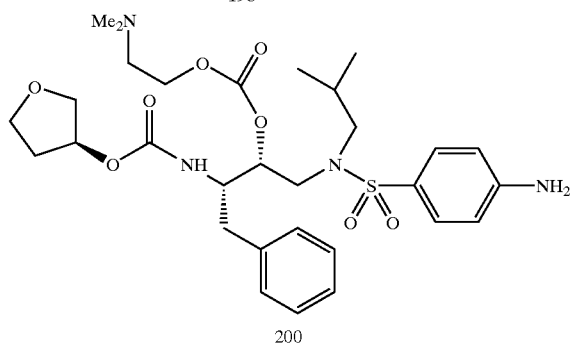

200

The synthesis of compound 200 from compound 198 was carried as described in Example 1, except that N,N-dimethyl-aminoethanol was used in place of di-p-nitrophenyl carbonate.

1HNMR (acetone-d6): 0.82 (6H,dd), 1.83 (2H,m), 2.07 (1H,m), 2.64 (2H,m), 2.82 (6H,s), 2.90 (2H,m), 3.19 (1H,m), 3.38 (4H,m), 3.63 (2H,m), 3.76 (1H,m), 4.17 (2YH,m), 4.40 (1H,m), 4.56 (1H,m), 4.96 (1H,m), 5.06 (1H,m), 6.06 (1H,d), 6.68 (2H,d), 7.23 (5H,m), 7.47 (2H,d).

13CNMR (acetone d6): 20.2, 20.3, 27.5, 33.4, 35.6, 43.8, 50.1, 54.2, 56.4, 58.5, 63.1, 67.4, 73.6, 76.2, 79.9, 114.2, 118.3, 127.4, 129,2, 130.1, 130.3, 139.3, 153.4, 157.0.

LC/MS: 1 peak, 621 (MH+).

EXAMPLE 4

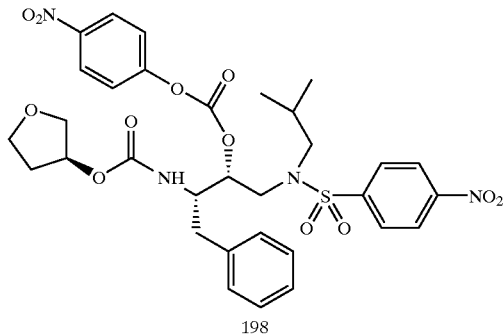

198

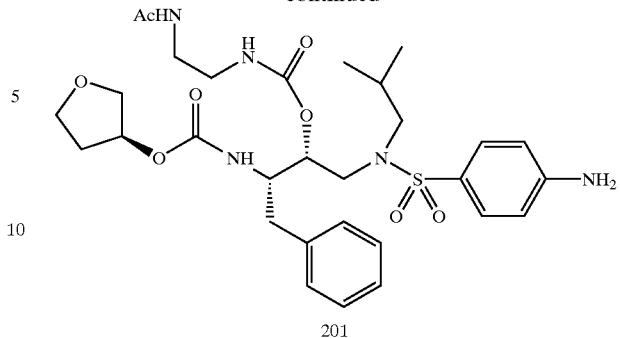

201

The synthesis of compound 201 from compound 198 was carried as described in Example 1, except that N-acetyl-ethylenediamine was used in place of di-p-nitrophenyl carbonate.

C,H,N: calc: 49.66, 5.64, 8.83, found 49.76, 5.98, 8.93 $C_{30}H_{43}N_5O_8S_1.1.4CF_3COOH$.

LC/MS (ES+) 634 (M+1) 1 peak at 5.08 min.

Analytical HPLC(A) t=15.92 min.

1H: d-3 acetonitrile: 0.88 (6H,dd), 1.92 (3H,s), 1.94 (2H,m), 2.17 (1H,m), 2.72 (2H,m), 2.96 (2H,m), 3.07 (3H,m), 3.29 (1H,m), 3.42 (3H,m), 3.69 (1H,m), 3.77 (1H,m), 3.82 (1H,m), 4.133 (1H,m), 4.40 (1H,bs), 5.05 (2H,m), 5.80 (1H,m), 6.10 (1H,d), 6.78 (2H,d), 6.83 (1H,bs), 7.28 (5H,m), 7.58 (2H,d).

13C (d3-acetonitrile): 157.1, 157.0, 153.2, 139.6,+130.3, +130.2, +129.2, +127.2, 126.2, +114.2, +76.0, +75.4, −73.6, −67.4, −58.2, +54.9, −50.2, −41.6, −39.8, −35.9, −33.4, +27.3, +23.1, +20.4, +20.2.

EXAMPLE 5

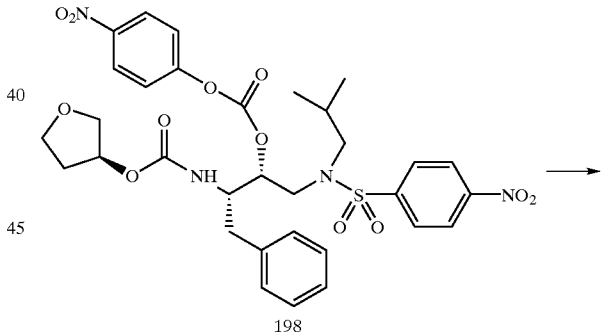

198

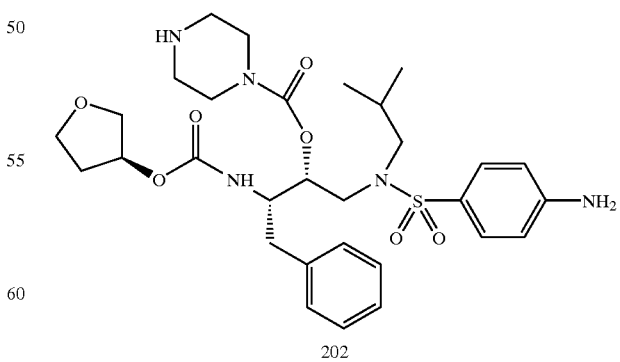

202

The synthesis of compound 202 from compound 198 was carried as described in Example 1, except that mono N-Boc-piperazine was used in place of di-p-nitrophenyl carbonate.

C,H,N: calc: 48.28, 5.68, 8.41, found 48.28, 5.36, 8.28 C$_{30}$H$_{43}$N$_5$O$_7$S$_1$×2 CF$_3$COOH LC/MS (ES+) 618 (M+1) 1 peak at 4.36 min.

Analytical HPLC(A) t=14.84 min.

1H: d6-DMSO: 0.72 (3H,d), 0.77 (3H,d), 1.78 (2H,m), 2.09 (1H,m), 2.64 (2H,m), 2.73 (1H,m), 2.80 (1H,m), 3.08 (4H,m), 3.32 (2H,m), 3.41 (1H,m), 3.50 (4H,m), 3.54 (1H,m), 3.63 (1H,m), 3.70 (1H,m), 3.98 (1H,m), 4.89 (1H,m), 4.97 (1H,m), 6.61 (2H,d), 7.23 (5H,m), 7.42 (3H,m), 8.88 (2H,bs).

13C: (DMSO): 155.7, 153.6, 153.0, 138.4, +129.1, +129.0, +128.1, +126.1, 123.2, +112.7, +75.2, +74.4, −72.5, −66.2, −56.9, +53.1, −48.8, −42.5, −40.8, −35.0, −32.2, +26.2, +20.0, +19.8.

EXAMPLE 6

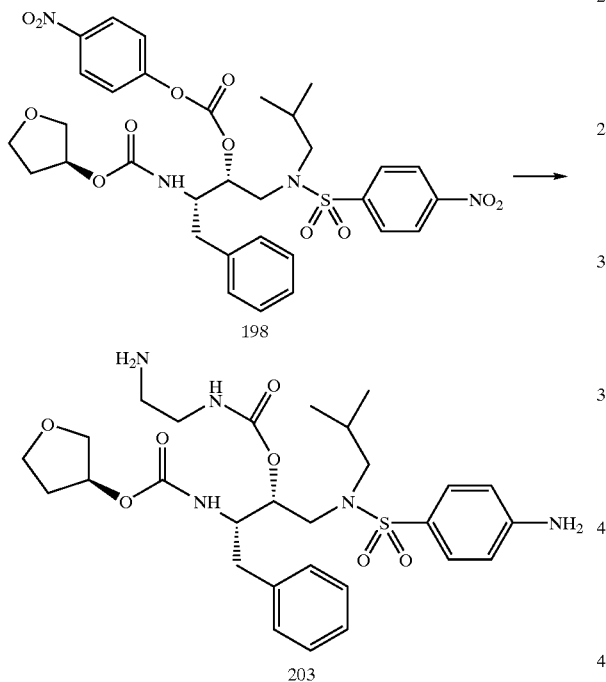

The synthesis of compound 203 from compound 198 was carried as described in Example 1, except that mono-N-Boc-ethylenediamine was used in place of di-p-nitrophenyl carbonate.

C,H,N: calc: 46.89, 5.29, 8.54, found 46.50, 5.51, 8.54 C$_{28}$H$_{41}$N$_5$O$_7$S$_1$×2 CF$_3$COOH.

LC/MS (ES+) 592 (M+1) 1 peak at 4.32 min.

Analytical HPLC(A) t=14.69 min.

1H:d-6 DMSO: 0.77 (6H,d), 1.82 (2H,m), 2.06 (1H,m), 2.57 (2H,m), 2.82 (4H,m), 2.97 (1H,m), 3.30 (5H,m), 3.55 (1H,m), 3.65 (1H,m), 3.70 (1H,m), 3.95 (1H,m), 4.88 (1H,m), 4.95 (1H,m), 6.62 (2H,d), 7.20 (6H,m), 7.39 (3H,m), 7.78 (3H,bs).

13C (dmso): 155.9, 152.9, 138.5, 129.2, 128.9, 128.1, 126.1, 122.9, 112.7, 74.7, 74.5, 72.6, 66.2, 57.2, 53.2, 49.4, 38.8, 37.94, 35.1, 32.1, 26.3, 20.0, 19.8.

EXAMPLE 7

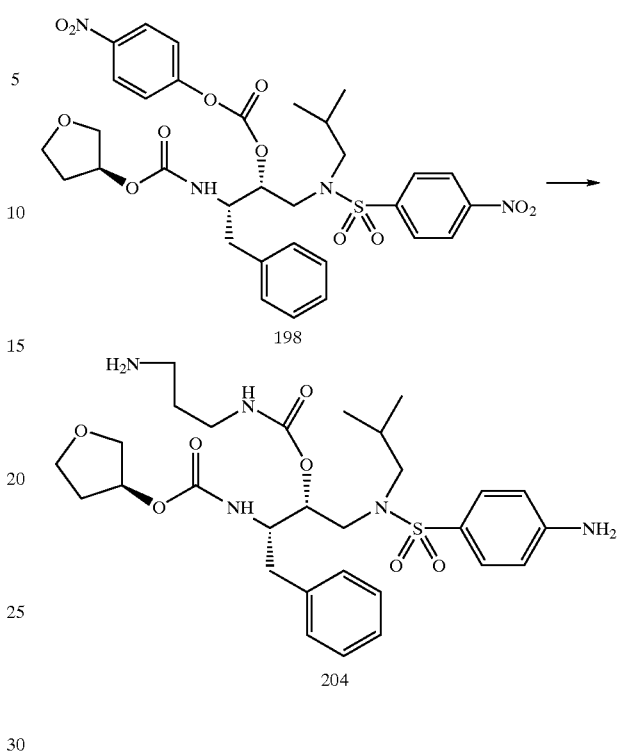

The synthesis of compound 204 from compound 198 was carried as described in Example 1, except that mono-1,3-diamino-3-N-Boc-propane was used in place of di-p-nitrophenyl carbonate.

C,H,N: calc: 49.07, 5.64, 8.89, found 48.95, 6.00, 8.92 C$_{29}$H$_{43}$N$_5$O$_7$S$_1$×1.6 CF$_3$COOH LC/MS (ES+) 605 (M+1) 1 peak at 4.27 min.

Analytical HPLC(A) t=14.72 min.

1H:d-6 DMSO: 0.78 (6H,dd), 1.64 (2H,m), 1.83 (2H,m), 2.03 (1H,m), 2.57 (1H,m), 2.78 (4H,m), 2.94 (1H,m), 3.03 (2H,m), 3.32 (2H,m), 3.58 (1H,m), 3.63 (1H,m), 3.73 (1H,m), 3.87 (1H,m), 4.84 (1H,m), 4.92 (1H,m), 6.61 (2H,d), 7.22 (6H,m), 7.36 (1H,d), 7.28 (2H,d), 7.76 (3H,ns).

13C (dmso): 155.8, 155.7, 138.5, +129.1, +129.0, +128.0, +126.1, 122.9, +112.7, +74.6, +74.3, −72.7, −66.2, −57.2, +53.6, −49.5, −37.4, −36.7, −35.5, −32.1, −27.6, +26.2, +20.0, +19.8.

EXAMPLE 8

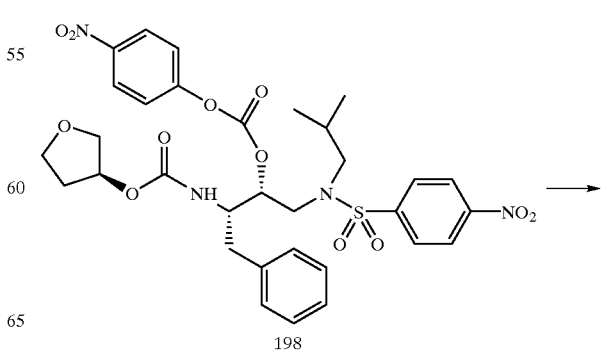

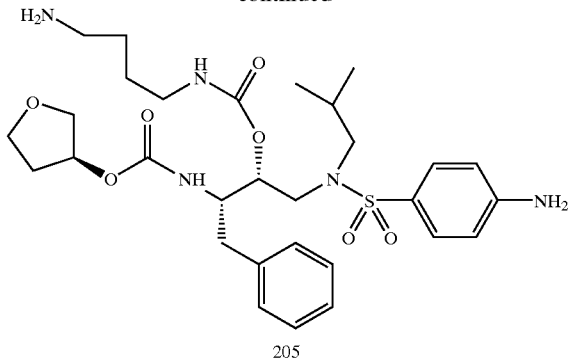

205

The synthesis of compound 205 from compound 198 was carried as described in Example 1, except that 1,4-diamino-4-N-Boc-butane was used in place of di-p-nitrophenyl carbonate.

C,H,N: calc: 48.17, 5.59, 8.26, found 48.02, 5.96, 8.24 $C_{30}H_{45}N_5O_7S_1$.2 $CF_3COOH$ LC/MS (ES+) 620 (M+1) 1 peak at 4.36 min.

Analytical HPLC(A) t=14.93 min.

1H: d-6 DMSO: 0.77 (6H,dd), 1.43 (4H,m), 1.82 (2H,m), 2.03 (1H,m), 2.77 (4H,m), 2.95 (3H,m), 3.31 (2H, m), 3.56 (1H,m), 3.63 (1H,m), 3.70 (1H,bq), 3.82 (1H,m), 4.85 (1H,m), 4.92 (1H,m), 6.62 (2H,d), 7.2 (7H,m), 7.38 (2H,d), 7.72 (3H,bs).

13C: 155.7, 152.9, +138.6, +129.1, +129.0, +128.0, +126.1, +123.0, +112.7, +74.4, +74.3, −72.7, −66.2, −57.2, +53.7, −49.7, −38.6, −38.5, −35.4, −32.1, −26.3, +26.2, −24.4, +20.1, +19.9.

EXAMPLE 9

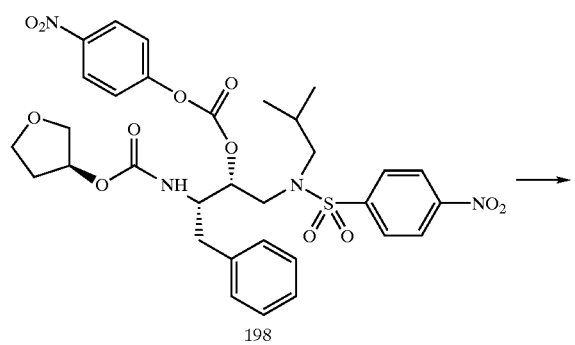

198

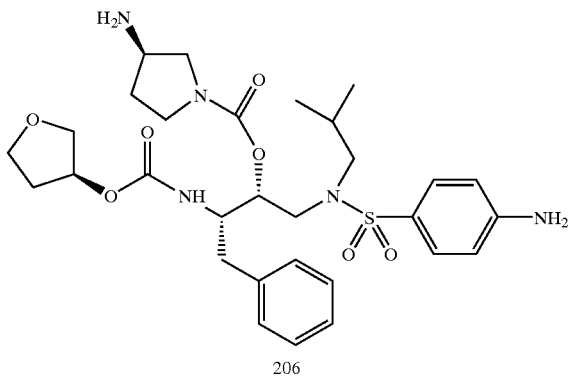

206

The synthesis of compound 206 from compound 198 was carried as described in Example 1, except that (3R)-(+)-3-Boc-aminopyrrolidine was used in place of di-p-nitrophenyl carbonate.

C,H,N: calc: 48.28, 5.36, 8.28, found 47.89, 5.53, 8.57 $C_{30}H_{43}N_5O_7S_1$×2 TFA LC/MS (ES+) 618 (M+1) 1 peak at 4.32 min.

Analytical HPLC(A) t=14.31 min.

1H and 13C NMR: complex and overlapping mixtures of rotomers.

EXAMPLE 10

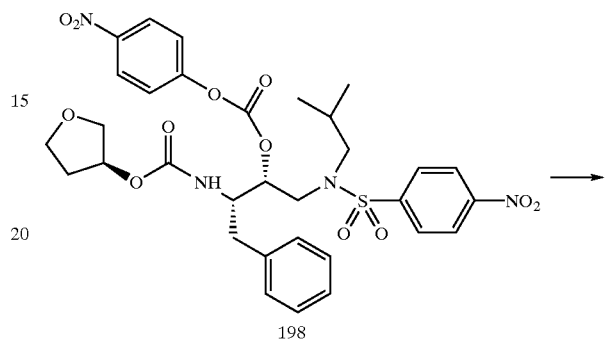

198

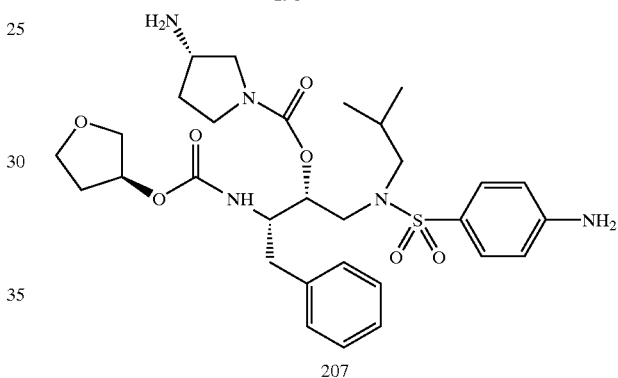

207

The synthesis of compound 207 from compound 198 was carried as described in Example 1, except that (3S)-(−)-3-Boc-aminopyrrolidine was used in place of di-p-nitrophenyl carbonate.

LC/MS (ES+) 618 (M+1) 1 peak at 4.19 min.

Analytical HPLC(A) t=14.75 min.

1H and 13C NMR: complex and overlapping mixtures of rotomers.

EXAMPLE 11

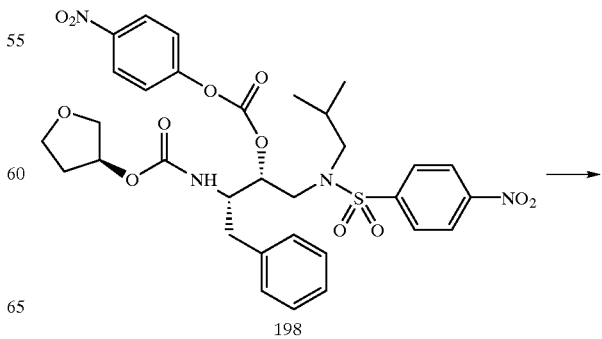

198

-continued

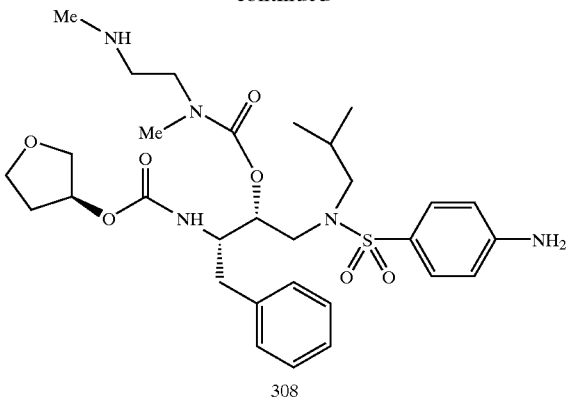

308

The synthesis of compound 308 from compound 198 was carried as described in Example 1, except that N-triphenylmethyl-N,N'-dimethylethanediamine was used in place of di-p-nitrophenyl carbonate.

1H-NMR: 0.76 (6H,dd), 1.65 (2H,m), 1.95 (1H,m), 2.07 (1H,m), 2.7 (2H,m), 2.75 (3H,s), 2.95 (3H,m), 3.45 (2H,m), 3.7 (4H,m), 4.2 (2H,bm), 5.05 (2H,bd), 6.62 (2H,d), 7.2 (5H,m), 7.5 (2H,d).

LC/MS: 1 peak, 620 (MH+).

EXAMPLE 12

General Procedures
Acylation

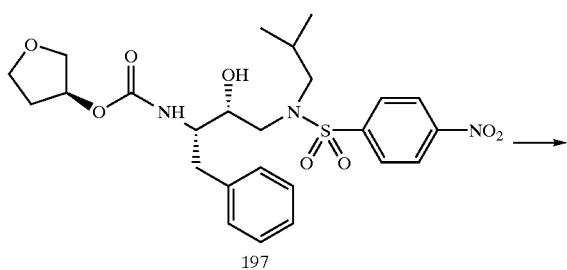

197

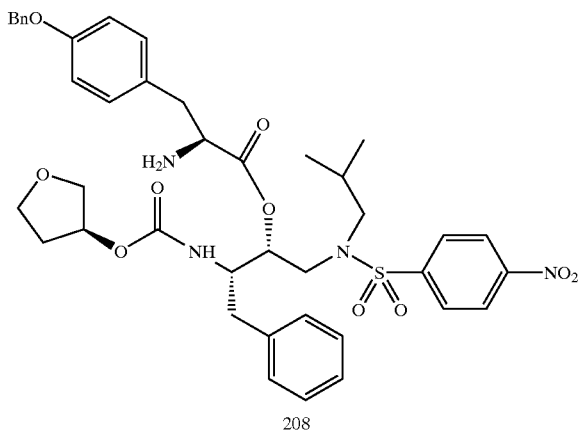

208

To 200 mg (0.37 mM) of 197 dissolved in 5 ml CH$_2$Cl$_2$ was added N-CBz-L-Benzyl tyrosine 183 mg (0.4 mM) followed by 231 mg (1.12 mM) DCC, followed by 29 mg (0.23 mM) DMAP. The reaction is stirred at rt for 24 hr. The precipitates present were removed by filtration. The filtrate was then concentrated in vacuo. The final compound was purified on preparative reversed phase C$_{18}$ using purification by HPLC C$_{18}$ Waters Delta Prep 3000 Column: YMC-Pack ODS AA 12S05-2520WT 250×20 mm I.D. S-5 mm, 120 Å, 0–100% B over ½ h, flow=18 ml/min, monitored at 220 nm, B=0.1% trifluoroacetic acid in acetonitrile, A=0.1% trifluoroacetic acid in water. Analytical Column: YMC-Pack ODS AA1 2S05-2520WT 250×4.6 mmI.D. S-5 mm, 120 Å, 0–100% B at 1.5 ml/min. over ½ h, monitored at 220 nm, B=0.1% trifluoroacetic acid in acetonitrile, A=0.1% trifluoroacetic acid in water.

The aqueous phase was lyophilized to give 59 mg, (16.3%) GW431896X, (U11484-72-10) t$_{HPLC}$=11.71 min., MW=966.04, LC/MS=MH+967.

Reduction of the Nitro Functionality

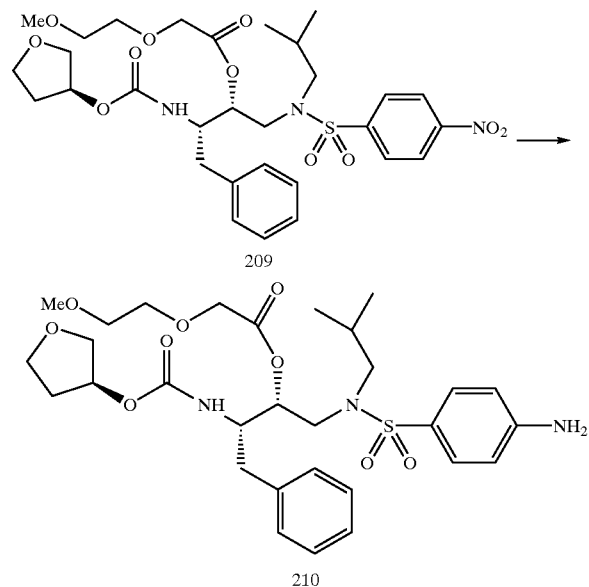

209

210

A slurry of 209 (170 mg) and 10 mg of 10% Pd.C in 95% EtOH was flushed with hydrogen in a scintillation vial equipped with septum and a stir bar. Continuous overnight hydrogenolysis under hydrogen balloon resulted in a complete conversion. The crude preparation was then filtered off the catalyst, and purified on RP C18 HPLC (Prep Nova-Pack C186 um, 60 A, gradient 0–100% B over 30 min. The desired product was collected and lyophilized affording a white fluffy solid (50 mg, 30.8%).

EXAMPLE 13

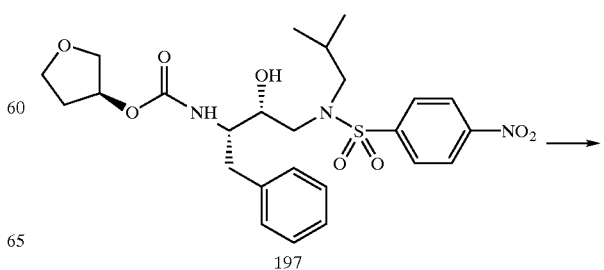

197

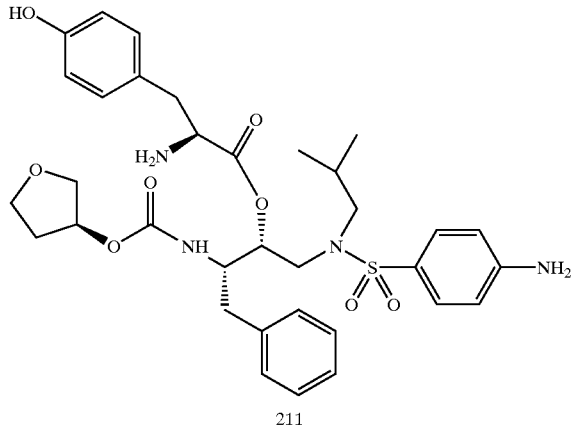

211

Compound 211 was obtained following the acylation and reduction procedures of Example 12.

ES+ 669.2 (M+1), tHPLC=8.06 min (D), 13C NMR (DMSO) 168.9, 156.9, 155.7, 153.1, 138.1, 130.5, 129.2, 129.1, 128.1, 126.2, 124.7, 122.5, 112.8, 76.2, 74.5, 72.5, 66.1, 58.0, 53.6, 52.6, 49.2, 33.6, 32.1, 26.6, 25.3, 20.0.

tHPLC=11.71 min (D), ES+ 967 (M+1).

EXAMPLE 14

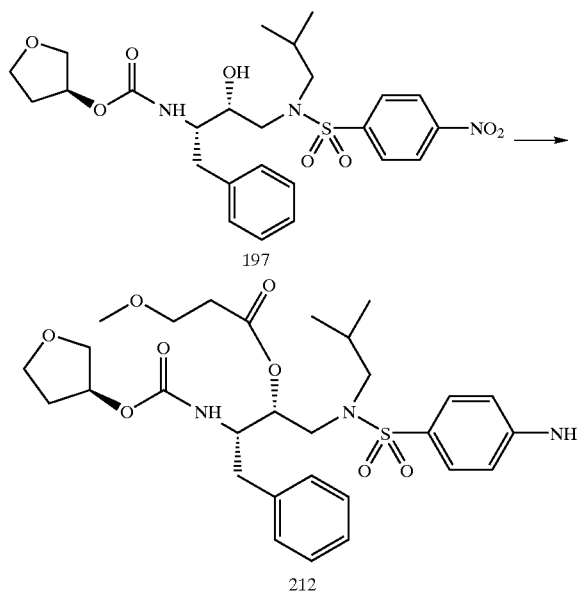

212

212 was obtained following the procedures of Example 12.

tHPLC=9.45 min (D), ES+ 592.2 (M+1).

13C NTMR (DMSO) 171.5, 155.8, 148.9, 137.8, 129.5, 129.3, 128.5, 126.7, 115.2, 75.2, 73.8, 73.1, 68.3, 67.0, 58.7, 57.1, 53.3, 49.2, 35.4, 32.4, 26.7, 20.1, 19.8.

1H(CDCl3, 399.42 KHz): 8.33 (2H, d, J=8.8), 7.95 (2H, d, J=8.8), 7.23 (5H, m) 5.22 (m, 2H), 5.08 (m, 1H), 4.08 (m, 1H), 3.80–3.45 (7H, m), 3.41 (3H, s), 2.98 (m, 3H), 2.66 (m, 1H), 2.57 (m, 2H), 2.10 (s, 1H), 1.93 (2H, m), 0.82 (3H, d), 0.78 (3H, d).

ES+ 622 (M+1), 644 (M+Na)
tHPLC=10.29 min (D).

13C NMR (CDCl3): 171.3, 155.5, 149.9, 145.6, 136.9, 129.2, 128.6, 128.5, 126.8, 124.4, 76.7, 75.3, 73.2, 72.9, 68.2, 66.9, 58.7, 55.9, 53.1, 48.3, 35.3, 32.7, 26.3, 19.9, 19.8.

EXAMPLE 15

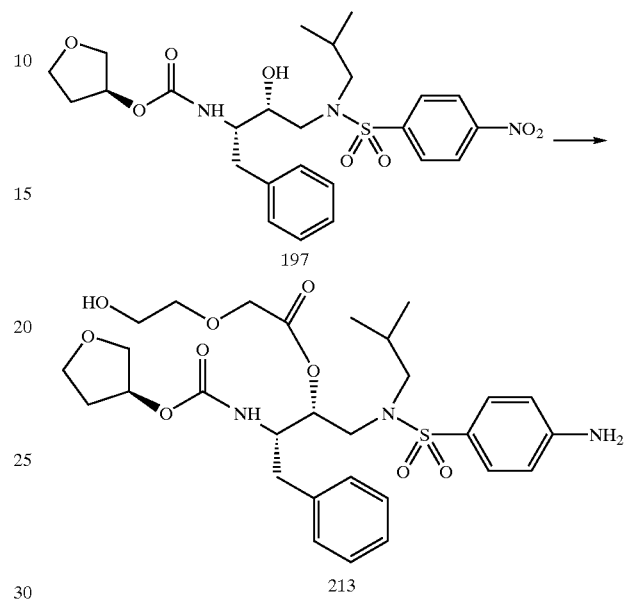

213

Compound 213 was obtained following the procedure of Example 12. tHPLC=9.21 min (D); ES+ 622 (M+1).

13C NMR (CDCl3): 170.54, 156.2, 148.6, 136.8, 129.4, 129.2, 128.6, 126.6, 115.7, 76.7, 74.6, 73.2, 71.8, 70.6, 68.2, 66.9, 58.9, 57.3, 53.8, 49.4, 36.2, 33.1, 26.8, 19.8, 19.5.

Intermediate: t HPLC=10.05 min (D); ES+=652 (M+H) 674 (M+Na).

EXAMPLE 16

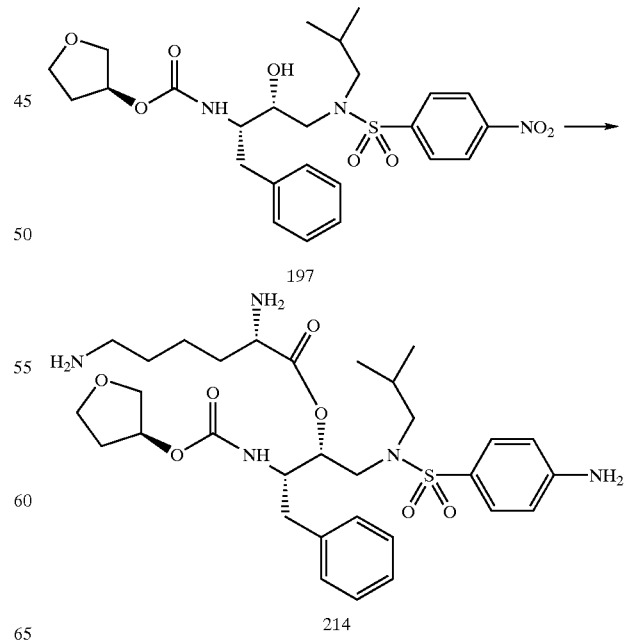

214

214 was obtained following the procedure of Example 12.

ES+ 634.4 (M+1); t HPLC=7.17 min (D).

13C (DMSO): 169.3, 155.8, 153.1, 138.0, 129.1, 129.0, 128.1, 126.3, 122.6, 112.8, 94.3, 75.6, 74.6, 72.4, 66.1, 57.8, 52.7, 52.0, 49.3, 38.4, 34.7, 32.2, 29.1, 26.6, 21.4, 20.1, 20.0.

EXAMPLE 17

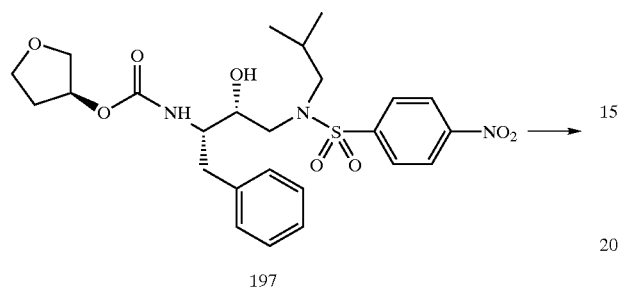

197

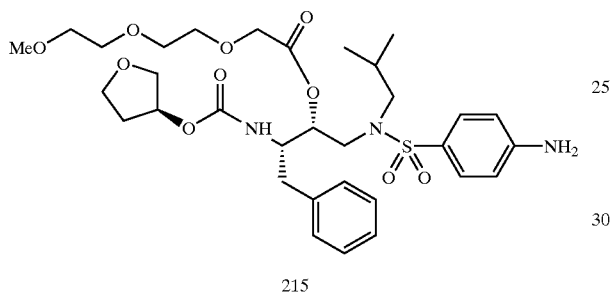

215

215 was obtained following the procedure of Example 12.

t HPLC=9.12 min (D)

1H (DMSO) all signals broad: 7.38 (3H, br m), 7.20 (5H, br m), 6.62 (2H, br m), 5.15 (1H, br m), 4.92 (1H, br m), 4.00 (3H, m), 3.7–3.0 (16H, m), 2.78 (2H, °), 2.57 (3H, m), 2.04 (m, 1H), 1.78 (m, 2H), 0.77 (6H, m)

13C (DMSO) 170.6, 156.3, 153.7, 139.1, 129.8, 128.4, 126.7, 123.7, 113.3, 79.8, 79.2, 77.3, 76.1, 75.4, 75.2, 73.0, 71.9, 52.3, 51.8, 48.2, 46.7, 39.9, 38.7, 25.8, 22.6.

Intermediate:

t HPLC=10.18 min (D); ES+ 696.3 (M+1).

EXAMPLE 18

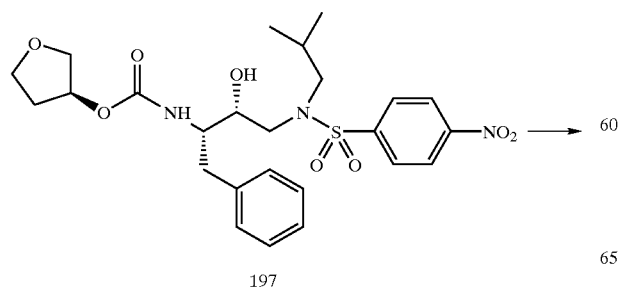

197

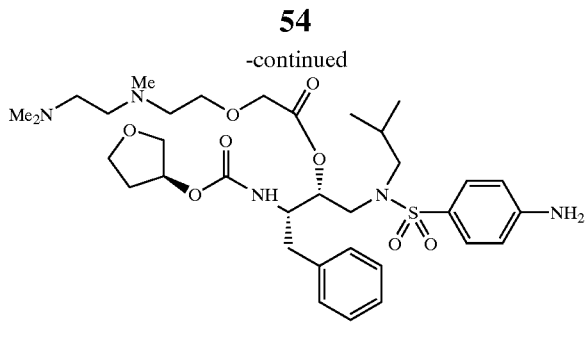

216

216 was obtained following the procedure of Example 12.

1H-NMR: 0.97 (6H,t), 1.95 (2H,m), 2.20 (1H,m), 2.9 (2H,m), 2.96 (6H,s), 3.00 (3H,s), 3.38 (1H,m), 3.42 (3H,m), 3.36 (1H,m), 3.6 (2H,m), 3.7 (6H,m), 3.98 (2H,m), 4.2 (2H,dd), 5.1 (1H,bs), 5.4 (1H,m), 6.8 (2H,d), 7.4 (5H, m), 7.6 (2H,d).

LC-MS: 1 peak, 692 (MH+).

EXAMPLE 19

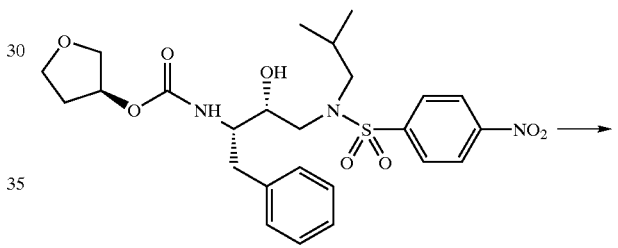

197

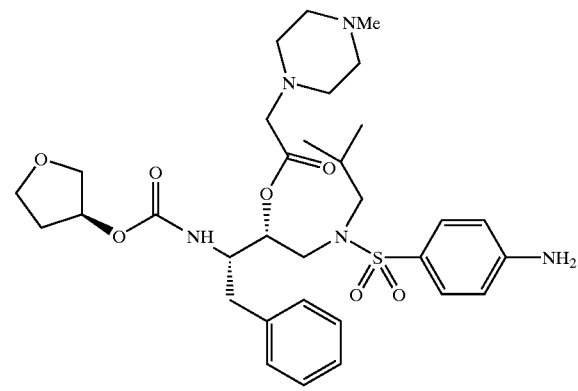

217

217 was obtained following the procedure of Example 12.

1H-NMR (CDCl3): 0.78 (6H,dd), 1.9 (2H,m), 2.1 (1H,m), 2.3 (3H,s), 2.9 (8H,m), 2.9 (2H,m), 3.15 (1H,m), 3.35 (1H,m), 3.5 (1H,m), 3.75 (4H,m), 4.06 (2H,s), 4.15 (2H,m), 4.9 (1H,dd), 5.05 (1H,bs), 5.2 (1H,bs), 6.63 (2H,d), 7.2 (5H,m), 7.55 (2H,d), 8.0 (2H,m).

ESMSP: 676 (MH+).

EXAMPLE 20

General Procedure for N-acylated Compounds

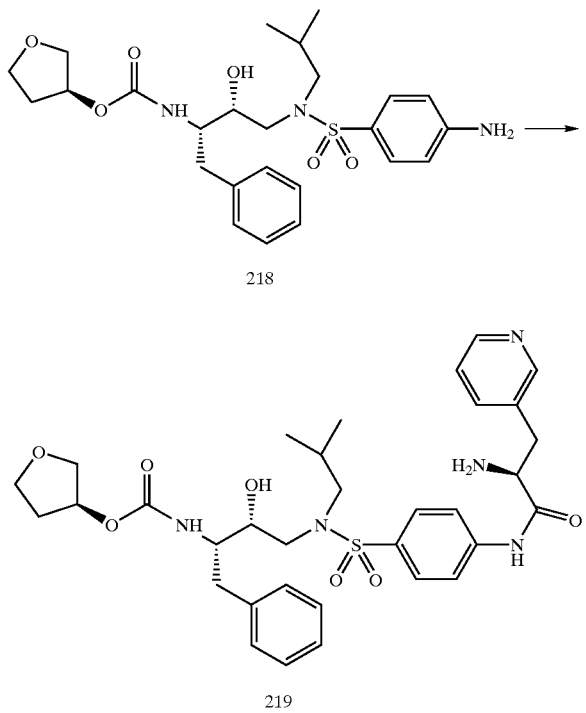

A mixture of 0.5 g (1 mmol) of (3S)-Tetrahydro-3-furyl-N-((1S,2R)-1-benzyl-2-hydroxy-3-(N-isobutyl-4-aminobenzenesulfonamido)propyl) carbamate, 0.4 g (1.5 mMol) of Boc-(S)-3-pyridyl alanine, 0.29 g (1.5 mMol) EDCI and 0.1 g 4-dimethylamino pyridine in 10 ml of N,N-dimethylformamide was stirred at 25° for 12 hours. The volatiles were removed in vacuo and the residue was partitioned between ethyl acetate and 1N hydrochloric acid. The organic layer was washed with 1N sodium hydroxide and brine, dried over magnesium sulfate and concentrated in vacuo. The residue was chromatographed on a 2 inch plug of silica gel (1:1 ethyl acetate:hexane) to give the desired N-acylated material. Deprotection by treatment with 50 ml of trifluoroacetic acid, followed by co-evaporation of residual acid with methanol gave the desired prodrug as a white foam (0.2 g, 26%).

H1-NMR (acetonitrile-D3): 0.95 (6H,dd), 2.0 (2H,m), 2.25 (1h,m), 2.8–3.1 (5H,m), 3.6–4.0 (7H,m), 4.25 (1H,m), 4.75 (1H,m), 5.18 (1H,m), 5.45 (1H,m), 7.0 (2H,d), 7.4 (5H,m), 7.75 (2H,d), 8.2 (1H,m), 8.8 (1H,d), 8.85 (1H,d), 9.15 (1H,s).

LC/MS: 1 peak, 654 (MH+).

EXAMPLE 21

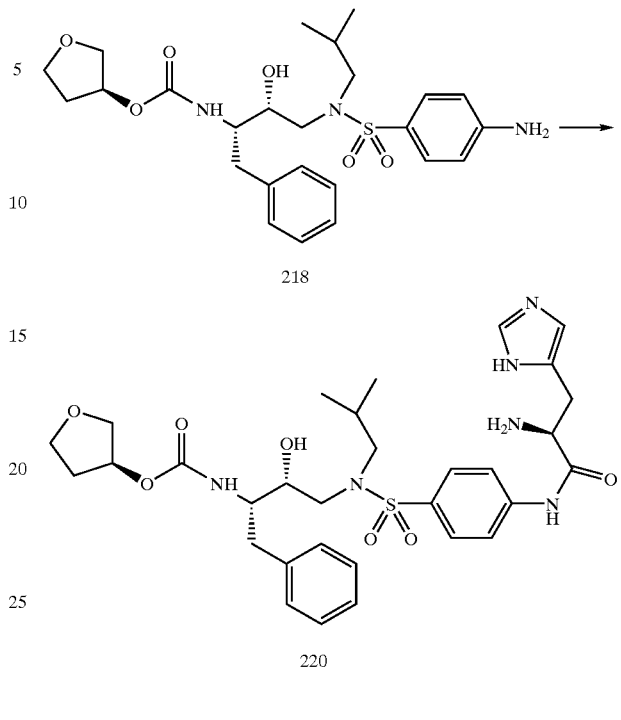

220 was obtained using the general procedure On Example 20.

1H-NTMR (acetone-d6/methanol-d4): 0.95 (6H,t), 2.0 (2H,m), 2.2 (1H,m), 2.90 (1H,dd), 2.95 (2H,d), 3.12 (1H, dd), 3.4 (2H,m), 6 (1H,d), 3.8 (5H,m), 4.4 (2H,bm), 6.82 (2H,d), 7.20 (1H,s), 7.4 (5H,m), 7.65 (2H,d), 8.0 (1H,s).

LC/MS: 1 peak, 643 (MH+).

EXAMPLE 22

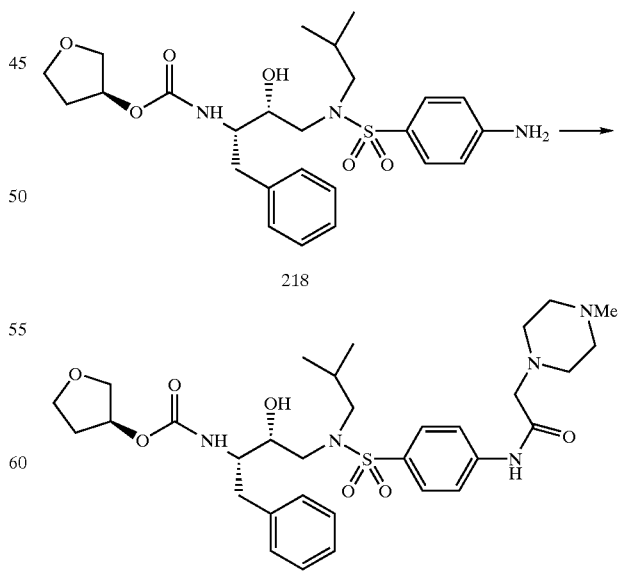

221 was obtained using the general procedure in Example 20.

1H-NMR (DMSO d-6): 0.76 (6H,t), 1.80 (2H,m), 2.10 (1H,m), 3.7 (4H,m), 3.75 (3H,s), 3.2 (5H,m), 3.58 (2H,s), 3.7 (4H,m), 4.97 (1H,bm), 5.18 (1H,bs), 6.7 (2H,d), 7.22 (5H,m), 7,45 (2H,d).

LC/MS: 1 peak, 646 (MH+).

EXAMPLE 23

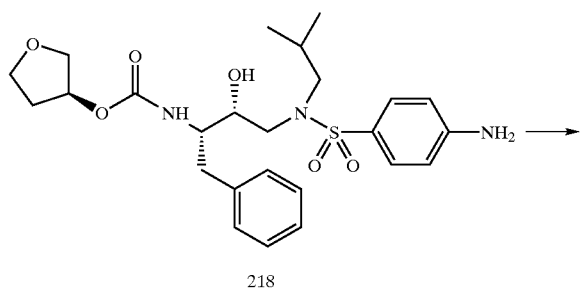

218

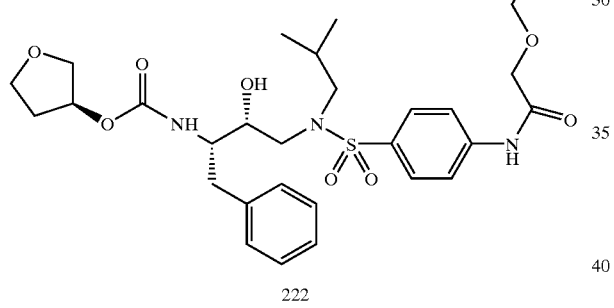

222

222 was obtained using the general procedure in Example 20.

1HNMR (acetonitrile d-3): 1.0 (6H,t), 2.0 (2H,m), 2.2 (1H,m), 3.00 (6H,s), 3.02 (3H,s), 3.1 (4H,m), 3.5 (3H,m), 3.8 (8H,m), 4.4 (2H,s), 5.15 (1H,bs), 7.4 (5H,m), 7.97 (2H,d), 8.04 (2H,d).

LC/MS: 1 peak, 692 (MH+).

EXAMPLE 24

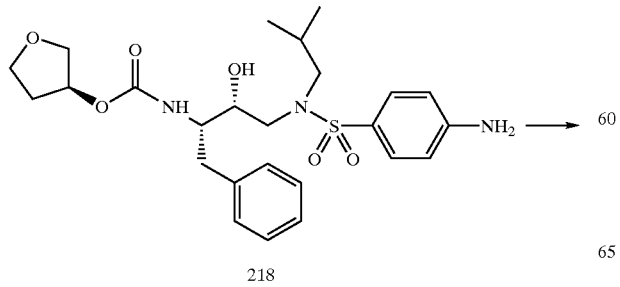

218

-continued

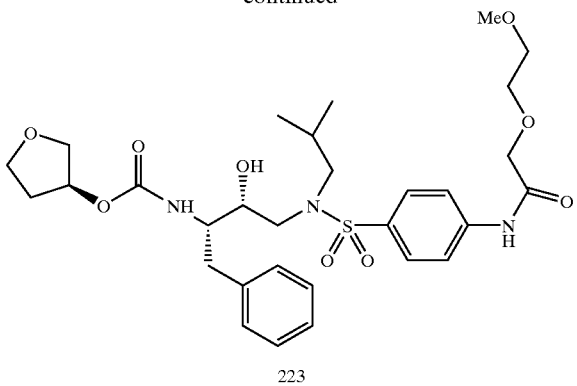

223

223 was obtained using the general procedure in Example 20.

t HPLC=9.22 min (D); ES+ 622 (M+1).

1H NMR d6-DMSO: 0.76 (6H,dd), 1.0–1.8 (15H,m), 2.03 (1H,m), 2.58 (2H,m), 2.79 (2H,m), 3.11 (1H,m), 3.28 (3H,s), 3.3–3.5 (12H,m), 3.94 (1H,m), 4.08 (1H,m), 4.94 (1H,m), 5.14 (1H,m), 6.61 (2H,d), 7.22 (5H,m), 7.40 (3H,m).

13C (DMSO) 169.7, 165.9, 152.9, 138.4, 129.2, 129.1, 128.1, 126.2, 123.1, 112.8, 74.4, 74.1, 72.5, 71.2, 69.8, 66.1, 58.1, 57.1, 52.9, 47.5, 33.4, 33.2, 26.3, 24.5, 18.9, 18.8.

EXAMPLE 25

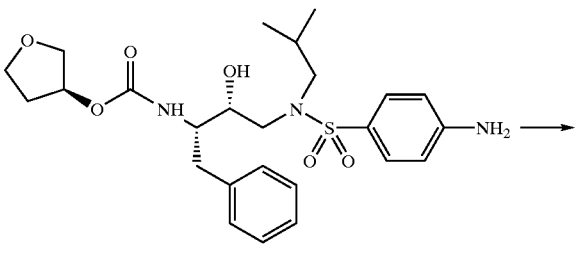

218

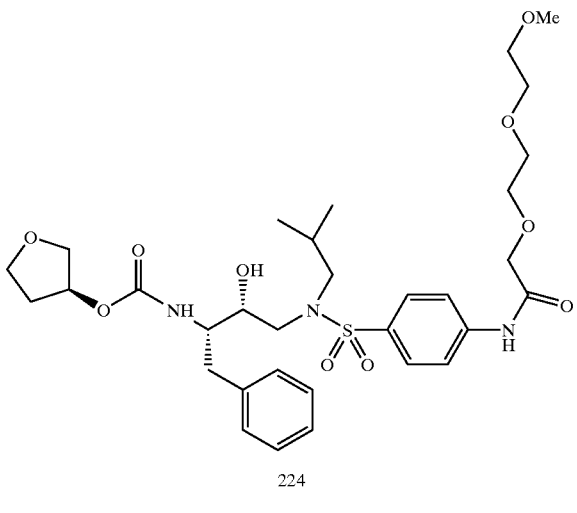

224

224 was obtained using the general procedure in Example 20.

EXAMPLE 26

O,N-diacylated Prodrugs

The general procedure for N,O-diacylated compounds followed the protocol outlined in Example 20, above, except that a five fold excess of reagents was used relative to the starting material.

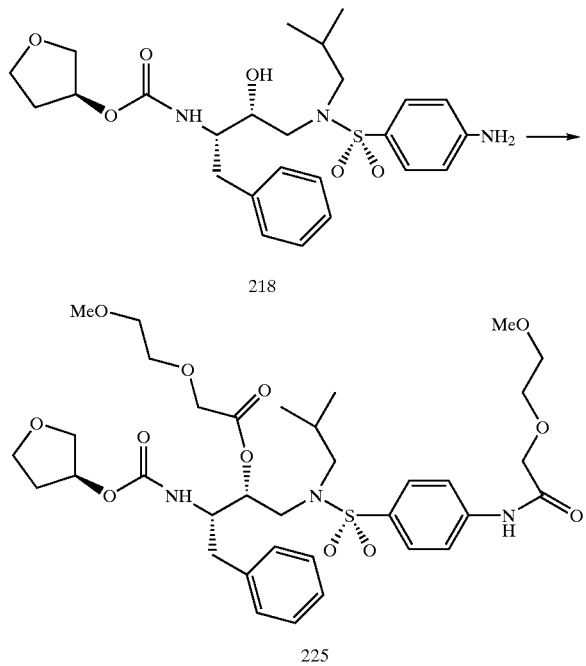

t HPLC 9.26 min (D); ES+ 738 (M+1) 760 (M+Na).

13C (DMSO): 170.2, 169.8, 156.4, 143.4, 138.8, 129.5, 128.8, 128.5, 126.8, 119.7, 74.9, 74.2, 73.7, 71.6, 70.7, 70.3, 68.0, 67.2, 59.3, 57.6, 53.8, 49.6, 35.7, 33.8, 27.1, 20.4.

1H (DMSO): 10.1 (1H, s), 7.84 (d, 2H, J=8.5), 7.76 (d, J=8.7, 2H), 7.40 (1H, d, J=9.2), 7.22 (m, 5H), 5.14 (1H, m), 4.95 (1H, m), 4.1 (m, 8H), 3.7–3.3 (m, 13H), 3.28 (s, 3H), 3.26 (s, 3H), 2.86 (m, 2H), 2.73 (m, 1H), 2.59 (m, 1H), 2.04 (m, 1H), 1.83 (m, 2H), 0.78 (m, 6H).

EXAMPLE 27

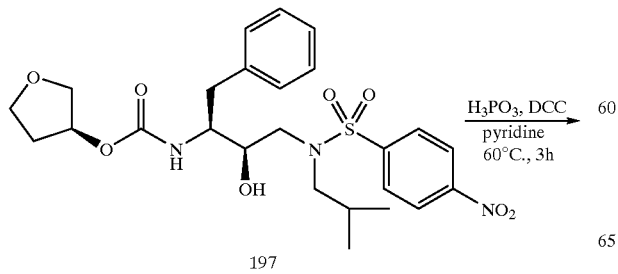

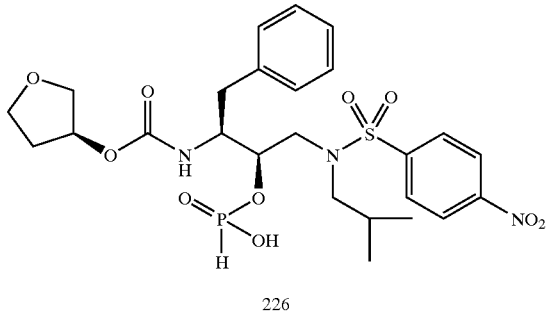

To a mixture of 197 (2.93 g, 5.47 mmol) and phosphorous acid (Aldrich, 2.2 equiv., 12.03 mmol, 987 mg) in 20 ml pyridine was added 1,3-dicyclohexylcarbodiimide (Aldrich, 2.1 equiv., 11.49 mmol, 2.37 g) and the reaction heated to 60° C. under nitrogen for 3 h. Solvent was removed in vacuo, the residue treated with 200 ml 0.1N aqueous sodium bicarbonate and stirred 1h at ambient temperature. The mixture was filtered, the filtrate acidified to pH 1.5 by addition of conc. HCl and extracted with ethyl acetate (3×100 ml). The combined orgnic layers were dried over magnesium sulfate, filtered and concentrated in vacuo to give 3.15 g (969%) of desired product 226 which was used directly in the next reaction. HPLC: Rt=8.91 min (96%), MS (AP+) 600.5 (M+1).

EXAMPLE 28

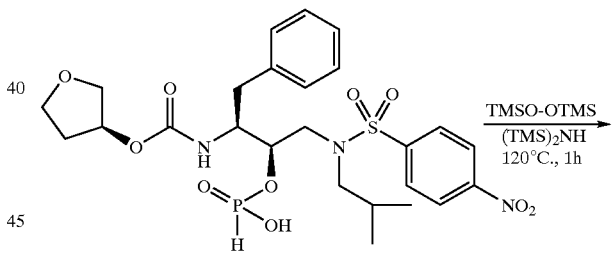

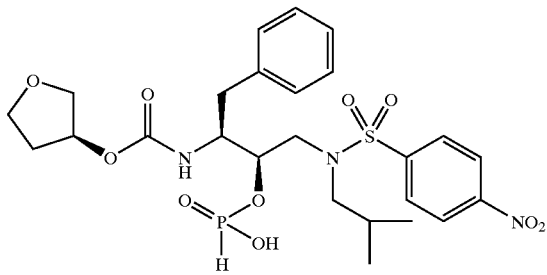

A suspension of 226 (~5.47 mmol) in 18 ml hexamethyldisilazane was stirred at 120° C. until homogeneous followed by addition of bis(trimethylsilyl) peroxide (Gelest, Inc., 2.3 equiv., 12.58 mmol, 2.24 g, 2.71 ml). After 1h the mixture was cooled to ambient temperature, solvent removed in vacuo, the residue stirred with 100 ml methanol, solvent removed in vacuo, the residue stirred with 100 ml 0.1N aqueous sodium bicarbonate, acidified to pH 1.5 by addition of conc. HCl, saturated with brine and extracted with ethyl acetate (3×100 ml). The combined organic layers were dried over magnesium sulfate, filtered and concentrated in vacuo to give 2.98 g (88%) of desired product 227, which was used directly in the next reaction. HPLC: Rt=9.28 min (90%), MS (AP+) 616.5 (M+1).

Alternatively, 227 can be synthesized directly from 197. In this method, 197 was dissolved in pyridine (300 mL). The resulting solution was concentrated in vacuo to about 150 ml at 50–55° C. The solution was then cooled under $N_2$ to 5° C., and treated with $POCl_3$ (6.5 ml, 1.24 equiv.) over 2 minutes. The cooling bath was removed and the reaction stirred at ambient temperature for 2.5 hrs. The solution was then cooled to 5° C. and water (300 ml) was added over 30 minutes.

The resulting mixture was extracted with 4-methylpentan-2-one (MIBK, 2×150 ml). The combined extracts were washed with 2N HCl (2×250 ml). The acid washes were back extracted with MIBK (60 ml), then the combined MIBK solutions were treated with 2N HCl (150 ml). The two phase mixture was stirred rapidly and heated to 50° C. for 2 hours. The reaction mixture was cooled to 20° C., the phases were separated and the MIBK solution was washed with brine (150 ml). The product, 227, was isolated by drying the solution with magnesium sulfate, filtering of the drying agent and concentrating in vacuo at 40° C. to give the product as a pale yellow foam (31 g, 90%) yield)

EXAMPLE 29

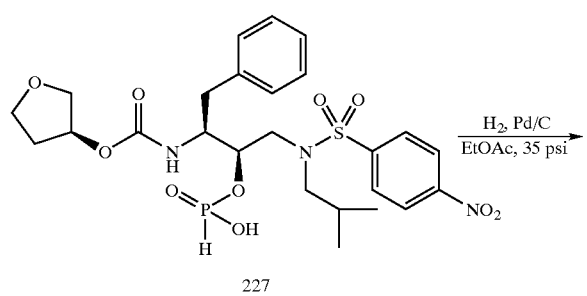

227

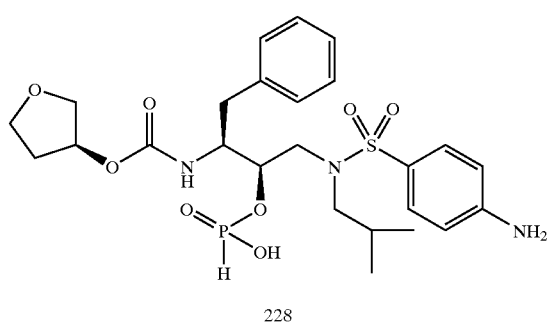

228

A solution of 227 (2.98 g, 4.84 mmol) in 50 ml ethyl acetate was treated with 10% palladium on carbon (Aldrich, 300 mg) and put under 35 psi of hydrogen on a Parr shaker for 15 h. Catalyst was removed by filtration and solvent removed in vacuo to give 2.66 g (94%) of desired product 228. HPLC: Rt=7.23 min (92%), MS (ES+) 586.3 (M+1).

EXAMPLE 30

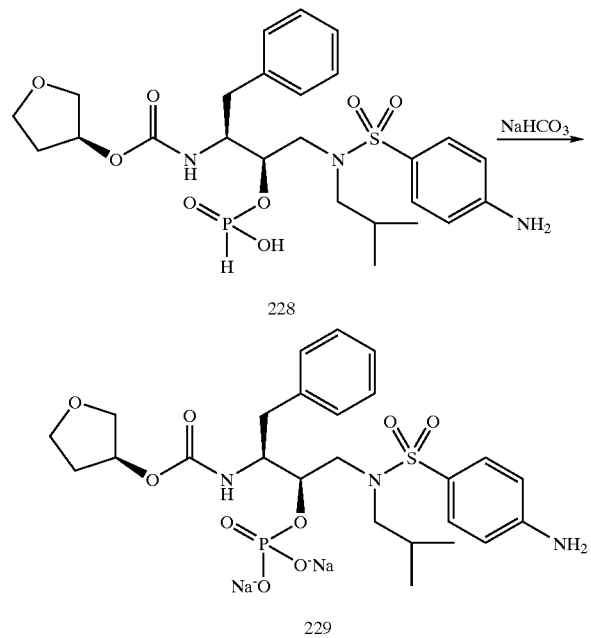

228

229

Solid 228 (2.66 g, 4.54 mmol) was treated with 10 ml aqueous sodium bicarbonate (Baker, 3.0 equiv., 13.63 mmol, 1.14 g) and loaded onto a resin column (Mitsubishi Kasei Corp., MCI-gel, CHP-20). Distilled water was run through until the eluent was neutral followed by product elution with 1% acetonitrile in water. Pure fractions were pooled and lyophilized to give 918 mg of pure bis-sodium salt 229.

Alternatively, 7 g of 228 was dissolved in 100 ml of EtOAc with warming and the solution was extracted with 100 ml of aqueous 250 mM triethylammonium bicarbonate (TEABC) (2×). The aqueous extracts were combined and diluted to 1500 ml with water. This solution was applied to a 300 ml DEAE-52 column (Whatman) which was equilibrated with 50 mM TEABC. The column was washed with 8 L of 50 mM TEABC and the TEA salt was eluted with 2 L of 250 mM TEABC. The solution was evaporated en vacuo to 100 ml then lyophilized to yield the TEA salt (1.5 TEA equivalents). The TEA salt was (5.8 g) was dissolved in 200 ml water, 300 ml of 1 N HCl was added and the mixture was extracted with EtOAc (3×200 ml). The ethyl acetate solution was dried with MgSO4 then evaporated en vacuo to yield 4 g of the free acid. Two rams of the free acid was dissolved in 50 ml of acetonitrile and a solution of 573 mg $NaHCO_3$ in 200 ml water was added. The mixture was lyophilized yielding 2.1 g of the bis sodium salt (compound 229).

EXAMPLE 31

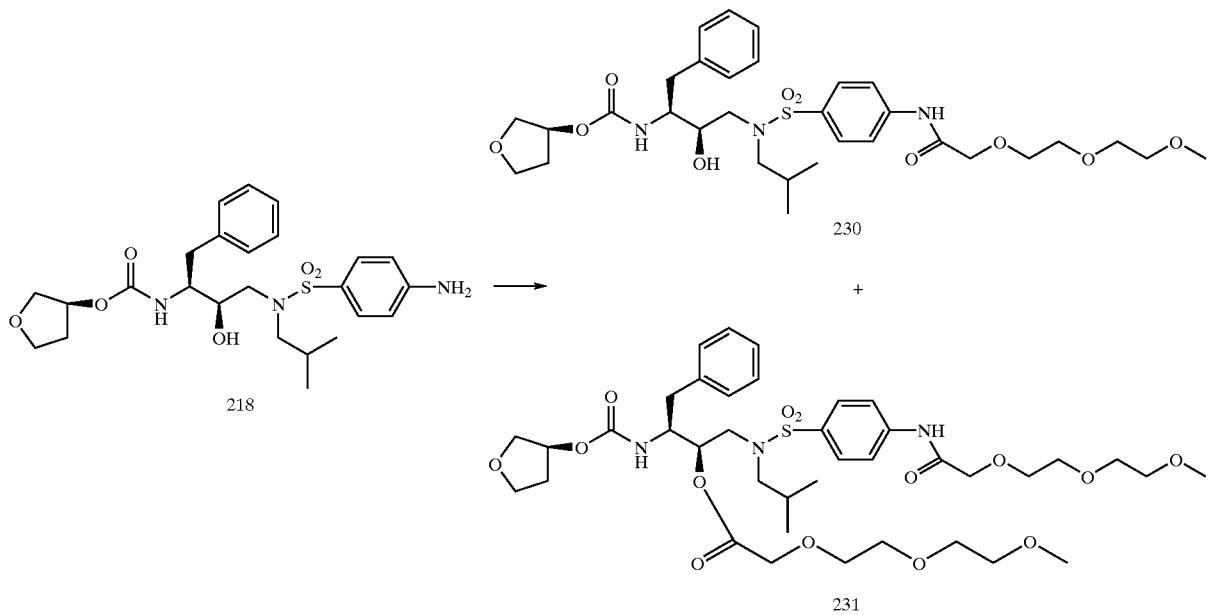

0.53 g (3.0 mmol) 2-[2-(2-Methoxyethoxy)ethoxy] acetic acid was added to a stirred solution of 1.2 g (3.15 mmol) HATU 0.2 g (1.47 mmol) HOAt 0.4 g (4.0 mmol) NMM in 10 ml anhydrous N,N-dimethylformamide. The mixture was stirred at room temperature for 30 minutes, then 0.5 g (1 mmol) of (3S)-Tetrahydro-3-furfuryl-N-((1S,2R)-1-benzyl-2hydroxy-3-(N-isobutyl-4-aminobenzenesulfonamido)-propyl) carbamate was added to the solution in one portion. The mixture was stirred at 20° C. for an hour then at 50° C. for an additional 12 hours. It was then cooled to 20° C., 50 ml of ether was added, and the solution was washed with water three times. The aqueous phase was washed with ether, and then the combined organic phases were dried with anhydrous magnesium sulfate and filtered. The filtrate was concentrated under reduced pressure and the residue was purified by silica gel chromatography to obtain the desired Mono-(N)acylated (102 mg, 15%) and Bis-(O,N) acylated (262 mg, 32%) compounds.

Mono-(N)-acylated: 1H-NMR(CDCl3): 0.85 (dd, 6H), 1.85 (m, 2H), 2.08 (m,1H), 2.8–3.1 (m, 7H), 3.33 (s, 3H), 3.55 (m, 3H), 3.70–3.90 (m, 8H), 4.1 (s, 2H), 5.0 (d, 1H), 5.08 (s(br), 1H), 7.2 (m, 5H), 7.70 (d, 2H), 7.80 (d, 2H), 9.09 (s, 1H).

MS(FAB+): 666 (M+1).

Bis-(O,N)-acylated: 1H-NMR(CDCl3): 0.77 (m, 6H), 1.81 (m, 1H), 1.95 (m, 1H), 2.05 (m, 1H), 2.6–3.0 (m, 6H), 3.2 (m,1H), 3.332 (s, 3H), 3.338 (s, 3H), 3.5–3.8 (m, 18H), 4.1 (s, 2H), 4.14 (s, 2H), 4.17 (m, 1H), 5.05 (m, 2H), 5.25 (s(br), 1H), 7.2 (m,5H), 7.69 (d, 2H), 7.78 (d 2H), 9.06 (s, 1H).

MS (FAB+): 826(M+1), 848(M+Na).

EXAMPLE 32

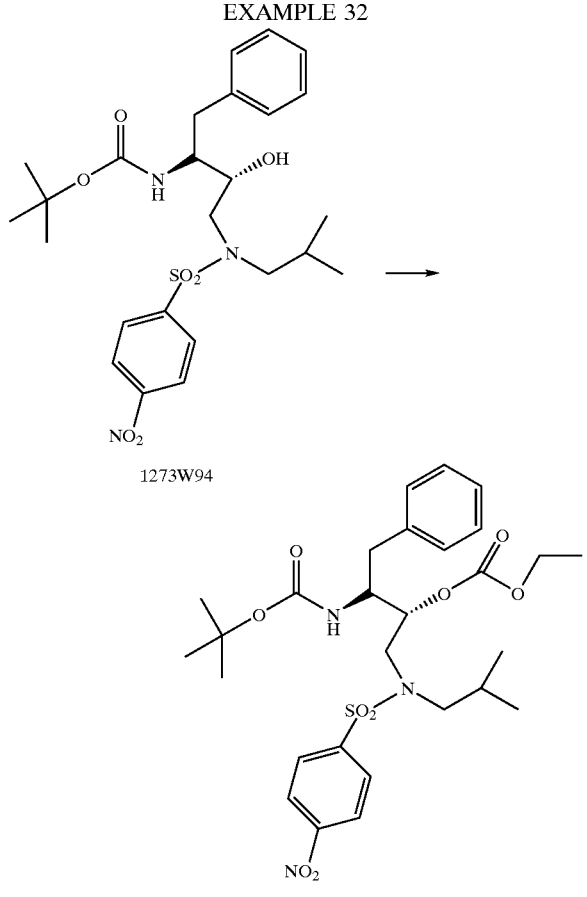

We dissolved 0.521 g (1 mM) of 1273W94 in 5 ml THF, then cooled to −78° C. under nitrogen, and added 1.56 ml (2.5 mM) of a 1.6 M solution of nBuLi in hexane. After 20 min at −78° C., we added 105 μL (1.1 mM) of ethyl chlorocarbamate and warmed up the reaction to room temperature, followed by addition of another 105 μL of ethyl chlorocarbamate.

After stirring for additional 4 hrs, the reaction was quenched with water and the organic solvent evaporated. Part of the crude product was purified on a silica gel (Rf=0.69 (1:2 ethyl acetate:hexane)), yielding 0.131 g of the product.

C,H,N: calc: 46.06, 4.97, 5.88, found 45.90, 4.97, 5.88 $C_{23}H_{33}N_5O_5S_1$. 2.2 TFA LC/MS (ES+) 594 (M+1) 1 peak at 6.96 min.

Analytical HPLC(A) t=24.57 min.

13C (CDCl3): 155.8, 154.4, 149.9, 145.7, 136.8, +129.2, +128.7, +126.8, +124.2, 80.1, +76.9, −64.3, −56.2, −52.5, −48.7, −36.2, +28.1, +26.4, +20.0, +19.8, +14.3.

EXAMPLE 33

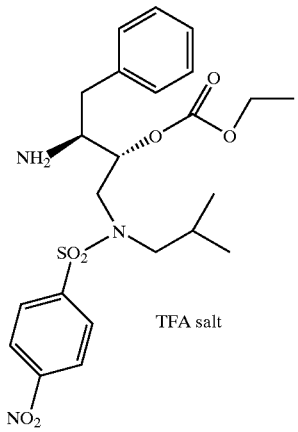

TFA salt

233

We dissolved 0.131 g of the above ethyl carbonate in 4 ml DCM, followed by 4 ml of TFA. Solvents were then removed after 45 min at room temperature, resulting in the title compound.

1H (DMSO): 8.37 (2H, d, J=7.2), 8.15 (2H, m), 8.00 (2H, d, J=7.0), 7.37 (5H, m), 5.04 (1H, d, J=6.9), 4.06 (2H, q, J=7.0), 3.82 ((1H, m), 3.35 (2H, m), 2.95 (4H, m), 1.82 (1H, m), 1.20 (3H, t, J=7.0), 0.72 (overlapping doublets, 6H, J=6.2).

LC/MS 1 peak at 4.76 min.

ES+ 497.3 (M+1).

EXAMPLE 34

O, N-Acyloxy Rearrangement

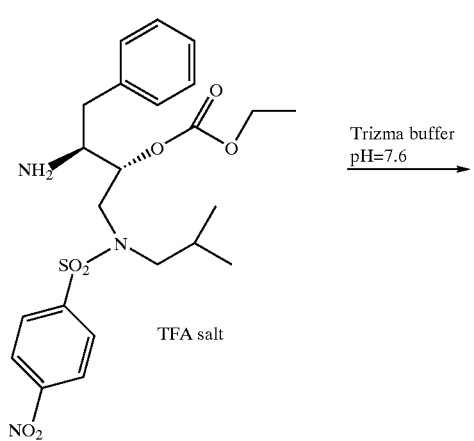

TFA salt

233

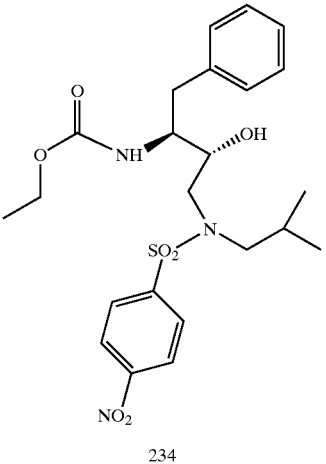

234

C,H,N: calc:53.26, 6.14, 7.57, found 53.22, 6.14, 7.57 $C_{23}H_{33}N_5O_5S_1 \times 0.8$ TFA LC/MS (ES+) 594 (M+1) 1 peak at 6.96 min.

Analytical HPLC(A) t=24.57 min.

1H (DMSO): 8.34 (2H, d, J=8.7), 8.02 (2H, d, J=8.0), 7.19 (5H, m), 6.98 (1H, d, J=7.2), 5.00 (1H, m), 3.83 (2H, q), 3.50 (2H, m), 3.06 (m, 2H), 2.96 (2H, m), 2.43 (1H, m), 1.97 (1H, m), 1.02 (3H, t), 0.84 (3H, d), 0.82 (3H, d).

13C (DMSO): 156.2, 150.1, 145.7, 140.0, +129.7, +129.2, +128.5, +126.3, +125.0, +71.8, −60.0, +56.2, −56.0, −51.8, −36.0, +26.3, +20.3, +20.1, +14.6.

EXAMPLE 35

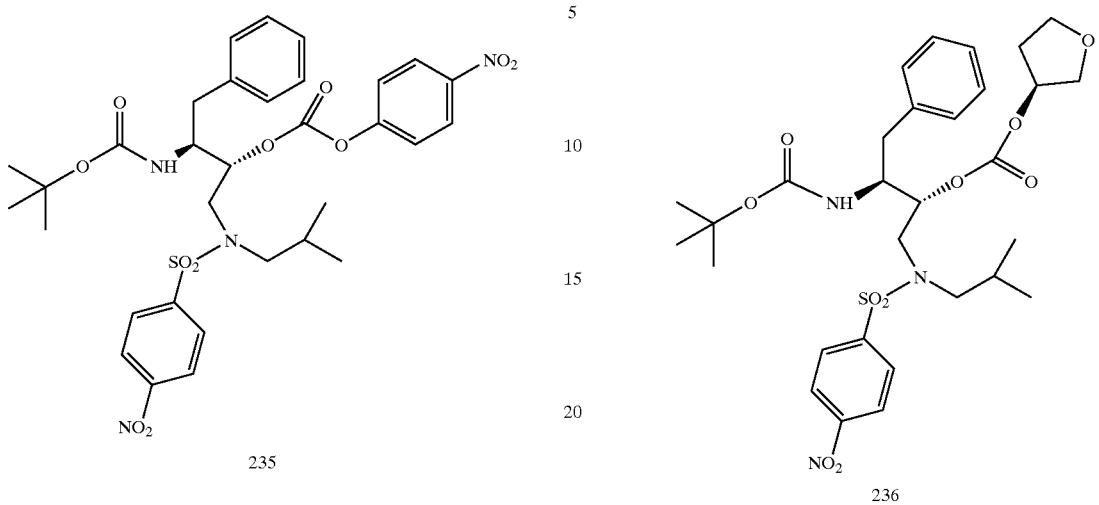

235

Synthesis of 235 was accomplished analogous to that set forth in Example 1.

Yield 15.2%; tHPLC=25.2 min (A).

Rf=0.54 (B); ES+ 687.3 (M+1).

1H (CDCl3): 8.34 (overlapping d+d, 4H), 7.97 (d, 2H, J=8.9), 7.35 (7H, m), 5.09 (1H, m), 4.56 (1H, d, J=8.4), 4.20 (1H, m), 3.54 (1H, m), 3.00 (3H, m), 2.82 (1H, m), 1,84 (1H, m), 1.37 (9H, s), 0.84 (3H, d), 0.82 (3H, d).

EXAMPLE 36

236

We dissolved 150 mg of 235 in 3 ml of anhydrous dioxane, added 0.35 ml of S(+)-3-OH-THF and 0.14 ml triethyl amine. The mixture was refluxed gently under nitrogen for 2 days. Conversion to 236 was quantitative. Solvents were removed and the compound purified on silica (B).

tHPLC=22.98 min (A); ES+ 636.2 (M+1).

1H NMR (CDCl3): 8.29 (2H, d), 7.91 (2H, d), 7.22 (5H, m), 5.13 (1H, m), 4.96 (1H, m), 4.52 (1H, d), 4.02 (1H, m), 3.84 (2H, m), 3.44 (1H, m), 3.36 (1H, m), 3.10 (3H, m, overlap), 2.88 (2H, m), 2.64 (1H, m), 2.14 (1H, m), 2.05 (1H, m), 1.84 (1H, m), 1.27 (9H, s), 0.78 (6H, two overl. d).

EXAMPLE 37

Cabonhydrate-Based Prodrugs

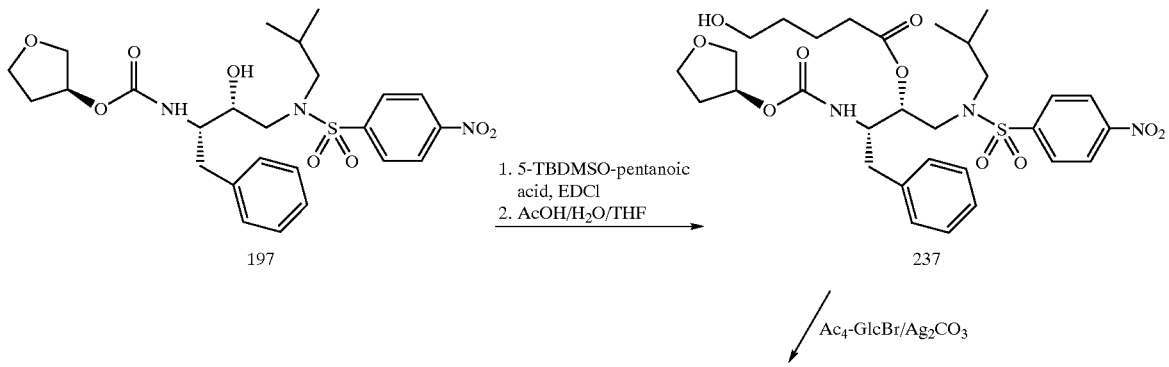

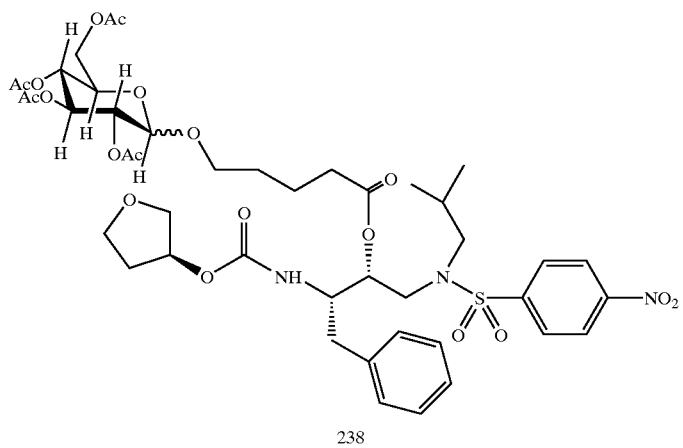

238

A mixture of 0.54 g (1 mMol) of (3S)-Tetrahydro-3-furfuryl-N-((1S,2R)-1-benzyl-2-hydroxy-3-(N-isobutyl-4-aminobenzenesulfonamido)propyl)carbamate, 0.46 g (2 mMol) of 5-dimethyl-tert-butyosilyloxypentanoic acid, 0.346 g (1.8 mMol) of EDCI and 0.556 mL (4 mMol) of triethylamine in 10 ml of dimethyl formamide was stirred at rt for 24 h. Another 3 mMol each of acid, EDCI and triethylamine were added and stirring was continued for an additional 96 h. A third batch of acid and EDCI was added (3 mMol each) and the mixture was stirred 72 h to complete the reaction.

The reaction mixture was then diluted with ethyl acetate and extracted with 1N hydrochloric acid, saturated sodium bicarbonate and water. Evaporation of the solvent and purification on silica gel (30% ethyl acetate-hexane) gave the desired product (500 mg) as a waxy solid.

LCMS: 1 peak, 772.5 (M+Na)

1H NMR (CDCL3): 0.01 (6H,s), 0.78 (6H,dd), 0.95 (9H,s), 1.4–1.8 (6H,m), 1.9 (2H,m), 2.05 (1H,m), 2.3 (2H,m), 2.65 (1H,m), 2.95 (2H,m), 3.22 (1H,m), 3.4 (1H,m), 3.6 (2H,m), 3.75 (3H,m), 4.8 (1H,d), 5.1 (1H,bs), 5.2 (1H,bs), 7.2 (5H,m), 7.95 (2H,d), 8.36 (2H,d).

450 mg of the 238 was dissolved in 30 ml of tetrahydrofuran and treated with 20 ml of water and 50 ml of acetic acid. The mixture was stirred at rt for 2 h and evaporated. Titration with hexane gave the desired alcohol (290 mg) as a white solid.

A mixture of 0.15 g (0.24 mMol) of the alcohol produced above from the previous reaction, 0.205 g (0.5 mMol) of tetraacetylglucosylbromide and 0.191 g (0.7 mMol) of silver carbonate in 3 ml of dichloromethane was stirred at rt for 6 h. 150 mg of additional glucosyl bromide and 150 mg of silver carbonate were added and the mixture was stirred at rt overnight. The mixture was loaded onto a pad of silica gel and eluted with 30% ethylacetate-hexane to afford the desired protected carbohydrate pro-drug as a white foam (200 mg).

LCMS: 1 peak, 966 (M+H).

1H-NMR (CDCl3): 0.78 (6H,dd), 1.9 (2H,m), 2.00 (3H, s), 2.02 (3H,s), 2.05 (3H,s), 2.06 (3H,s), 2.1 (2H,m), 2.3 (2H,m), 2.7 (1H,m), 2.94 (3H,bd), 3.35 (2H,m), 3.45 (2H.m), 3.8 (5H,m), 4.1 (3H,m), 4.5 (1H,d), 4.9 (1H,bs), 4.95 (1H,t,), 5.08 (4H,m), 2H,d), 8.35 (2H,d).

EXAMPLE 38

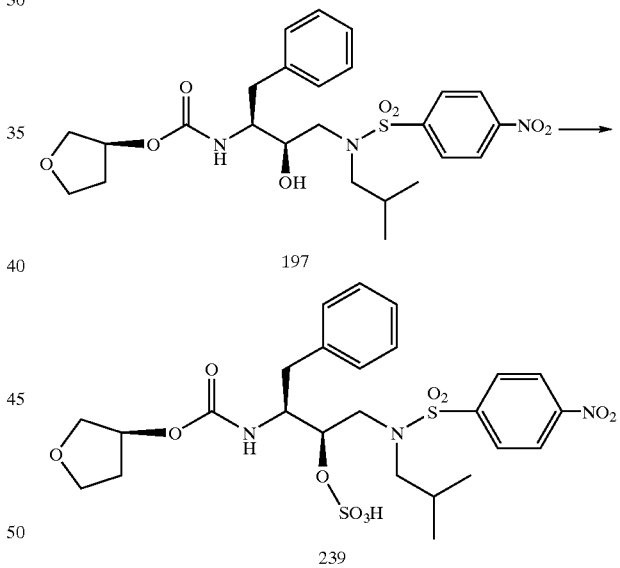

1.5 g (9.4 mmol) SO3.py complex was added to a stirred solution of 1 g (1.87 mmol) of 197 in 25 mL anhydrous tetrahydrofurane. The mixture was stirred at 20° C. for 12 hours, then filtered. The filtrate was concentrated at reduced pressure, and the residue was transferred to a silica gel column and eluted with EtOAc (neat), followed by EtOAc-:EtOH (4:1) to obtain 471 mg (47%) 239 as a colorless foam.

1H-NMR(CDCl3): 0.80 (m, 6H), 1.8–2.1 (m, 3H), 4.15 (s(br), 1H), 4.8 (t, 1H), 5.04 (s (br), 1H)

MS(ES-): 614 (M-1).

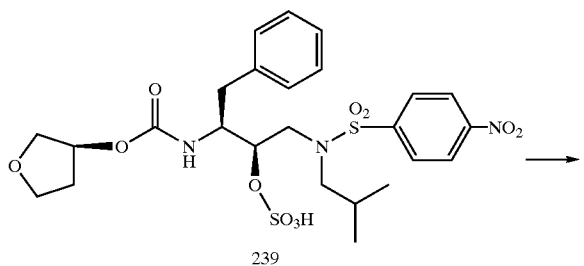

239

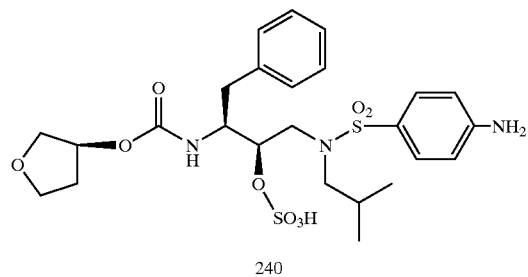

240

100 mg (0.162 mmol) 239 dissolved in 15 ml anhydrous tetrahydrofuran and 200 mg Pd/BaSO4 (5%) was added to the solution. The mixture was stirred under atmospheric pressure of hydrogen for 8 hours, and then the catalyst was filtered. The filtrate was concentrated under reduced pressure then dried under vacuum (~1 Hg mm, 48 hrs.) to produce 80 mg (81%) 240 as a colorless foam.

1H-NMR(DMSO-d6): 0.85 (dd, 6H), 0.90 (m, 1H), 2.05 (m, 2H), 2.58 (m, 3H), 2.84 (dd, 1H), 3.05 (m, 2H), 3.55–3.80 (m, 6H), 4.20 (t, 1H), 4.42 (m, 1H), 4.93 (s(br), 1H), 6.09 (s, 2H), 6.70 (d, 2H), 6.80 (d, 1H), 7.15–7.40 (m, 4H), 7.51 (d, 2H).

MS(ES−) : 584 (M−1).

EXAMPLE 39

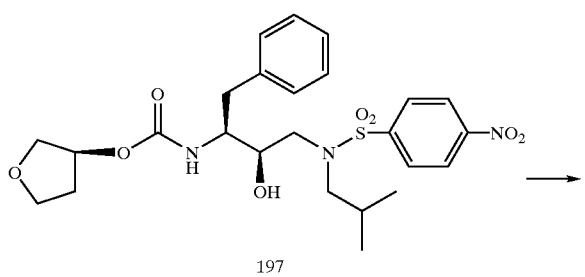

197

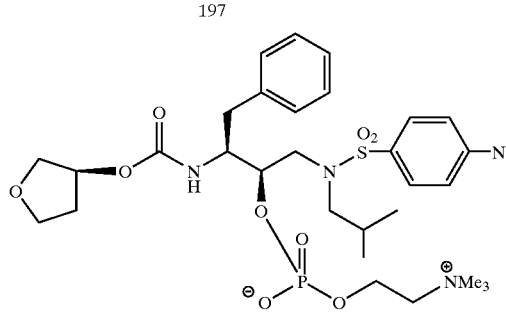

241

780 mg (3 mmol) 2-Chloro-1,3,2-dioxaphospholane was added to a stirred solution of 1.07 g (2 mmol) 197 and 0.7 ml (4 mmol) N,N-Diisopropylethylamine in 25 ml dichloromethane at 0° C. The mixture was allowed to warm up to room temperature and it was stirred for 2 hours. The mixture was then cooled to 0° C. and 1.5 g (9.3 mmol) bromine was added in 5 ml dichloromethane. The mixture was stirred for 1 hour at 20° C., followed by evaporation under reduced pressure. An aqueous solution (50%) of 15 ml trimethylamine was added to the residue, and the mixture was stirred at 20° C. for 12 hours.

Solvents were removed under reduced pressure and 50 ml EtOAc:EtOH (9:1) was added to the residue. The solid was filtered, washed with EtOAc:EtOH (9:1) then the filtrate was concentrated under reduced pressure. The residue was chromatographed on a 3 inch plug of silica gel using ethyl acetate (neat), then methanol (neat), as eluents to obtain 1.15 g (82%) 241 as an off-white solid.

1H-NMR(CDCl3): 0.60 (dd, 6H), 1.70 (m, 1H), 1.95 (m, 1H), 2.10 (m, 1H), 2.8–3.2 (m, 6H), 3.4 (s (br), 9H), 5.09 (s(br), 1H), 7.25 (m, 5H), 7.83 (d, 2H), 8.28 (d, 2H).

MS(ES+): 701 (M+1), 184 (phosphatidyl choline+).

EXAMPLE 40

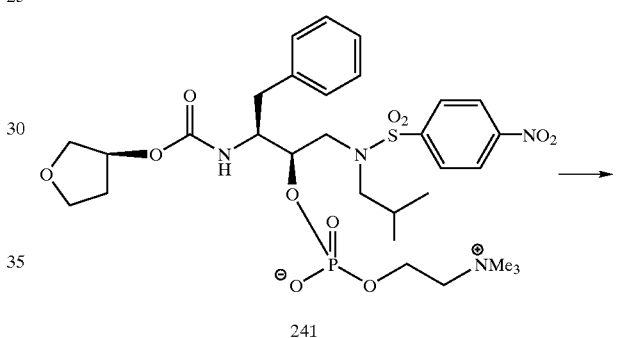

241

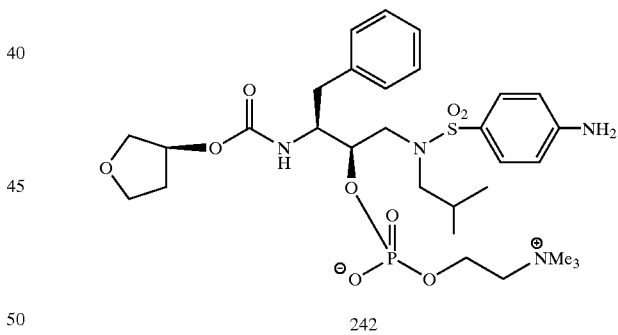

242

250 mg Pd/C (10%) was added to a solution of 250 mg (0.35 mmol) 241 in 10 ml methanol, and the mixture was stirred under atmospheric pressure of hydrogen for 4 hours at 20° C. The mixture was filtered, and the filtrate was concentrated under reduced pressure. The residue was then dissolved in 10 ml water and lyophilized to obtain 174 mg (74%) 242 as white solid.

1H-NMR(DMSO-d6): 0.82 (dd, 6H), 1.80–2.00 (m, 2H), 2.10 (m, 1H), 2.80 (m, 3H), 3.00 (m, 2H), 3.2 (s (br), 9H), 4.0–4.3 (m, 4H), 4.91 (s(br), 1H), 6.08 (s(br), 2H), 6.67(d, 2H), 7.30 (m, 5H), 7.48 (d, 2H), 8.12 (d, 1H).

MS(ES+): 671 (M+1), 184 (phosphatidyl choline+).

EXAMPLE 41

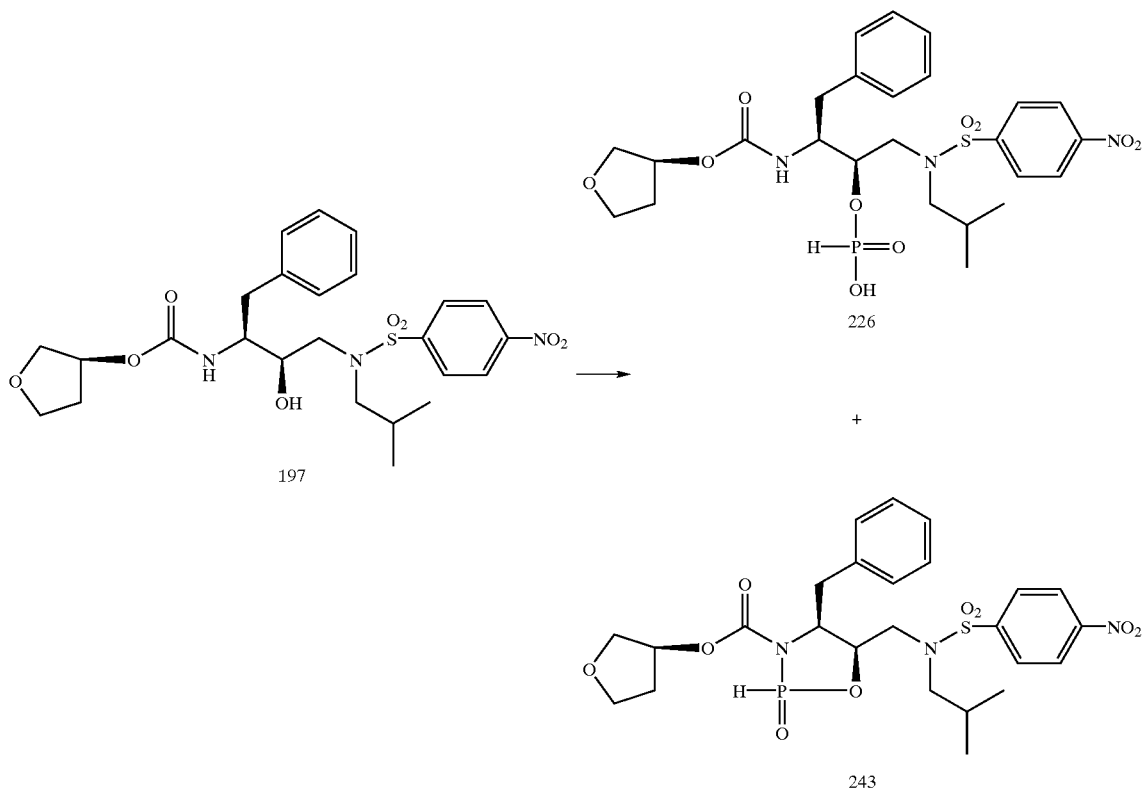

0.175 ml (2 mmol) phosphorus trichloride was added to a stirred solution of 1.07 g (2 mmol) 197 and 0.35 ml (2 mmol) N,N-Diisopropylethylamine in 25 ml dichloromethane at 20° C. The mixture was stirred for 4 hours at 20° C., then 1 ml water was added and stirred for an additional 12 hours at 20° C. 3 g anhydrous magnesium sulfate was added to the mixture and it was stirred for 30 minutes, then filtered. The filtrate was concentrated under reduced pressure and purified by silica gel chromatography using EtOAc:Hexane (4:1), then EtOAc:EtOH (1:1), to obtain 402 mg (48%) 226 and 427 mg (36%) 243.

226:

1H-NMR(DMSO-d6): 0.82 (dd, 6H), 1.84 (m, 1H), 1.98 (m, 1H), 2.10 (m, 1H), 2.68 (dd, 1H), 2.9–3.2 (m, 4H), 3.6–3.8 (m, 3H), 3.94 (t, 1H), 4.30, (s(br), 1H), 4.97 (s(br), 1H), 7.30 (m, 5H), 8.14 (d, 2H), 8.43 (d, 2H).

MS (ES−): 598 (M−1).

243: (1:1 mix of diastereomers):

1H-NMR(CDCl3): 0.80 (m, 6H), 1.8–2.1 (m, 4H), 2.8–3.2 (m, 6H), 3.7–3.9 (m, 4H), 4.15 (m, 1H), 4.8–5.15 (m, 2H), 5.57, 5.72 ((d,d), 1H), 7.25 (m, 5H), 7.95 (dd, 2H), 8.35 (m, 2H).

MS (ES−): 580 (M−1), 598 ( (M+H2O)−1).

EXAMPLE 42

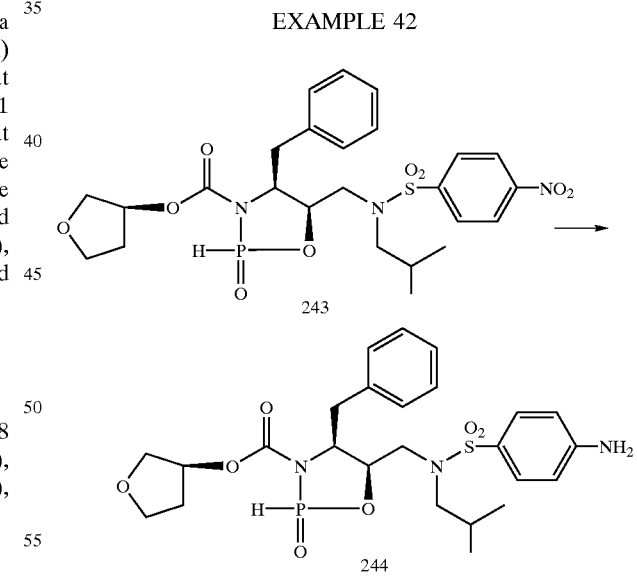

The reduction was carried out as described in Example 40; (Yield: 79%).

1H-NMR(DMSO-d6): 0.81 (dd, 6H), 1.82 (m, 1H), 1.95 (m, 1H), 2.08 (m, 1H), 2.6–3.15 (m, 6H), 3.6–3.75 (m, 3H), 4.03 (t, 1H), 4.28, (m, 1H), 4.96 (s(br), 1H), 6.07 (s, 2H), 6.65 (d, 2H), 7.25 (m, 5H), 7.42 (d, 2H).

MS (ES−): 568 (M−1).

EXAMPLE 43

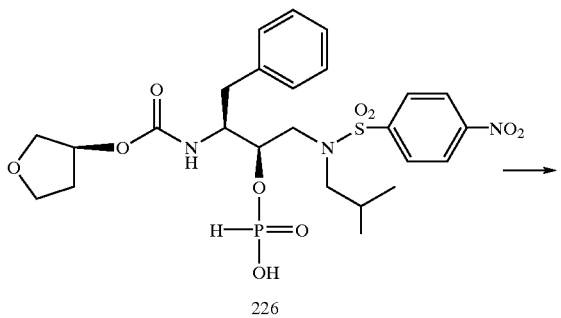

226

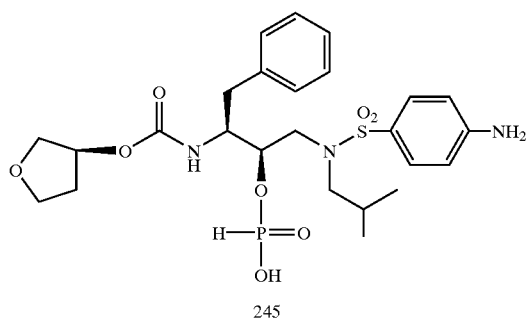

245

The reduction was carried out as described in Example 40; (Yield: 98%).

(1:1 mix of diastereomers):

1H-NMR(DMSO-d6): 0.82 (m, 6H), 1.75–2.0 (m, 2H), 2.05 (m, 1H), 2.6–3.2 (m, 6H), 3.55–3.8 (m, 4H), 4.02, 4.22 (m, t, 1H), 4.75 (m, 1H), 4.90, 5.01 ((d,d), 1H), 6.12 (s, 1H), 6.68 (d, 2H), 7.30 (m, 5H), 7.49 (d, 2H).

MS(ES–): 550 (M–1), 568 ((M+H2O)–1).

EXAMPLE 44

Pharmacokinetics in Sprague-Dawley Rats Following Single Oral Dose

In order to study the pharmacokinetics of the prodrugs of this invention, we administered single oral doses of a series of prodrugs of this invention, as well as VX-478, to male and female Sprague-Dawley rats. Administration of molar equivalents of a series of prodrugs of this invention in a variety of pharmaceutical vehicles was tested.

Separate groups of male and female Sprague-Dawley rats (3/sex/group) received oral doses of compound 229 by oral gavage, in different vehicles at the same dose equivalent (40 mg/kg molar equivalent of VX-478). The different vehicles for compound 229 were: 1) water; 2) 5/4/1; 3) PEG 400; 4) TPGS/PEG 400; and 5) PEG. The vehicles for VX-478 were: 1) 33% TPGS/PEG400/PEG; and 2) 12.5% TPGS/PEG 400/PEG.

Blood samples were collected following administration at various time intervals and analyzed for the presence of both compound 229 and its metabolite, VX-478, by HPLC and MS methods. The results of this study are tabulated below (Table IV).

TABLE IV

| Compound | 229 | 229 | 229 | 229 | VX-478 | VX-478 |
|---|---|---|---|---|---|---|
| vehicle | $H_2O$ | $H_2O$:PG:EtOH 5:4:1 | PEG 400 | TPGS/PEG 400/PG | 33% TPGS/ PEG 400/PG | 12.5% TPGS/ PEG 400/PG |
| number of rats | 3 | 3 | 3 | 3 | 6 | ≧3 |
| Molar equiv. dose/478 Dose (mg/Kg) | 40 PO | 40 PO | 40 PO | 40 PO | 41 PO | 50 PO |
| AUC (ug · hr/ml) | 11.7 ± 4.8 | 10.6 ± 7.4 | 7.4 ± 1.8 | 8.2 ± 1.6 | 29.6 ± 5.8 | 16.2 ± 1.8 |
| Cmax ($\mu M$) | 7.1 ± 1.7 | 3.3 ± 0.6 | 3.1 ± 0.3 | 3.0 ± 0.7 | 14.0 ± 2.2 | 6.0 ± 1.0 |
| half life (hr) | 1.7* | 3.4* | 2.8* | 2.8* | 2.5 ± 0.9 | 2.2 ± 1.0 |
| Relative Avail. of VX-478 | 39.5[†] 90.2[††] | 35.8[†] 81.8[††] | 25.0[†] 57.1[††] | 27.7[†] 63.3[††] | reference | reference | a dose of 50 mg/Kg of compound 229 is equal to 40 mg/Kg of VX-478.
no compound 229 was detected in plasma at 15 min. (first data point).
*Represents the harmonic mean
[†]Relative availability of VX-478 when compared to a prototype clinical formulation
[††]Relative availability of VX-478 when compared to a prototype toxicology formulation We performed a similar study on dogs using both a solid capsule formulation of compound 229 and an ethanolic/methyl cellulose solution formulation, as compared to a TPGS-containing solution formulation of VX-478. The results from this study are presented below in Table V.

TABLE V

| Compound | 229 | 229 | VX-478 |
|---|---|---|---|
| vehicle | solid capsule | methyl cellulose in 5% EtOH/water | 22% TPGS/PEG 400/PG |
| number of dogs | 2 | 2 | >2 |
| Molar equiv. dose/ 478 Dose (mg/Kg) | 17 PO | 17 PO | 17 PO |
| AUC (ug*hr/ml) | 16.7 ± 2.7 | 14.2 ± 3.2 | 23.5 ± 7.4 |
| Cmax (µg/ml) | 6.1 ± 1.7 | 6.3 ± 0.3 | 6.8 ± 1.1 |
| Tmax (hr) | 2.3 ± 0.6 | 0.5 ± 0.5 | 1.0 ± 0.8 |
| Relative Avail. of VX-478 (%) | 71.1 | 60.4 | reference |

The results demonstrate that oral administration of compound 229 as an aqueous solution resulted in improved bioavailability in comparison to the other vehicles studied. Also, following administration of compound 229, none of that compound was detected in the first time point blood sample (or later samples), suggesting first pass metabolism to VX-478. Comparison of the aqueous dose of compound 229 with the two non-aqueous formulations used for VX-478 indicated equivalence in delivery as illustrated by the range found for the bioavailability.

EXAMPLE 45

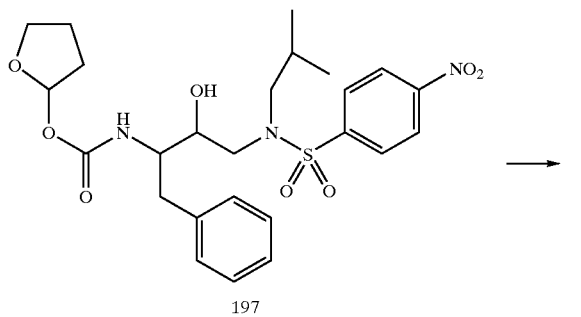

197

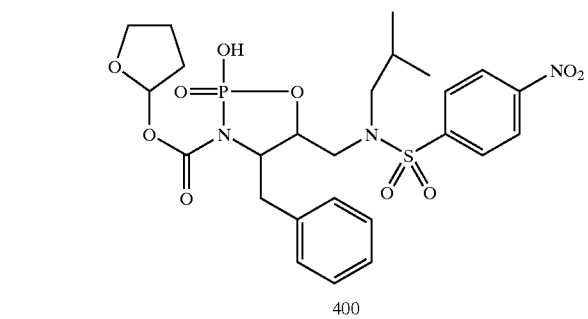

400

We added 0.28 ml (3.0 mmol) POCl₃ to a stirred solution of 1.07 g (2.0 mmol) of compound 197 in 10 ml anhydrous pyridine at 5° C. The mixture was allowed to warm up to room temperature and stirred at 20° C. for 3 hours. The mixture was cooled to 0° C., and quenched with 10 ml water. The solvents were removed under reduced pressure, the residue was dissolved in 100 ml ethyl acetate and washed with 20 ml 1M sodium bicarbonate solution. The organic phase was dried with anhydrous magnesium sulfate, filtered then concentrated. Chromatographic purification (SiO2, EtOAc) produce 280 mg of compound 400 (Yield=23%).

1H-NMR(DMSO-d6): 0.86 (dd, 6H), 2.05 (m, 2H), 2.84 (d, 2H), 2.95 (dd, 1H),3.06 (m, 1H), 3.25 (dd, 1H), 3.50–3.70 (m, 4H), 4.20 (m, 1H), 4.35 (m, 1H),7.2–7.4 (m, 5H), 7.9–8.1 (m, 2H) , 8.40 (m, 2H).

MS(ES-): 596 (M-1).

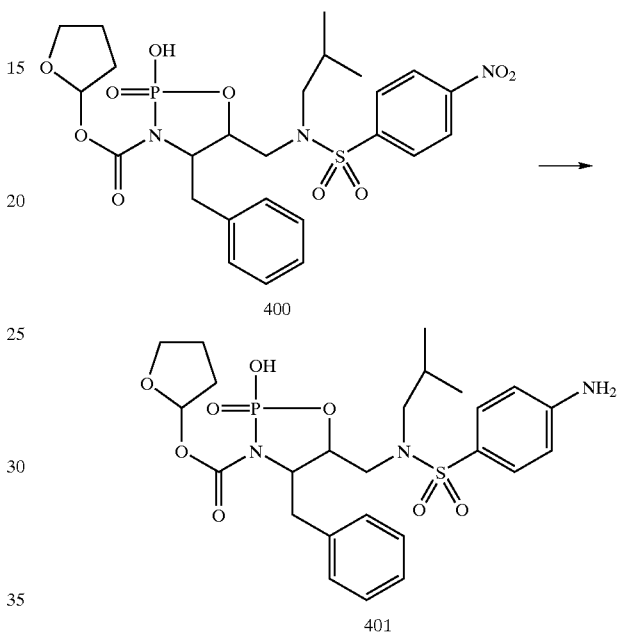

Compound 400 was converted to compound 401 using the standard hydrogenation method described above employing H2/PdC(10%), atmospheric pressure, 4 hours at room temperature, solvent: MeOH—H₂O (5:1). Yeld of 401=68%.

1H-NMR(DMSO-d6): 0.85 (dd, 6H), 2.0 (m, 2H), 2.6–3.1 (m, 4H), 4.15 (m, 1H),4.40 (m, 1H), 6.1 (s (br), 1H), 6.61 m (2H), 7.2–7.5 (m, 7H).

MS (ES-): 566 (M-1).

EXAMPLE 46

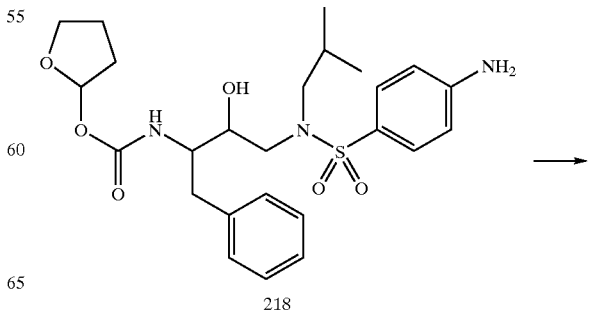

218

-continued

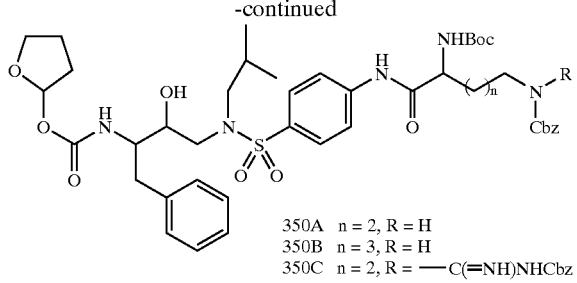

350A n = 2, R = H
350B n = 3, R = H
350C n = 2, R = —C(=NH)NHCbz

We added 1.0 g (2.8) mmol Na-t-Boc-nd-Cbz-L-Ornithine was added to stirred solution of 1.2 g (3.15 mmol) HATU, 0.2 g (1.47 mmol) HOAt, 0.4 g (4.0 mmol) NMM in 10 ml DMF. The mixture was stirred at room temperature for 2 hrs. then 0.5 g (1.0 mmol) of compound 218 was added and the solution was stirred at 50° C. for 12 hours. The mixture was cooled to room temperature, 100 ml ether was added and extracted with 5×50 ml water. The organic phase was dried with anhydrous magnesium sulfate, filtered and concentrated under reduced pressure. The residue was purified by silica gel chromatography (Hexane-EtOAc (1:1) then EtOAc (neat)) to yield 410 mg (48%) of compound 350.

Compound 350 A

1H-NMR(CDCl3): 0.85 (dd, 6H), 1.41 (s, 3H), 1.45 (s, 6H), 1.60 (m, 4H), 1.90 (m, 2H), 2.1 (m, 1H), 2.75–3.25 (m, 6H), 3.60–3.90 (m, 6H), 5.15 (dd, 2H),7.2–7.4 (m, 10H), 7.68 (dd, 4H).

MS (ES-): 852 (M-1).
MS (ES+): 854 (M+1).

Compound 350 B

1H-NMR(CDCl3): 0.81 (dd, 6H), 1.39 (s, 9H), 1.40–2.10 (m, 9H), 2.70–3.20 (m, 8H), 3.60–3.90 (m, 6H), 4.10 (m, 1H), 4.80 (d, 1H), 5.04 (s(br), 2H), 7.1–7.3 (m, 10H), 7.61 (s, 4H).

MS (ES-): 866 (M-1).
MS (ES+): 868 (M+1).

Compound 350 C

1H-NMR(CDCl3): 0.86 (dd, 6H), 1.40 (s, 3H), 1.46 (s, 6H), 1.60–2.10 (m, 7H), 2.70–3.15 (m, 6H), 3.60 (d, 1H), 3.70–4.10 (m, 6H), 4.81 (d, 1H), 5.05–5.30(m, 7H), 7.18–7.4 (m, 17H), 7.55 (d, 2H).

MS (FAB+): 1030 (M+1), 1052 (M+Na).

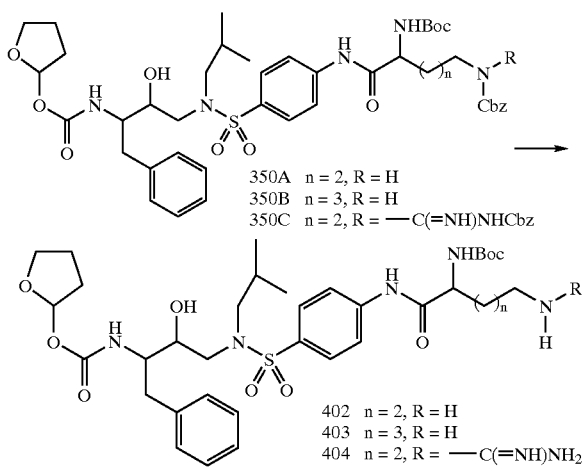

350A n = 2, R = H
350B n = 3, R = H
350C n = 2, R = —C(=NH)NHCbz 402 n = 2, R = H
403 n = 3, R = H
404 n = 2, R = —C(=NH)NH2

Compounds 350A, 350B and 350C were converted to Compounds 402, 403, and 404, respectively, using the standard hydrogenation method set forth above: H2/PdC (10%), atmospheric pressure, 4 hours, room temperature, solvent: EtOH, Yield: 81%.

Compound 402

1H-NMR(CDCl3): 0.80 (dd, 6H), 1.38 (s, 9H), 1.8 (m, 6H), 2.10 (m, 2H), 2.75–3.30 (m, 8H), 3.50–4.00 (m, 7H), 4.55 (s(br), 1H), 7.2 (m, 5H), 7.60 (d, 2H), 7.81 (d, 2H).

MS (ES+): 720 (M+1).

Compound 403

1H-NMR(CDCl3): 0.87 (dd, 6H), 1.45 (s, 9H), 1.50–2.00 (m, 8H), 2.08 (m, 1H), 2.75–3.15 (m, 8H), 3.60 (d, 1H), 3.75–3.90 (m, 5H), 4.28 (s(br), 1H), 4.92 (d, 1H), 5.11 (m, 1H), 5.27 (s(br), 1H), 7.28–7.35 (m, 5H), 7.70 (s, 4H).

MS (ES+) 734 (M+1).

Compound 404

1H-NMR(CDCl3): 0.80 (dd, 6H), 1.32 (s, 9H), 1.50–2.10 (m, 7H), 2.60–3.20 (m, 8H), 3.40–3.80 (m, 5H), 5.0(s(br), 1H), 7.05–7.2 (m, 5H), 7.50–7.80 (m,4H).

MS (ES+): 762 (M+1).

EXAMPLE 47

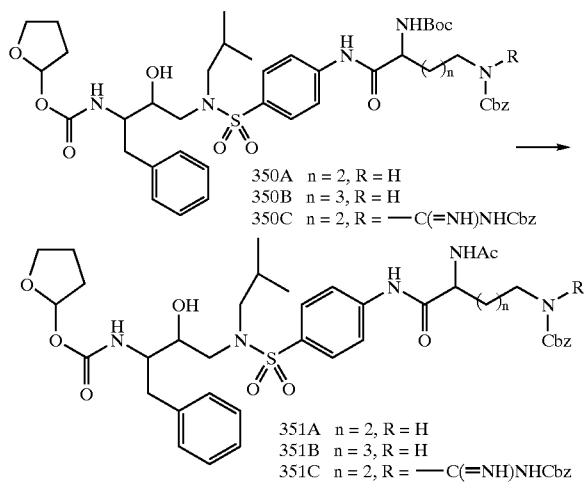

350A n = 2, R = H
350B n = 3, R = H
350C n = 2, R = —C(=NH)NHCbz 351A n = 2, R = H
351B n = 3, R = H
351C n = 2, R = —C(=NH)NHCbz

We added 5 ml TFA to a stirred solution of 260 mg (0.3 mmol) Compound 350A, 350B, or 350C in 20 ml chloroform. The mixture was stirred for 5 hours at room temperature, and then the solvents were removed under reduced pressure. The residue was dissolved in 20 ml dichloromethane, 2 ml (11 mmol) N,N-diisopropylethylamine and 1 ml (10 mmol) acetic anhydride was added to the reaction mixture. The solution was stirred for 1 hour, then the solvents were removed. The residue was purified by silica gel chromatography (eluant: EtOAc-EtOH (9:1)) to obtain 170 mg (71%) of compound 351A, 351B or 351C, respectively.

Compound 351A

1H-NMR(CDCl3): 0.85 (dd, 6H), 1.60 (m, 3H), 1.80–2.00 (m, 3H), 2.06 (2, 3H), 2.75 (dd, 1H), 2.80–3.20 (m, 5H), 3.60–3.90 (m, 7H), 4.85 (d, 2H), 5.10 (m, 3H), 6.46 (d, 1H), 7.25 (m, 10H), 7.67 (s, 4H), 9.30 (s, 1H).

MS (ES+): 796 (M+1), 818 (M+Na).

Compound 351B

1H-NMR(CDCl3): 0.80 (dd, 6H), 1.38 (m, 2H), 1.50 (m, 2H), 1.70 (m, 2H), 1.85 (m, 2H), 2.00 (s, 3H), 2.70 (dd, 1H), 2.75–3.20 (m, 7H), 3.55 (d, 1H), 3.75 (m, 6H), 4.45 (q, 1H), 4.83 (d, 1H), 4.95 (t, 1H), 5.03 (s(br), 3H), 6.46 (d, 1H), 7.20 (m, 10H), 7.61 (s, 4H), 9.29 (s, 1H).

MS (ES+): 810 (M+1), 832 (M+Na).

81

Compound 351C

1H-NMR(CDCl3): 0.85 (dd, 6H), 1.70–2.00 (m, 6H), 2.07 (s, 3H), 2.70 (dd, 1H), 2.80–3.00 (m, 3H), 3.10 (dd, 1H), 3.60 (d, 1H), 3.65–4.00 (m, 6H), 4.1(m, 1H), 4.62 (q, 1H), 4.82 (d, 1H), 5.00–5.30 (m, 5H), 7.10–7.40 (m, 15H), 7.55 (d, 2H), 7.65 (m, 3H) 9.18 (s(br), 1H), 9.45 (s(br), 1H), 9.56(s(br),1H).

MS (FAB+): 972 (M+1), 994 (M+Na).

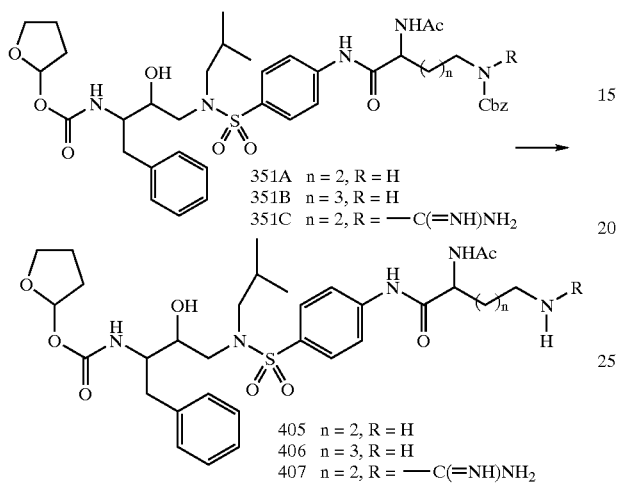

351A n = 2, R = H
351B n = 3, R = H
351C n = 2, R = —C(=NH)NH2

405 n = 2, R = H
406 n = 3, R = H
407 n = 2, R = —C(=NH)NH2

The conversion of compounds 351A, 351C, and 351C to 405, 406, and 407, respectively was achieved by standard hydrogenation using H2/PdC(10%), atmospheric pressure, 4 hours at room temperature, solvent: EtOH, Yield=46%.

Compound 405

1H-NMR(DMSO-d6): 0.85 (dd, 6H), 1.62 (m, 3H), 1.81 (m, 2H), 1.94 (s, 3H), 2.00–2.2 (m, 2H), 2.75–3.00 (m, 5H), 3.10 (m, 2H), 3.50–3.80 (m, 5H), 4.54 (m, 1H),5.00 (m, 1H), 5.11 (d, 1H), 7.2–7.4 (m, 5H), 7.80–8.00 (m, 5H), 10,72 (s, 1H).

MS (ES+): 662 (M+1).

Compound 406

1H-NMR(DMSO-d6): 0.80 (dd, 6H), 1.30–1.80 (m, 7H), 1.85 (s, 3H), 1.95–2.10 (m, 2H), 2.70 (m, 4H), 2.99 (m, 2H), 3.30 (m, 5H), 3.40–3.80 (m, 4H), 4.35 (m, 1H), 4.90 (s, 1H), 5.00 (d, 1H), 7.08–7.25 (m, 5H), 7.50 (s(br), 1H), 7.71 (d, 2H), 7.79 (d, 2H), 10.54 (s, 1H).

MS (ES+): 676 (M+1).

Compound 407

1H-NMR(DMSO-d6): 0.80 (dd, 6H), 1.40–1.60 (m, 4H), 1.75 (m, 2H), 1.86 (s, 3H), 2.00 (m, 2H), 2.75 (dt, 2H), 3.00 (m, 2H), 3.10 (q, 2H), 3.40–3.70 (m, 5H), 4.39 (q, 1H), 4.92 (s (br), 1H), 5.01 (d, 1H), 7.20 (m, 5H), 7.70 (d+m, 3H), 7.81 (d, 2H), 8.30 (d, 1H), 10.60 (s, 1H).

MS (ES+): 704 (M+1).

82

EXAMPLE 48

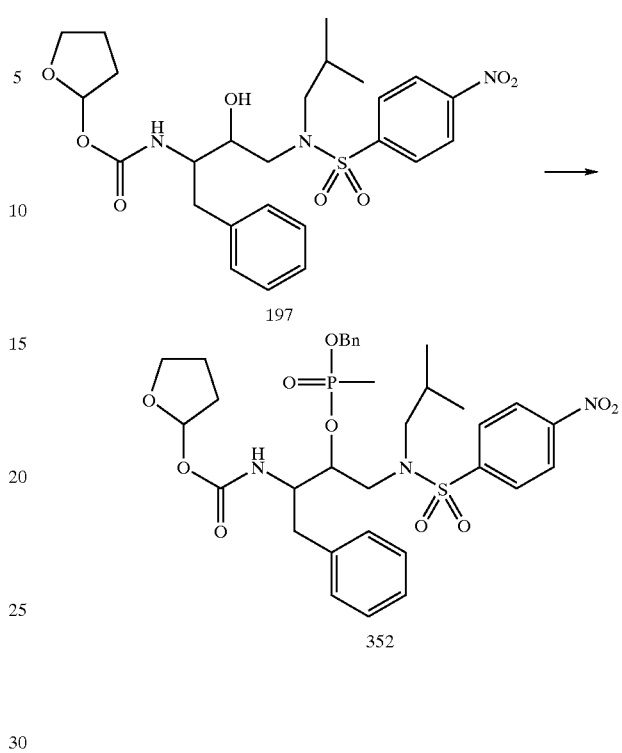

197

352

We added 1.0 g (7.5 mmol) methanephosphonyl dichloride to a stirred solution of 2.14 g (4.00 mmol) of compound 197 in 20 ml toluene, containing 10% pyridine. The mixture was stirred at 100° C. for 5 hours, then cooled to 40° C., 2 g (18.5 mmol) benzyl alcohol was added to the reaction, and the mixture was stirred at 20° C. for 12 hours. The solid was filtered, washed with 2×10 ml toluene and the filtrate was concentrated under reduced pressure. The residue was purified using silica gel chromatography (eluants: Hexane-EtOAc (1:1), then EtOAc (neat)) to yield 550 mg (20%) of compound 352.

1H-NMR(CDCl3): 0.67 (dd, 6H), 1.53 (d, 3H), 1.70 (m, 1H), 1.90–2.10 (m, 2H), 2.65–3.20 (m, 6H), 3.55 (d, 1H), 3.80 (m, 3H), 4.10 (m, 1H), 4.70 (q, 1H), 4.90–5.20 (m, 4H), 6.37 (d, 1H), 7.2–7.4 (m, 10H), 7.90 (d, 2H), 8,30 (d, 2H).

MS (ES+): 704 (M+1), 726 (M+Na).

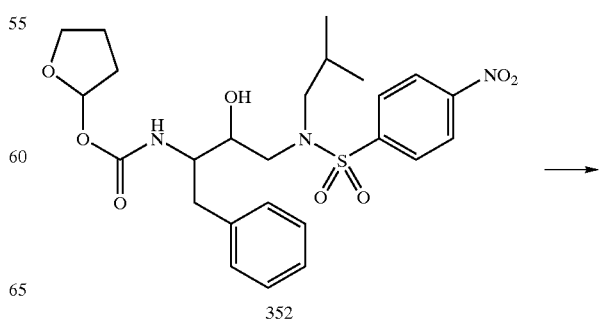

352

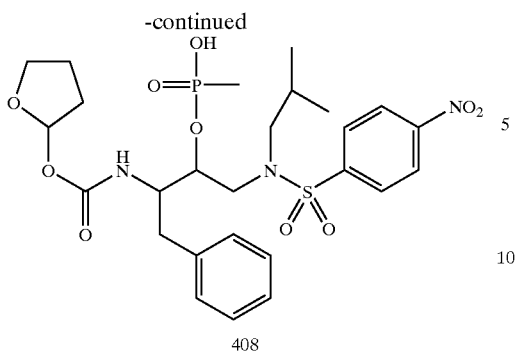

408

Compound 352 was converted to compound 408 using standard hydrogenation method: H2/PdC(10%), atmospheric pressure, 2 hours, room temperature, solvent: MeOH; Yield: 78%.

1H-NMR(DMSO-d6): 0.84 (dd, 6H), 1.44 (d, 3H), 1.82 (m, 1H), 1.90–2.10(m, 2H), 2.62 (m, 2H), 2.95 (m, 2H), 3.10 (d, 1H), 3.39 (d, 1H), 3.45–3.80 (m, 4H), 4.14 (t, 1H), 4.53 (m, 1H), 5.00 (s (br), 1H), 6.68 (d, 2H), 7.2–7.4 (m, 5H), 7.50 (d, 2H).

MS (ES−): 582 (M−1).

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound of formula I:

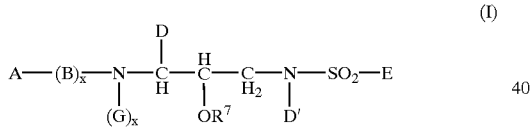

(I)

wherein:

A is selected from Ht; —R'—Ht;

each R' is independently selected from —C(O)—, —S(O)$_2$—, —C(O)—C(O)—, —O—C(O)—, —O—S(O)$_2$, —N(R$^2$)—S(O)$_2$—, —N(R$^2$)—(O)— or —N(R$^2$)—C(O)—C(O)—;

each Ht is independently selected from C$_3$–C$_7$ cycloalkyl; C$_5$–C$_7$ cycloalkenyl; C$_6$–C$_{10}$ aryl; or a 5–7 membered saturated or unsaturated heterocycle, containing one or more heteroatoms selected from N, N(R$^2$), O, S and S(O)$_n$; wherein said aryl or said heterocycle is optionally fused to Q; and wherein any member of said Ht is optionally substituted with one or more substituents independently selected from oxo, —OR$^2$, SR$^2$, —R$^2$, —N(R$^2$)$_2$, —(C$_1$–C$_4$)-alkyl substituted with OH and optionally substituted with Q, —CN, —C(O)O—R$^2$, —C(O)—N(R$^2$)$_2$, —S(O)$_2$—N(R$^2$)$_2$, —N(R$^2$)—C(O)—R$^2$, —C(O)—R$^2$, —S(O)$_n$—R$^2$, —OCF$_3$, —S(O)$_n$—Q, methylenedioxy, —N(R$^2$)—S(O)$_2$—R$^2$, halo, —CF$_3$, —NO$_2$, Q, —OQ, —OR$^7$, —SR$^7$, —R$^7$, —N(R$^2$)(R$^7$) or —N(R$^7$)$_2$;

each R$^2$ is independently selected from H, or (C$_1$–C$_4$)-alkyl optionally substituted with Q;

B, when present, is —N(R$^2$)—C(R$^3$)$_2$—C(O)—;

each x is independently 0 or 1;

each R$^3$ is independently selected from H, Ht, (C$_1$–C$_6$)-alkyl, (C$_2$–C$_6$)-alkenyl, (C$_3$–C$_6$)-cycloalkyl or (C$_5$–C$_6$)-cycloalkenyl; wherein any member of said R$^3$, except H, is optionally substituted with one or more substituents selected from —OR$^2$, —C(O)—NH—R$^2$, —S(O)$_n$—N(R$^2$)$_2$, Ht, —CN, —SR$^2$, —CO$_2$R$^2$, N(R$^2$)—C(O)—R$^2$;

each n is independently 1 or 2;

G, when present, is selected from H, R$^7$ or (C$_1$–C$_4$)-alkyl;

D and D' are independently selected from Q; (C$_1$–C$_6$)-alkyl, which is optionally substituted with one or more groups selected from (C$_3$–C$_6$)-cycloalkyl, —OR$^2$, —R$^3$, —O—Q or Q; (C$_2$–C$_4$)-alkenyl, which is optionally substituted with one or more groups selected from (C$_3$–C$_6$)-cycloalkyl, —OR$^2$, —R$^3$, —O—Q or Q; (C$_3$–C$_6$)-cycloalkyl, which is optionally substituted with or fused to Q; or (C$_5$–C$_6$)-cycloalkenyl, which is optionally substituted with or fused to Q;

each Q is independently selected from a 3–7 membered saturated, partially saturated or unsaturated carbocyclic ring system; or a 5–7 membered saturated, partially saturated or unsaturated heterocyclic ring containing one or more heteroatoms selected from O, N, S, S(O)$_n$ or N(R$^2$); wherein any ring in Q is optionally substituted with one or more groups selected from oxo, —OR$^2$, —R$^2$, —N(R$^2$)$_2$, —N(R$^2$)—C(O)—R$^2$, —(C$_1$–C$_4$)-alkyl substituted with OH and optionally substituted with Q, —CN, —C(O)OR$^2$, —C(O)—N(R$^2$)$_2$, halo or —CF$_3$;

E is selected from Ht; O—Ht; Ht—Ht; (C$_3$–C$_6$)-saturated carbocycle, which is optionally substituted with one or more groups selected from R$^4$ or Ht; or (C$_5$–C$_6$)-unsaturated carbocycle, which is optionally substituted with one or more groups selected from R$^4$ or Ht;

each R$^4$ is independently selected from —OR$^2$, —SR$^2$, —C(O)—NHR$^2$, —S(O)$_2$—NHR$^2$, halo, —N(R$^2$)—C(O)—R$^2$, —N(R$^2$)$_2$ or —CN;

each R$^7$ is independently selected from

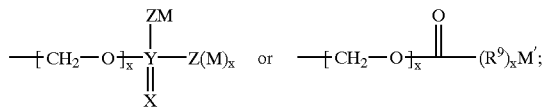

wherein each M is independently selected from H, Li, Na, K, Mg, Ca, Ba, N(R$^2$)$_4$, (C$_1$–C$_{12}$)-alkyl, (C$_2$–C$_{12}$)-alkenyl, or —R$^6$; wherein 1 to 4 —CH$_2$ radicals of the alkyl or alkenyl group, other than the —CH$_2$ that is bound to Z, is optionally replaced by a heteroatom group selected from O, S, S(O), S(O)$_2$, or N(R$^2$); and wherein any hydrogen in said alkyl, alkenyl or R$^6$ is optionally replaced with a substituent selected from oxo, —OR$^2$, —R$^2$, N(R$^2$)$_2$, N(R$^2$)$_3$, R$^2$OH, —CN, —C(O)OR$^2$, —C(O)—N(R$^2$)$_2$, S(O)$_2$—N(R$^2$)$_2$, N(R$^2$)—C(O)—R$_2$, C(O)R$^2$, —S(O)$_n$—R$^2$, OCF$_3$, —S(O)$_n$—R$^6$, N(R$^2$)—S(O)$_2$—R$^2$, halo, —CF$_3$, or —NO$_2$;

M' is H, (C$_1$–C$_{12}$)-alkyl, (C$_2$–C$_{12}$)-alkenyl, or —R$^6$; wherein 1 to 4 —CH$_2$ radicals of the alkyl or alkenyl group is optionally replaced by a heteroatom group selected from O, S, S(O), S(O)$_2$, or N(R$^2$); and wherein any hydrogen in said alkyl, alkenyl or R$^6$ is optionally replaced with a substituent selected from oxo, —OR$^2$, —R$_2$, —N(R$^2$)$_2$, N(R$^2$)$_3$, —R$^2$OH, —CN, —CO$_2$R$_2$, —C(O)—N(R²)₂, —S(O)₂—N(R²)₂, —N(R²)—C(O)—R₂, —C(O)R², —S(O)ₙ—R₂, —OCF₃, —S(O)ₙ—R⁶, —N(R²)—S(O)₂—R², halo, —CF₃, or —NO₂;

Z is —CH₂—, O, S, —N(R²)—, or, when M is not present, H, CH₃, or —N(R²)₂;

Y is P or S;

X is O or S;

R⁹ is C(R²)₂, O or N(R²); and wherein when Y is S, Z is not S; and

R⁶ is a 5–6 membered saturated, partially saturated or unsaturated carbocyclic or heterocyclic ring system, or an 8–10 membered saturated, partially saturated or unsaturated bicyclic ring system; wherein any of said heterocyclic ring systems contains one or more heteroatoms selected from O, N, S, S(O)ₙ or N(R²); and wherein any of said ring systems optionally contains 1 to 4 substituents independently selected from OH, C₁–C₄ alkyl, O—(C₁–C₄)-alkyl or O—C(O)—(C₁–C₄)-alkyl.

2. The compound according to claim 1, wherein at least one R⁷ is selected from:

[structure: —H₂C—O—C(O)—O—CH₂CH₂—N(CH₃)₂],

[structure: acetyl-N-methylpiperazine], [structure: acetyl-OCH₂CH₂OCH₃],

[structure: acetyl-CH₂-O-CH₃],

-(L)-lysine, —PO₃Na₂,

[structure: acetyl-O-CH₂CH₂-NMe₂], [structure: acetamido-CH₂CH₂-NHAc],

-(L)-tyrosine,

[structure: acetyl-piperazine-NH],

—PO₃Mg, —PO₃(NH₄)₂, —CH₂—OPO₃Na₂,

[structure: acetamido-CH₂CH₂-NH₂],

-(L)-serine, —SO₃Na₂,

[structure: acetyl-O-CH₂CH₂-N(Me)-CH₂CH₂-NMe₂],

—SO₃Mg, —SO₃(NH₄)₂, —CH₂—OSO₃Na₂, —CH₂—OSO₃(NH₄)₂,

[structure: acetamido-CH₂CH₂CH₂-NH₂], [structure: acetyl-pyrrolidine-NH₂],

[structure: acetyl-O-CH₂CH₂-O-CH₂CH₂-OMe],

[structure: acetamido-CH₂CH₂CH₂CH₂-NH₂], [structure: acetyl-pyrrolidine-NH₂],

[structure: acetyl-N-methylpiperazine], acetyl,

[structure: methyl ethyl ketone], [structure: methyl butyl ketone],

-(L)-valine, -(L)-glutamic acid, -(L)-aspartic acid, -(L)-γ-t-butyl-aspartic acid,

[structure: acetyl-O-tetrahydrofuran],

-(L)-(L)-3-pyridylalanine, -(L)-histidine, —CHO,

[structure: CF₃-C(O)-CH₃],

[structure: acetyl-O-tetrahydrofuran],

[structure: acetyl-O-(CH₂)₄-O-sugar(OAc)₃],

[structure: methyl phosphonate ethyl-NH₃⁺], [structure: methyl phosphonate ethyl-NMe₃⁺],

[structure: ethyl phosphate], [structure: ethyl sulfite],

PO$_3$K$_2$, PO$_3$Ca, PO$_3$-spermine, PO$_3$-(spermidine)$_2$ or PO$_3$-(meglamine)$_2$.

3. The compound according to claim 2, wherein said compound has formula XXII:

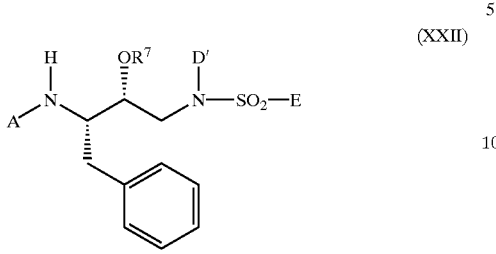

(XXII)

wherein A, D', R$^7$ and E are as defined in claim 1.

4. The compound according to claim 3, wherein

A is selected from 3-tetrahydrofuryl-O—C(O)—, 3-(1,5-dioxane)-O—C(O)—, or 3-hydroxy-hexahydrofura[2,3-b]-furanyl-O—C(O)—;

D' is (C$_1$–C$_4$)-alkyl which is optionally substituted with one or more groups selected from the group consisting of (C$_3$–C$_6$)-cycloalkyl, —OR$^2$, —R$^3$, —O—Q and Q;

E is (C$_6$–C$_{10}$)-aryl optionally substituted with one or more substituents selected from oxo, —OR$^2$, SR$^2$, —R$^2$, —N(R$^2$)$_2$, —(C$_1$–C$_4$)-alkyl substituted with OH and optionally substituted with Q, —CN, —C(O)O—R$^2$, —C(O)—N(R$^2$)$_2$, —S(O)$_2$—N(R$^2$)$_2$, —N(R$^2$)—C(O)—R$^2$, —C(O)—R$^2$, —S(O)$_n$—R$^2$, —OCF$_3$, —S(O)$_n$—Q, methylenedioxy, —N(R$^2$)—S(O)$_2$—R$^2$, halo, —CF$_3$, —NO$_2$, Q, —OQ, —OR$^7$, —SR$^7$, —R$^7$, —N(R$^2$)(R$^7$) or —N(R$^7$)$_2$; or a 5-membered heterocyclic ring containing one S and optionally containing N as an additional heteroatom, wherein said heterocyclic ring is optionally substituted with one to two groups independently selected from —CH$_3$, R$^4$, or Ht; and Ht, insofar as it is defined as part of R$^3$, is defined as in claim 1 except for the exclusion of heterocycles.

5. The compound according to claim 4, wherein:

A is 3-tetrahydrofuryl-O—C(O)—;

G is hydrogen;

D' is isobutyl;

E is phenyl substituted with N(R$^7$)$_2$;

each M is independently selected from H, Li, Na, K, Mg, Ca, Ba, C$_1$–C$_4$ alkyl or N(R$^2$)$_4$; and each M' is H or C$_1$–C$_4$ alkyl.

6. The compound according to claim 3, wherein:

E is a 5-membered heterocyclic ring containing one S and optionally containing N as an additional heteroatom, wherein said heterocyclic ring is optionally substituted with one to two groups independently selected from —CH$_3$, R$^4$ or Ht.

7. The compound according to claim 3, wherein:

E is Ht substituted with N(R$^7$)$_2$;

R$^7$ in the —OR$^7$ group shown in formula XXII is —PO(OM)$_2$ or C(O)CH$_2$OCH$_2$CH$_2$OCH$_2$CH$_2$OCH$_3$ and both R$^7$ in the —N(R$^7$)$_2$ substituent of Ht are H; or R$^7$ in —OR$^7$ group shown in formula XXII is C(O)CH$_2$OCH$_2$CH$_2$OCH$_3$, one R$^7$ in the —N(R$^7$)$_2$ substituent of Ht is C(O)CH$_2$OCH$_2$CH$_2$OCH$_3$ and the other R$^7$ in the —N(R$^7$)$_2$ substituent of Ht is H; and wherein M is H, Li, Na, K or C$_1$–C$_4$ alkyl.

8. The compound according to claim 2, wherein said compound has formula XXIII:

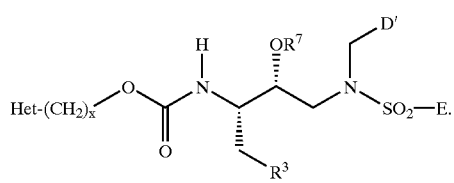

(XXIII)

9. The compound according to claim 8, wherein:

R$^3$ is (C$_1$–C$_6$)-alkyl, (C$_2$–C$_6$)-alkenyl, (C$_5$–C$_6$)-cycloalkyl, (C$_5$–C$_6$)-cycloalkenyl, or a 5–6 membered saturated or unsaturated heterocycle; wherein any member of R$^3$ is optionally substituted with one or more substituents selected from the group consisting of —OR$^2$, —C(O)—NH—R$^2$, —S(O)$_n$N(R$^2$)$_2$, —Ht, —CN, —SR$^2$, —C(O)O—R$^2$ and N(R$^2$)—C(O)—R$^2$; and D' is (C$_1$–C$_3$)-alkyl or C$_3$ alkenyl; wherein D' is optionally substituted with one or more groups selected from (C$_3$–C$_6$)-cycloalkyl, —OR$^2$, —O—Q or Q.

10. The compound according to claim 9, wherein R$^7$ in the —OR$^7$ group depicted in formula XXIII is —PO(OM)$_2$ or —C(O)—M'.

11. The compound according to claim 2, wherein said compound has formula XXXI:

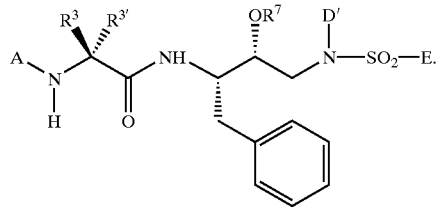

(XXXI)

12. The compound according to claim 11, wherein:

A is R$^1$—Ht;

each R$^3$ is independently (C$_1$–C$_6$)-alkyl which is optionally substituted with —OR$^2$, —C(O)—NH—R$^2$, —S(O)$_n$N(R$^2$)$_2$, —Ht, —CN, —SR$^2$, —CO$_2$R$^2$ or —N(R$^2$)—C(O)—R$^2$; and D' is (C$_1$–C$_4$)-alkyl, which is optionally substituted with (C$_3$–C$_6$)-cycloalkyl, —OR$^2$, —O—Q; and E is Ht, Ht—Ht and —N(R$^2$)(R$^3$).

13. The compound according to claim 12, wherein R$^7$ in the —OR$^7$ group depicted in formula XXXI is —PO(OM)$_2$ or —C(O)—M'.

14. The compound according to claim 1, wherein said compound is selected from any one of compound numbers 198 to 217, 225–229, 231, 237 to 242, 245 to 254, 261 to 267, 308 or 243 to 244 as depicted below:

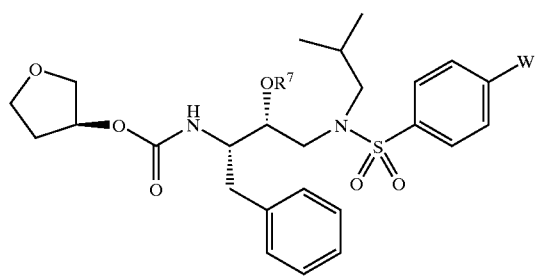
| CMPD | R⁷ | W |
|------|-----|-----|
| 198 | acetyl-O-(4-nitrophenyl) | —NO₂ |
| 199 | acetyl-(4-methylpiperazin-1-yl) | —NH₂ |
| 200 | acetyl-O-CH₂CH₂-NMe₂ | —NH₂ |
| 201 | acetyl-NH-CH₂CH₂-NHAc | —NH₂ |
| 202 | acetyl-(piperazin-1-yl) | —NH₂ |
| 203 | acetyl-NH-CH₂CH₂-NH₂ | —NH₂ |
| 204 | acetyl-NH-CH₂CH₂CH₂-NH₂ | —NH₂ |
| 205 | acetyl-NH-(CH₂)₄-NH₂ | —NH₂ |
| 206 | acetyl-(3(S)-aminopyrrolidin-1-yl) | —NH₂ |
| 207 | acetyl-(3(R)-aminopyrrolidin-1-yl) | —NH₂ |

-continued
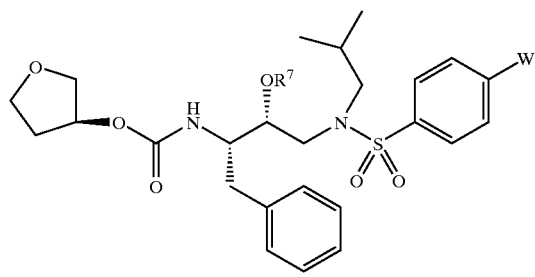
| CMPD | R⁷ | W |
|---|---|---|
| 208 | (S)-CH₂CH(NH₂)C(O)- with CH₂-C₆H₄-OBn (4-OBn-benzyl) | —NO₂ |
| 209 | -CH₂C(O)CH₂OCH₂CH₂OMe | —NO₂ |
| 210 | -CH₂C(O)CH₂OCH₂CH₂OMe | —NH₂ |
| 211 | (S)-CH₂CH(NH₂)C(O)- with CH₂-C₆H₄-OH (4-OH-benzyl) | —NH₂ |
| 212 | -CH₂C(O)CH₂CH₂OCH₃ | —NH₂ |
| 213 | -CH₂C(O)CH₂OCH₂CH₂OH | —NH₂ |
| 214 | (S)-CH₂C(O)CH(NH₂)CH₂CH₂CH₂CH₂NH₂ | —NH₂ |
| 215 | -CH₂C(O)CH₂OCH₂CH₂OCH₂CH₂OMe | —NH₂ |
| 216 | -CH₂C(O)CH₂OCH₂CH₂N(Me)CH₂CH₂NMe₂ | —NH₂ |
| 217 | -CH₂C(O)CH₂-(piperazin-1-yl) | —NH₂ |

-continued
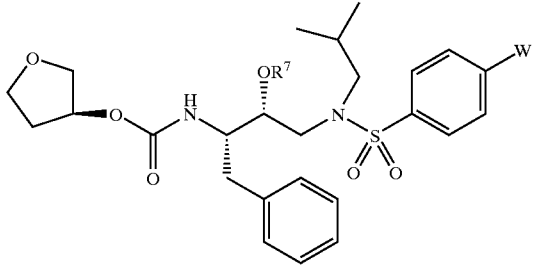
| CMPD | R⁷ | W |
|---|---|---|
| 225 | 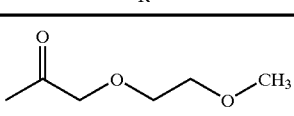 | 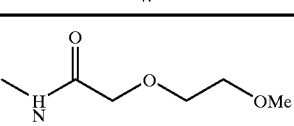 |
| 226 | 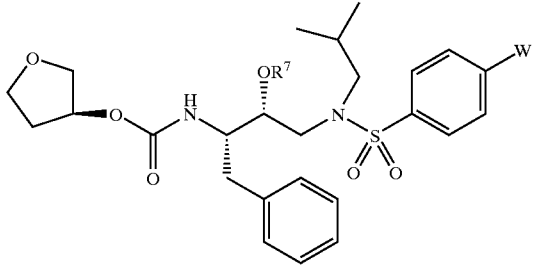 | —NO₂ |
| 227 | 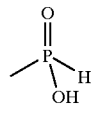 | —NO₂ |
| 228 |  | —NH₂ |
| 229 | 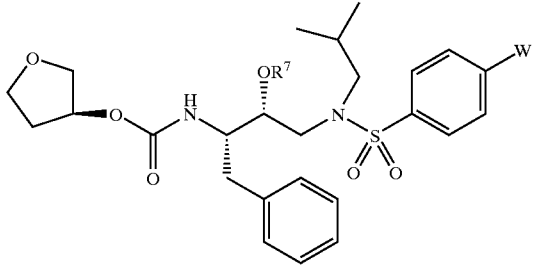 | —NH₂ |
| 231 | 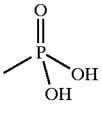 |  |
| 237 | 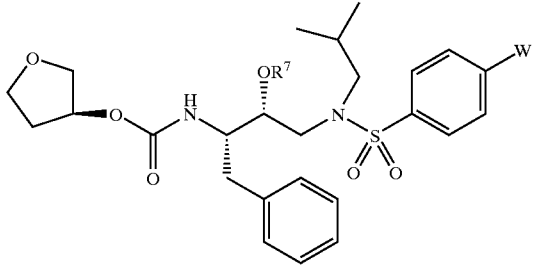 | —NO₂ |
| 238 | 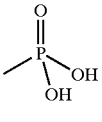 | —NO₂ |
| 239 | —SO₃H | —NO₂ |
| 240 | —SO₃H | —NH₂ |
| 241 |  | —NO₂ |
| 242 | 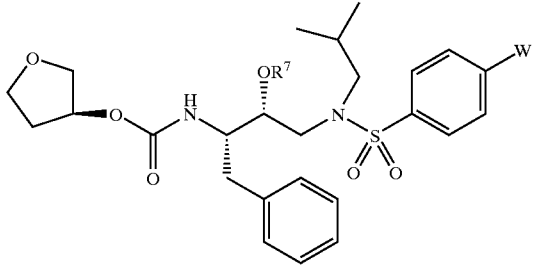 | —NH₂ |

-continued

| CMPD | R⁷ | W |
|---|---|---|
| 245 | methylphosphinic acid (P(=O)(OH)(CH₃)H) | —NH₂ |
| 246 | (S)-3-amino-4-hydroxy-2-butanone-yl | —NH₂ |
| 247 | 1-methoxypropan-2-one-yl (CH₃C(=O)CH₂OCH₃) | —NH₂ |
| 248 | acetyl (CH₃C(=O)—) | —NH₂ |
| 249 | propionyl (CH₃CH₂C(=O)—) | —NH₂ |
| 250 | pentanoyl (CH₃CH₂CH₂CH₂C(=O)—) | —NH₂ |
| 251 | 3-amino-4-methyl-2-oxopentyl | —NH₂ |
| 252 | 4-amino-5-oxohexanoic acid-yl | —NH₂ |

-continued
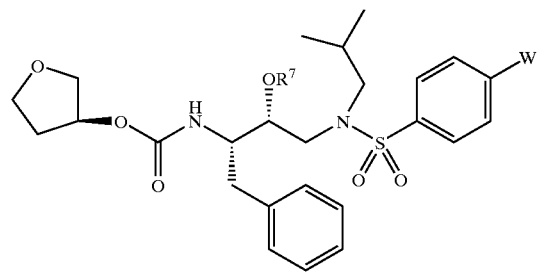
| CMPD | R⁷ | W |
|------|-----|-----|
| 253 | (3-amino-4-oxopentanoic acid group) | —NH₂ |
| 254 | (3-propyltetrahydrofuran-3-yl group) | —NH₂ |
| 261 | methyl(hydroxy)phosphinyl | NHC(O)CH₃ |
| 262 | C(O)CH₂CH₃ | NHC(O)CH₂CH₃ |
| 263 | C(O)CH₂CH₂CH₂CH₃ | NHC(O)CH₂CH₂CH₂CH₃ |
| 264 | PO₃K₂ | —NH₂ |
| 265 | PO₃Ca | —NH₂ |
| 266 | PO₃Mg | —NH₂ |
| 267 | (2-amino-1-(tert-butoxycarbonyl)-4-oxopentyl) | —NH₂ |
| 308 | (N-acetyl-N-methyl-2-(methylamino)ethyl) | —NH₂ |

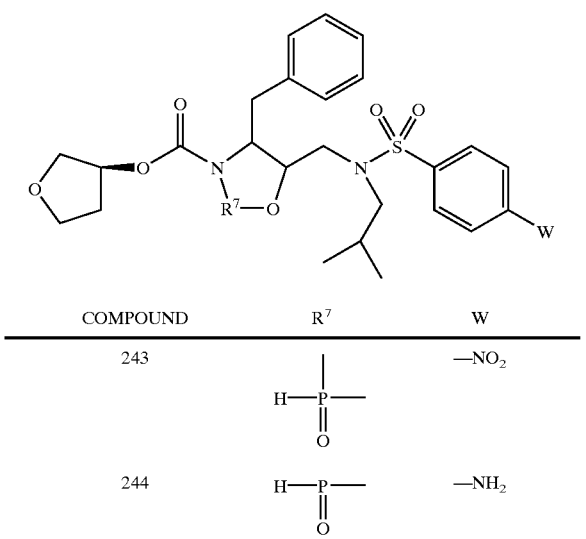

| COMPOUND | R⁷ | W |
|---|---|---|
| 243 | H—P(=O)— with H below | —NO₂ |
| 244 | H—P(=O)— with H below | —NH₂ |

15. The compound according to claim 3, wherein:
A is 3-hexahydrofura[2,3-b]-furanyl-O—C(O)—;
D' is (C₁–C₄)-alkyl which is optionally substituted with one or more groups selected from the group consisting of (C₃–C₆)-cycloalkyl, —OR², —R³, —O—Q and Q;
E is (C₆–C₁₀)-aryl optionally substituted with one or more substituents selected from oxo, —OR², SR², —R²₁, —N(R²)₂, —(C₁–C₄)-alkyl substituted with OH and optionally substituted with Q, —CN, —C(O)O—R², —C(O)—N(R²)₂, —S(O)₂—N(R²)₂, —N(R²)—C(O)—R², —C(O)—R², —S(O)ₙ—R², —OCF₃, —S(O)ₙ—Q, methylenedioxy, —N(R²)—S(O)₂—R², halo, —CF₃, —NO₂, Q, —OQ, —OR⁷, —SR⁷, —R⁷, —N(R²)(R⁷) or —N(R⁷)₂; or a 5-membered heterocyclic ring containing one S and optionally containing N as an additional heteroatom, wherein said heterocyclic ring is optionally substituted with one to two groups independently selected from —CH₃, R⁴, or Ht; and
Ht, insofar as it is defined as part of R³, is defined as in claim 1 except for the exclusion of heterocycles.

16. The compound according to claim 15, wherein:
D' is isobutyl; and
E is phenyl substituted with —N(R²)₂.

17. The compound according to claim 3 having the structure:

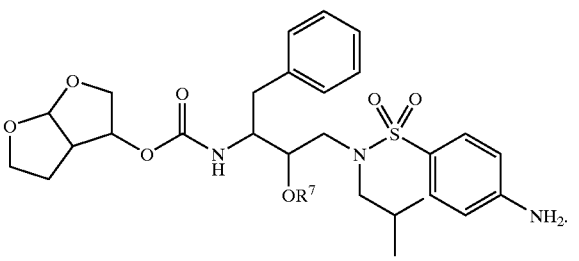

18. The compound according to claim 16, wherein:
each M is independently selected from H, Li, Na, K, Mg, Ca, Ba, C₁–C₄ alkyl or —N(R²)₄; and
each M' is H or C₁–C₄ alkyl.

19. The compound according to claim 17, wherein:
each M is independently selected from H, Li, Na, K, Mg, Ca, Ba, C₁–C₄ alkyl or —N(R²)₄; and
each M' is H or C₁–C₄ alkyl.

20. The compound according to claim 3, having the structure:

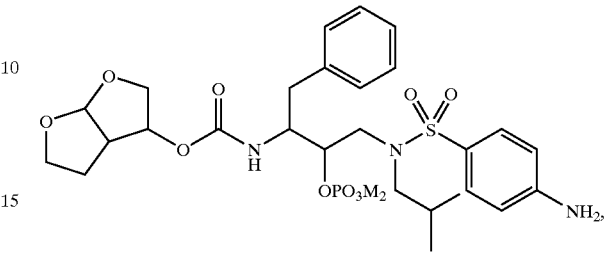

wherein each M is Na or K.

21. A compound having the structure:

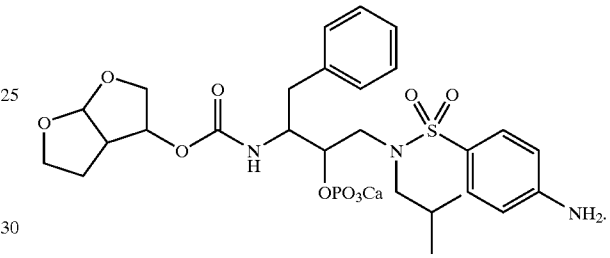

22. A pharmaceutical composition, comprising a compound according to any one of claims 1–7 or 8–14 in an amount effective to treat infection by a virus that is characterized by an aspartyl protease; and a pharmaceutically acceptable carrier, adjuvant or vehicle.

23. The pharmaceutical composition according to claim 22 wherein said virus is HIV.

24. The pharmaceutical composition according to claim 22, wherein said pharmaceutical composition is formulated for oral administration.

25. The pharmaceutical composition according to claim 22, further comprising one or more agents selected from an anti-viral agent, an HIV protease inhibitor other than a compound according to claim 1, and an immunostimulator.

26. The pharmaceutical composition according to claim 25, further comprising one or more agents selected from zidovudine (AZT), zalcitabine (ddC), didanosine (ddI), stavudine (d4T), lamivudine (3TC), abacavir (1592U89), saquinavir (Ro 31-8959), indinavir (MK-639, L-735,524), ritonavir (ABT 538, A84538), nelfinavir (AG 1343), N,N'-di-m-aminobenzyl-4,7-dibenzyl-5,6-dihydroxy-1,3-diazacyclohept-2-one (XM 450), [(1S,2S,4R)-2-hydroxy-5-[[[(1S)-2-methyl-1-[[[(1S)-2-(4-morpholinyl)-2-oxo-1-(phenylmethyl)ethyl]amino]carbonyl]propyl]amino]-5-oxo-1,4-bis(phenylmethyl)pentyl]-carbamic acid 1,1-dimethylethyl ester (CGP 53,437), polysulfated polysaccharides, ganciclovir, ribavirin, acyclovir, TIBO, nevirapine, IL-2, GM-CSF, interferon alpha, or erythropoietin (EPO).

27. A pharmaceutical composition, comprising a compound according to any one of claims 15 to 21 in an amount effective to treat infection by a virus that is characterized by an aspartyl protease; and a pharmaceutically acceptable carrier, adjuvant or vehicle.

28. The pharmaceutical composition according to claim 27, wherein said virus is HIV.

29. The pharmaceutical composition according to claim 27, wherein said pharmaceutical composition is formulated for oral administration.

30. The pharmaceutical composition according to claim 27, further comprising one or more agents selected from an anti-viral agent, an HIV protease inhibitor other than a compound according to claim 1, and an immunostimulator.

31. The pharmaceutical composition according to claim 30, further comprising one or more agents selected from zidovudine (AZT), zalcitabine (ddC), didanosine (ddI), stavudine (d4T), lamivudine (3TC), abacavir (1592U89), saquinavir (Ro 31-8959), indinavir (MK-639, L-735,524), ritonavir (ABT 538, A84538), nelfinavir (AG 1343), N,N'-di-m-aminobenzyl-4,7-dibenzyl-5,6-dihydroxy-1,3-diaza-cyclohept-2-one (XM 450), [(1S,2S,4R)-2-hydroxy-5-[[[(1S)-2-methyl-1-[[[(1S)-2-(4-morpholinyl)-2-oxo-1-(phenylmethyl)ethyl]amino]carbonyl]propyl]amino]-5-oxo-1,4-bis(phenylmethyl)pentyl]-carbamic acid 1,1-dimethylethyl ester (CGP 53,437), polysulfated polysaccharides, ganciclovir, ribavirin, acyclovir, TIBO, nevirapine, IL-2, GM-CSF, interferon alpha, or erythropoietin (EPO).

32. A method for inhibiting aspartyl protease activity in a mammal, comprising the step of administering to said mammal a pharmaceutical composition according to claim 22.

33. A method for treating HIV infection in a mammal comprising the step of administering to said mammal a pharmaceutical composition according to claim 22.

34. The method according to claim 33, wherein said mammal is additionally administered one or more additional agents selected from an anti-viral agent, an HIV protease inhibitor other than a compound according to claim 1, and an immunostimulator either as a part of a single dosage form with said pharmaceutical composition or as a separate dosage form.

35. The method according to claim 34, wherein said additional agent is selected from zidovudine (AZT), zalcitabine (ddC), didanosine (ddI), stavudine (d4T), lamivudine (3TC), abacavir (1592U89), saquinavir (Ro 31-8959), indinavir (MK-639, L-735,524), ritonavir (ABT 538, A84538), nelfinavir (AG 1343), N,N'-di-m-aminobenzyl-4,7-dibenzyl-5,6-dihydroxy-1,3-diaza-cyclohept-2-one (XM 450), [(1S,2S,4R)-2-hydroxy-5-[[[(1S)-2-methyl-1-[[[(1S)-2-(4-morpholinyl)-2-oxo-1-(phenylmethyl)ethyl]amino]carbonyl]propyl]amino]-5-oxo-1,4-bis(phenylmethyl)pentyl]-carbamic acid 1,1-dimethylethyl ester (CGP 53,437), polysulfated polysaccharides, ganciclovir, ribavirin, acyclovir, TIBO, nevirapine, IL-2, GM-CSF, interferon alpha, or erythropoietin (EPO).

36. The method according to claim 33, wherein said step of administering comprises oral administration.

37. A method for inhibiting aspartyl protease activity in a mammal, comprising the step of administering to said mammal a pharmaceutical composition according to claim 27.

38. A method for treating HIV infection in a mammal comprising the step of administering to said mammal a pharmaceutical composition according to claim 27.

39. The method according to claim 38, wherein said mammal is additionally administered one or more additional agents selected from an anti-viral agent, an HIV protease inhibitor other than a compound according to claim 1, and an immunostimulator either as a part of a single dosage form with said pharmaceutical composition or as a separate dosage form.

40. The method according to claim 39, wherein said additional agent is selected from zidovudine (AZT), zalcitabine (ddC), didanosine (ddI), stavudine (d4T), lamivudine (3TC), abacavir (1592U89), saquinavir (Ro 31-8959), indinavir (MK-639, L-735,524), ritonavir (ABT 538, A84538), nelfinavir (AG 1343), N,N'-di-m-aminobenzyl-4,7-dibenzyl-5,6-dihydroxy-1,3-diaza-cyclohept-2-one (XM 450), [(1S,2S,4R)-2-hydroxy-5-[[[(1S)-2-methyl-1-[[[(1S)-2-(4-morpholinyl)-2-oxo-1-(phenylmethyl)ethyl]amino]carbonyl]propyl]amino]-5-oxo-1,4-bis(phenylmethyl)pentyl]-carbamic acid 1,1-dimethylethyl ester (CGP 53,437), polysulfated polysaccharides, ganciclovir, ribavirin, acyclovir, TIBO, nevirapine, IL-2, GM-CSF, interferon alpha, or erythropoietin (EPO).

41. The method according to claim 38, wherein said step of administering comprises oral administration.

* * * * *